US006159964A

United States Patent [19]

Ali et al.

[11] Patent Number: 6,159,964

[45] Date of Patent: Dec. 12, 2000

[54] VITRONECTIN RECEPTOR ANTAGONISTS

[75] Inventors: Fadia E. Ali, Cherry Hill, N.J.; William E. Bondinell, Wayne, Pa.; Richard M. Keenan, Malvern, Pa.; Thomas Wen-Fu Ku, Dresher, Pa.; William H. Miller, Schwenksville, Pa.; James Samanen, Phoenixville, Pa.

[73] Assignee: SmithKline Beecham Corporation, Philadelphia, Pa.

[21] Appl. No.: 09/091,937

[22] PCT Filed: Dec. 20, 1996

[86] PCT No.: PCT/US96/20327

§ 371 Date: Jul. 27, 1999

§ 102(e) Date: Jul. 27, 1999

[87] PCT Pub. No.: WO97/24124

PCT Pub. Date: Jul. 10, 1999

Related U.S. Application Data

[60] Provisional application No. 60/009,367, Dec. 29, 1995.

[51] Int. Cl.$^{7}$ ........................ A61K 31/5513; A61P 7/02; C07D 401/12

[52] U.S. Cl. ........................ 514/221; 540/512

[58] Field of Search ........................ 514/221; 540/512

[56] References Cited

U.S. PATENT DOCUMENTS 3,450,707 6/1969 Bailey .
3,627,754 12/1971 Ning et al. .

FOREIGN PATENT DOCUMENTS

WO 94 14776 7/1994 WIPO .
WO 96 00574 1/1996 WIPO .
WO 97 24336 7/1997 WIPO .

*Primary Examiner*—Robert W. Ramsuer

*Attorney, Agent, or Firm*—Mary E. McCarthy; Stephen Venetianer; Charles M. Kinzig

[57] ABSTRACT

Compounds of formula (I) are disclosed, wherein: A is a fibrinogen antagonist template; W is a linking moiety of the form —$(CHR^g)_a$—U—$(CHR^g)_b$—V—; $Q^1$, $Q^2$, $Q^3$ and $Q^4$ are independently N or C—$R^y$, provided that no more than one $Q^1$, $Q^2$, $Q^3$ and $Q^4$ is N; R' is H or $C_{1-6}$alkyl, $C_{3-7}$cycloalkyl-$C_{0-6}$-alkyl or Ar—$C_{0-6}$alkyl; $R^g$ is H or $C_{1-6}$alkyl, Het-$C_{0-6}$alkyl, $C_{3-7}$cycloalkyl-$C_{0-6}$alkyl or Ar—$C_{0-6}$alkyl; $R^k$ is $R^g$, —C(O)$R^g$ or —C(O)O$R^g$ $R^i$ is H, $C_{1-6}$alkyl, Het-$C_{0-6}$alkyl, $C_{3-7}$cycloalkyl-$C_{0-6}$alkyl, Ar—$C_{0-6}$alkyl, Het-$C_{0-6}$alkyl—U'—$C_{1-6}$alkyl, $C_{3-7}$cycloalkyl-$C_{0-6}$alkyl—U'—$C_{1-6}$alkyl or Ar—$C_{0-6}$alkyl—U'—$C_{1-6}$alkyl; $R^y$ is H, halo, —$OR^g$, —$SR^g$, —CN, —$NR^gR^k$, —$NO_2$, —$CF_3$, $CF_3S(O)_r$, —$CO_2R^g$, —$COR^g$ or —$CONR^g_2$, or $C_{1-6}$alkyl optionally substituted by halo, —$OR^g$, —$SR^g$, —CN, —$NR^8R''$, —$NO_2$, —$CF_3$, $R'S(O)_3$—, —$CO_2R^g$, —$COR^g$ or —$CONR^g_2$; U and V are absent or CO, $CR^g_2$, C(=$CR^g_2$), $S(O)_c$, O, $NR^g$, $CR^gOR^g$, $CR^g(OR^k)CR^g_2$, $CR^g_7CR^g(OR^k)$, C(O)$CR^g_2$, $CR^g_2$C(O), $CONR^i$, $NR^i$CO, OC(O), C(O)O, OC(S), C(S)$NR^g$, $NR^8$C(S), $S(O_2NR^g$, $NR^gS(O)_2N$=N, $NR^gNR^g$, $NR^gCR^g_2$, $NR^gCR^g_2$, $CR^g_2O$, $OCR^g_2$, $CR^g$=$CR^g$, C≡C, Ar or Het; a is 0, 1 or 2; c is 0, 1 or 2; r is 0, 1 or 2; and u is 0 or 1; or pharmaceutically acceptable salts thereof, which are vitronectin receptor antagonists useful in the treatment of osteoporosis.

(I)

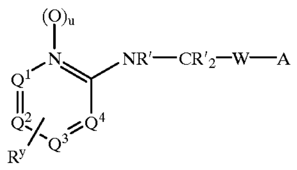

5 Claims, No Drawings

VITRONECTIN RECEPTOR ANTAGONISTS

This application is a 371 of PCT/US96/20327 filed Dec. 20, 1996 which claims the benefit of provisional application Ser. No. 60/009,367, filed Dec. 29, 1995.

FIELD OF THE INVENTION

This invention relates to pharmaceutically active compounds which inhibit the vitronectin receptor and are useful for the treatment of diseases wherein ihibition of the vitronectin receptor is indicated, such as inflammation, cancer, angiogenesis, atherosclerosis, restenosis, and diseases wherein bone resportion is a factor.

BACKGROUND OF THE INVENTION

Integrins are a superfamily of cell adhesion receptors, which are transmembrane glycoproteins expressed on a variety of cells. These cell surface adhesion receptors include gpIIb/IIIa, the fibrinogen receptor, and $\alpha_v\beta_3$, the vitronectin receptor. The fibrinogen receptor gpIIb/IIIa is expressed on the platelet surface and it mediates platelet aggregation and the formation of a hemostatic clot at the site of a bleeding wound. Philips, et al., *Blood.,* 1988, 71, 831.

The vitronectin receptor $\alpha_v\beta_3$ is expressed on a number of cells, including endothelial, smooth muscle, osteoclast, and tumor cells, and, thus, it has a variety of functions. The $\alpha_v\beta_3$ receptor expressed on the membrane of osteoclast cells is believed to play a role in the bone resportion process and contribute to the development of osteoporosis. Ross, et al., *J. Biol. Chem.,* 1987, 262, 7703; Fisher, et al., *Endochrinology* 1993, 132, 1411; Bertolini et al., *J. Bone Min. Res.,* 6, Sup. 1, S146 252; EP 528 587 and 528 586. The $\alpha_v\beta_3$ receptor expressed on human aortic smooth muscle cells stimulates their migration into neointima, which leads to the formation of atherosclerosis and restenosis after angioplasty. Brown, et al., *Cardiovascular Res.,* 1994, 28, 1815. Additionally, a recent study has shown that a $\alpha_v\beta_3$ antagonist is able to promote tumor regression by inducing apoptosis of angiogenic blood vessels. Brooks, et al., *Cell,* 1994, 79, 1157. Thus, agents that would block the vitronectin receptor would be useful in treating diseases mediated by this receptor, such as osteoporosis, atherosclerosis, restenosis and cancer.

Alig et al., EP 0 381 033, Hartman, et al., EP 0 540,334, Blackburn, et al., WO 93/08174, Bondinell, et al., WO 95/18619, Bondinell, et al., WO 94/14776, Blackburn, et al. WO 95/04057, Egbertson, et al, EP 0 478 328, Sugihara, et al. EP 529,858, Porter, et al., EP 0 542 363, and Fisher, et al., EP 0 635 492, and many others disclose certain compounds that are useful for selectively inhibiting the fibrinogen receptor. PCT/US95/08306, filed Jun. 29, 1995 (SmithKline Beecham Corp.) and PCT/US95/08146 filed Jun. 29, 19951995 (SmithKline Beecham Corp.) disclose vitronectin receptor selective antagonists. However, there are few reports of compounds which are potentvitronectin receptor antagonists. It has now been discovered that certain appropriately substituted amino pyridine compounds are potent inhibitors of the vitronectin receptor. In particular, it has been discovered that the amino pyridine moiety may be combined with a fibrinogen atagonist template to prepare compounds which are more potent inhibitors of the vitronectin receptor than the fibrinogen receptor.

SUMMARY OF THE INVENTION

This invention comprises compounds of the formula (I) as described hereinafter, which have pharmacological activity for the inhibition of the vitronection receptor and are useful in the treatment of inflammation, cancer, cardiovascular disorders, such as atherosclerosis and restenosis, and diseases wherein bone resorption is a factor, such as osteoporosis.

This invention is also a pharmaceutical composition comprising a compound according to formula (I) and a pharmaceutically acceptable carrier.

This invention is also a method of treating diseases which are mediated by the vitronectin receptor. In a particular aspect, the compounds of this invention are useful for treating atherosclerosis, restenosis, inflammation, cancer and osteoporosis.

DETAILED DESCRIPTION

This invention comprises novel compounds which are more potent inhibitors of the vitronectin receptor than the fibrinogen receptor. The compounds of the instant invention comprise a fibrinogen receptor antagonist template that is linked to an optionally substituted 2-pyridyl-amine moiety according to formula (I):

(I)

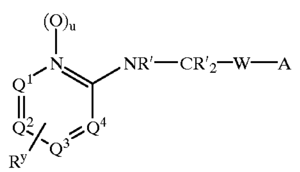

wherein

A is a fibrinogen antagonist template;

W is a linking moiety of the form —$(CHR^g)_a$—U—$(CHR^g)_b$—V—;

$Q^1$, $Q^2$ and $Q^3$ are independently N or C—$R^y$, provided that no more than one of $Q^1$, $Q^2$, $Q^3$ and $Q^4$ is N;

R' is is H or $C_{1-6}$alkyl, $C_{3-7}$cycloalkyl-$C_{0-6}$alkyl or Ar—$C_{0-6}$alkyl $R^g$ is H or $C_{1-6}$alkyl, Het-$C_{0-6}$alkyl, $C_{3-7}$cycloalkyl-$C_{0-6}$alkyl or Ar—$C_{0-6}$alkyl;

$R^k$ is $R^g$, —C(O)$R^g$ or —C(O)O$R^g$ $R^i$ is H, $C_{1-6}$alkyl, Het-$C_{0-6}$alkyl, $C_{3-7}$cycloalkyl-$C_{0-6}$alkyl, Ar—$C_{0-6}$alkyl, Het-$C_{0-6}$alkyl—U'—$C_{1-6}$alkyl, $C_{3-7}$cycloalkyl-$C_{0-6}$alkyl—U'—$C_{1-6}$alkyl or Ar—$C_{0-6}$alkyl—U'—$C_{1-6}$alkyl;

$R^y$ is H, halo, —O$R^g$, —S$R^g$, —CN, —N$R^gR^k$, —$NO_2$, —$CF_3$, $CF_3S(O)_r$—, —$CO_2R^g$, —CO$R^g$ or —CON$R^g_2$, or $C_{1-6}$alkyl optionally substituted by halo, —O$R^g$, —S$R^g$, —CN, —N$R^g$R", —$NO_2$, —$CF_3$, R'S $(O)_3$—, —$CO_2R^g$, —CO$R^g$ or —CON$R^g_2$;

U and V are absent or CO, $CR^g_2$, C(=$CR^g_2$), $S(O)_c$, O, N$R^g$, $CR^g$O$R^g$, $CR^g(OR^k)CR^g_2$, $CR^g_2CR^g(OR^k)$, C(O)$CR^g_2$, $CR^g_2$C(O), CON$R^i$, N$R^i$CO, OC(O), C(O)O, C(S)O, OC(S), C(S)N$R^g$, N$R^g$C(S), $S(O)_2NR^g$, N$R^g$S$(O)_2$N=N, N$R^g$N$R^g$, N$R^g$C$R^g_2$, N$R^g$C$R^g_2$, $CR^g_2$O, O$CR^g_2$, $CR^g$=$CR^g$, C≡C, Ar or Het;

a is 0, 1, 2 or 3;

b is 0, 1 or 2;

c is 0, 1 or 2;

u is 0 or 1;

and pharmaceutically acceptable salts thereof.

Preferably, $Q^1$, $Q^2$, $Q^3$ and $Q^4$ are all CH, and u is 0.

Suitably, R' is H and R" is H or $C_{1-4}$alkyl.

Suitably, W is $—(CHR^g)_a—CONR^i—$ or $—(CHR^g)_a—NR^iCO—$

A fibrinogen receptor antagonist is an agent that inhibits the binding of fibrinogen to the platelet-bound fibrinogen receptor GPIIb-IIIa. Many fibrinogen antagonists are known to the art. As used herein, the term "fibrinogen receptor antagonist template" means the core structure of a fibrinogen receptor antagonist, said core containing an acidic group and being linked to an organic group substituted with a basic nitrogen moiety. Typically, the core structure adds some form of rigid spacing between the acidic moiety and the basic nitrogen moiety, and contains one or more ring structures or amide bonds to effect this. It is preferred that about twelve to fifteen, more preferably thirteen or fourteen, intervening covalent bonds via the shortest intramolecular path will exist between the acidic group of the fibrinogen receptor antagonist template and nitrogen of the o-amino substituent on the pyridine moiety in formula (I). It is an object of this invention that a fibrinogen receptor antagonist is converted to a vitronectin receptor antagonist by replacing the basic nitrogen group in a fibrinogen receptor antagonist with an optionally substituted pyrid-2-yl-amino group. In addition, the number of intervening covalent bonds between the acidic moiety and the nitrogen of the o-amino substituent on the pyridine ring will be about two to five, preferably three or four, covalent bonds shorter than the number of intervening covalent bonds between the acidic moiety and the basic nitrogen group of the fibrinogen antagonist. The identity of the linking moiety W may be chosen to obtain the proper spacing between the acidic moiety of the fibrinogen antagonist template and the nitrogen atom of the pyridine. Generally, a fibrinogen antagonist will have an intramolecular distance of about 16 angstroms between the acidic moiety (e.g., the atom which gives up the proton or accepts the electron pair) and the basic moiety (e.g., which accepts a proton or accepts the electron pair) and the basic moiety (e.g., which accepts a proton or donates and electron pair), while the vitronectin antagonist will have about 14 angstroms between the respective acidic and basic centers.

for purposes of illustration, using the 7-2,3,4,5-tetrahydro-3-oxo-4-methyl-benzodiazepine fibrinogen antagonist template disclosed in WO 93/08174 as a suitable fibrinogen antagonist template, the compound (R,S)-7-[[[4-(aminoiminomethyl)phenyl]amino]carbonyl]-4-(2-phenylethyl)-1,3,4,5-tetrahydro-3-oxo-2H-1,4-benzodiazepine-2-acetic acid, which is potent and selective fibrinogen antagonist, is converted to a potent and selective vitronectin receptor antagonist by replacing the 4-(aminoiminomethyl) phenyl moiety with the (pyrid-2-yl) ethyl moiety. As illustrated below in FIG. 1, in the former case, there are sixteen intervening covalent bonds between the acidic moiety and the basic moiety; in the fibrinogent antagonist whereas, in the latter case there are 13 intervening covalent bonds in the vitronectin antagonist of this invention.

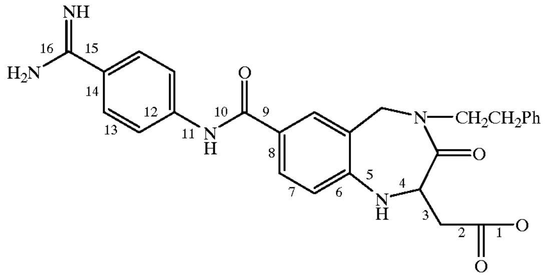

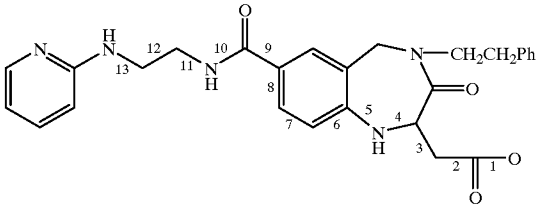

In fact the 4-(aminoiminomethyl)phenyl moiety is a common substituent on fibrinogen antagonist templates known to the art, and simple replacement of this moiety with an optionally substituted (pyrid-2-yl)aminoethyl moiety may serve as guide to converting compounds having known fibrinogen antagonist templates into vitronectin receptor antagonists.

Also included in this invention are pharmaceutically acceptable addition salts, complexes or prodrugs of the compounds of this invention. Prodrugs are considered to be any covalently bonded carriers which release the active parent drug according to formula (I) in vivo. In cases wherein the compounds of this invention may have one or more chiral centers, unless specified, this invention includes each unique nonracemic compound which may be synthesized and resolved by conventional techniques. In cases in which compounds have unsaturated carbon-carbon double bonds, both the cis (Z) and trans (E) isomers are within the scope of this invention. In cases wherein compounds may exist in tautomeric forms, such as keto-enol tautomers, such as

 and , and exist in tautomeric forms, such as keto-enol tautomers, such as each tautomeric form is contemplated as being included within this invention whether existing in equilibrium or locked in one form by appropriate substitution with R'.

The compounds of formula (I) inhibit the binding of vitronectin and other RGD-containing peptides to the vitronectin ($\alpha_v\beta_3$) receptor. Inhibition of the vitronectin receptor on osterclasts inhibits osteoclastic bone resorption and is useful in the treatment of diseases wherein bone resorption is associated with pathology, such as osteoporosis. Additionally, since the compounds of the instant invention inhibit vitronectin receptors on a number of different types of cells, said compounds would be useful in the treatment of inflammation and cardiovascular diseases, such as atherosclerosis and restenosis, and would be useful as anti-metastatic and antitumor agents.

Table I, below, describes certain fibrinogen receptor antagonists, whose core structures are useful in carrying out the instant invention. Reference should be made to the patent applications and other publications for their full disclosures, including the methods of preparing said templates and specific compounds embodying said templates. The entire disclosure of the noted patent applications and other publications is incorporated herein by reference as though fully set forth. The list following is not intended to limit the scope of the present invention, but only to illustrate certain known templates.

TABLE I

Adir et Compagnie

FR 928004, June 30, 1992, Fauchere, et al.
EP 0578535, June 29, 1993, Fauchere, et al.
CA 2128560, Jan. 24, 1995, Godfroid, et al.

Asahi Breweries, Ltd.

JP05239030, Sep. 17, 1993.

Asahi Glass

WO 90/02751, Ohba, et al., Sept. 8, 1989.
WO 90/1115950, Mar. 22, 1990, Ohba, et al.
EP 0406428, Jan. 9, 1991.
WO 92/09627, Isoai, A. et al., Nov. 29, 1991.

Cassella AG

DE 4207254, (Der 93-289298/37) Mar. 7, 1992, Zoller, et al.
EP 93904010, Feb. 24, 1993.
EP 0565896, Mar. 18, 1993, Klinger, et al.
EP 0566919, (Der 93-338002/43) Apr. 3, 1993, Zoller, et al.
EP 580008, (Der 94-027663104) July 6, 1993, Zoller, et al.
DE 224414, July 6, 1993, Zoller, et al.
EP 584694, (Der 94-067259/09) Apr. 2, 1994.
DE 4301747, (Der 94-235891/29) Jul. 28, 1994, Zoller, et al.
DB 4308034, (Der 94-286666/36) Sept. 15, 1994, Klinger, O. et al.
DE 4309867, Sept. 29, 1994, Klingler, et al.

Chiron

WO 93/07169, (Der 93-134382/16), Mar. 15, 1993, Devlin, et al.

Ciba Geigy

EP 0452210, (Der 91-305246/42) Apr, 5, 1990, Describes aminoalkanoyl-GDF analogs.
EP 0452257, Mar. 26, 1991, Allen, et al.: Describes aminoalkanoylAsp-Phe analogs.

COR Therapeutics

WO 90/15620, June 15, 1990.
EP 0477295, Apr. 1, 1992, Scarborough, et al.
WO 92/08472, May 29, 1992, Scarborough, et al.
WO 93/223356, April 27, 1993, Swift, et al.
EP 0557442, Sept. 1, 1993, Scarborough, et al.
Scarborough, et al., J. Biol Chem., 266, 9359, 1991.

Daiichi Pharm Co Ltd.

JP 05078344-A, (Der 93-140339/17) Mar. 30, 1993.

DuPont Merck

WO 93/07170, Apr. 15, 1993.
WO 94/11398, May 26, 1994: Wells, et al.
IL 109237, Jul. 31, 1994.
WO 94/22909, (Der 94-333113/41) Oct. 13, 1994, DeGrado, et al.
WO 94/22910, (Der 94-333114/41 Oct. 13, 1994: DeGrado, et al.
WO 94/22494, (Der 94-332838/41) Oct. 13, 1994: DeGrado, et al.
EP 625164, Nov. 23, 1994, Degrado, et al.
Mousa, et al, Circulation, 89, 3, 1994.
Jackson, J. Amer. Chem. Soc., 116, 3220, 1994.

Ellem Ind Farma Spa

GB 2207922, Aug, 3, 1988.

Farmitalia Erba SRL Carlo

EP 611765 (Der 94-265375/33), Aug 24, 1994: Cozzi, et al.

TABLE I-continued

Fuji Photo Film

JP 04208296-A (Der. 92-303598/38), Nov. 30, 1990.
JP 04213311-A (Der. 92-305482/38), Nov. 27, 1990.
JP 04217693-A, (Der 92-312284/38), Oct. 23, 1990.
JP 04221394-A (Der. 92-313678/38), Oct. 26, 1990.
JP 04221395-A (Der. 92-313679/38), Oct. 26, 1990.
JP 04221396-A (Der. 92-313680/38), Oct. 26, 1990.
JP 04221397-A (Der. 92-313681/38), Dec. 20, 1990.
EP 0482649 A2, April 29, 1992, Kojima, et al..
EP 0488258A2, June 3, 1992, Komazawa, et al..
EP 503301-A2, Feb. 14, 1991, Kitaguchi, et al..
JP 05222092, May 21, 1993, Nishikawa, et al..
JP 06239885, (Der 94-313705/39), Aug 30, 1993, Nishikawa, et al.
WO 9324448, (Der 93-405663/50), Dec. 9, 1993, Nishikawa, et al.
JP 06228189, (Der 94-299801/37), Aug. 16, 1994.
EP 619118, (Der 94-3 11647/39), Oct. 12, 1994, Nishikawa, et al..

Fujisawa

EP 0513675, May 8, 1992, Umekita, et al.
WO 940903-A1, Apr. 28, 1994, Takasugi, et al.
EP 0513675, (Der 92-383589/47).
WO 9500502, Jan, 5, 1995, Oku, et al,
FR 144633: Thromb Haem. 69, 706, 1993.
Cox, et al., Thromb. Haem., 69, 707, 1993.

Genentech

WO 90/15072 (Der 91007159.
WO 91/01331 (Der 91058116), July 5, 1990, Barker, et al.
WO 91/04247, Sept. 24, 1990, Webb.
WO 91/11458 (Der 91252610), Jan. 28, 1991, Barker, et al.
WO 92/07870, Oct. 24, 1991, Burnier, et al.
WO 92/17492, Oct. 15, 1992, Burnier, et al.
CA 2106314, Oct. 6, 1992, Burnier, et al.
WO 93/08174, Oct. 15, 1991, Blackburn, et al.
CA 2106314, Oct. 6, 1992, Burnier, et al.
EP 0555328, Aug. 18, 1993, Burnier, et al.
WO 95/04057, Feb. 9, 1995, Blackburn, et al.
Scarborough, et al., J. Biol Chem. 268, 1066, 1993.
Dennis, et al., Proc. Natl. Acad. Sci. USA, 87, 2471, 1989.
Barker, et al., J. Med. Chem., 35, 2040, 1992.
McDowell; Gadek, T. R., J. Amer. Chem. Soc., 114, 9245, 1992.

Glaxo

EP 537980, Oct. 13, 1992, Porter, et al.
EO 0542363, Nov. 10, 1992, Porter, et al.
WO 93/22303, Jan. 11, 1993, Middlemiss, et al.
WO 93/22303, Jan. 11, 1993, Middlemiss, et al.
WO 93/14077, Jan. 15, 1993, Porter, et al.
EP 609282 A1, Aug. 10, 1994, Porter, et al.
EP 612313, Aug. 31, 1994, Porter, et al.
EP 93911769, Apr. 20, 1994, Midlemiss, et al.
EP 637304 A1, Feb. 8, 1995, Middlemiss, et al.
Hann, et al., "An Investigation of the Bioactive Conformation of ARG-GLY-ASP Containing Cyclic Peptides and Snake Venom Peptides Which Inhibit Human Platelet Aggregation," In Molecular Recognition, Chemical and Biochemical Problems II", S. M. Roberts, Ed., The Royal Society of Chemistry, Cambridge, 1992.
Ross, B. C., "Nonpeptide Fibrinogen Receptor Antagonists," In Seventh RSC-SCI Medicinal Chemistry Symposium, The Royal Society of Chemistry Fine Chemicals and Medicinals Group and SCI Fine Chemicals Group, Churchill College, Cambridge, 1993, L20.
Pike, et al., Thromb. Haem., 69, 1071, 1993.

Hoechst

DE 4009506, Mar. 24, 1990, Konig, et al.

Hoffmann-La Roche

AU 9344935, (Der 94-118783/15), Mar. 10, 1994.
EP 0592791, Apr. 20, 1994, Bannwarth, et al..

Kogyo Gijutsuin

JP 06179696, June 28, 1994.

Kyowa Hakko Kogyo KK

JP 05078244-A, Mar. 30, 1993.

Laboratoire Chauvin

WO 9401456, Jan. 20, 1994, Regnouf, et al.

TABLE I-continued

La Jolla Cancer Res. Fndn

WO 9500544, Jan. 5, 1994, Pierschbacher, et al.
US 079441, Jan 5, 1994, Pierschbacher, et al.

Lilly/COR Therapeutics

EP 0635492, Jan. 25, 1995, Fisher. et al.

Medical Unlversity of South Carolina

EP 587770, Mar. 23, 1994, Halushka, et al.

Merck

EP 0368486 (Der 90-149427/20), Nov. 10, 1988.
EP 0382451 (Der 90248531).
EP 0382538 (Der 90248420).
EP 0410537, July 23, 1990, Nutt, et al..
EP 0410539, July 25, 1990, Nutt, et al..
EP 0410540, July 25, 1990, Nutt, et al..
EP 0410541, July 25, 1990, Nutt, et al.
EP 0410767, July 26, 1990, Nutt, et al.
EP 0411833, July 26, 1990, Nutt, et al.
EP 0422937, Oct. 11, 1990, Nutt, et al.
EP 0422938, Oct. 11, 1990, Nutt, et al.
EP 0487238, Octover 13, 1991, Connolly, et al.
EP 0437367 (Der 91209968), Sato et al.
EP 576898, Jan. 5, 1994, Jonczyk, et al.
WO 9409029, Apr. 28, 1994, Nutt, et al.
EP 618225, (Der 94-304404/38) Oct. 5, 1994.
DE 4310643, (Der 94-311172/39), Oct. 6, 1994, Jonczyk, et al., Describes cyclic RGD analogs as antimetastatic agents.
NO 9404093, Oct. 27, 1994, Jonczyk, et al.
EP 0632053, Jan. 4, 1995, Jonczyk, et al.
EP 0479481, Sept. 25, 1991, Duggan et al.
EP 0478328, Sept. 26, 1991, Egbertson, et al.
EP 0478362, Sept. 27, 1991, Duggan et al.
EP 0478363, SepL. 27, 1991, Laswell, et al.
EP 0512829, May, 7, 1992, Duggan, et al.
EP 0512831, May, 7, 1992, Duggan, et al.
EP 0528586, August 5, 1992, Egbertson, et al.
EP 0528587, August 5, 1992, Egbertson, et al.
EP 0540334, October 29, 1992, Hartman, et al.
US 5227490, Feb. 21, 1992, Hartman, et al.
CA 2088518, Feb. 10, 1993, Egbertson, et al.
US 5206373-A, (Der 93-151790/18) Apr. 27, 1993, Chung, et al.
WO 9316994, (Der 93-288324/36), Sep. 2, 1993, Chung, et al.
US 5264420-A, Nov. 23, 1993.
US 5272158, Dec. 21, 1993, Hartman, et al.
US 5281585, Jan. 25, 1994, Ihle, et al.
GB 945317 A, Mar. 17, 1994.
GB 2271567 A, Apr. 20, 1994, Hartman, et al.
US 5294616, (Der 94-0915611/11) Mar. 15, 1994, Egbertson, et al.
US 5292756, (Der 94-082364) Apr. 8, 1994, Hartman, et al.
WO 9408577, Apr. 28, 1994, Hartman, et al.
WO 9408962, Apr. 28, 1994, Hartman, et al.
WO 9409029, (Der 94-151241/18) Apr. 28, 1994, Hartman, et al.
US 5312923, May 17, 1994, Chung, et al.
HU 9400249, May 30, 1994, Gante, et al.
WO 9412181, (Der 94-199942/24), Jun. 9, 1994, Egbertson, et al.
US 5321034, June 14, 1994, Duggan, et al.
US 5334596, Aug. 2, 1994, Hartman, et al.
EP 0608759 A, Aug. 3, 1994, Gante, et al.
WO 9418981, (Der 94-293975/36) Sep. 1, 1994, Claremon, et al.
GB 2276384, (Der 94-287743/36) Sep. 28, 1994, Claremon, et al.
WO 9422825, Oct. 13, 1994, Claremon, et al.
EP 0623615A, Nov. 9, 1994, Raddatz, et al.
WO 9504531, Feb. 16, 1995, Hartman, et al. Nutt, et al., Development of Novel, Highly Selective Fibrinogen Receptor Antagonists as Potentially Useful Antithrombotic Agents, In Peptides, Chemistry and Biology, Proc. 12th Amer. Peptide Symp., J. A. Smith and J. E. Rivier, Ed., ESCOM, Leiden, 1992; 914.
Hartman, et al., J. Med. Chem., 35, 4640, 1992.
Gould, et al., Thromb. Haem., 69, 539, 1993.

Merrell Dow

WO 93/24520, May 14, 1993, Harbeson., et al.
WO 9324520, Dec. 9, 1993, Harbeson, et al.
WO 9429349, Dec. 22, 1994, Harbeson, et al.

TABLE I-continued

Nippon Steel Corp

WO 9405696, Mar. 17, 1993, Sato., et al,.
EP 628571, Dec. 14, 1994, Sato, et al.
WO 9501371, Jan. 12, 1995, Sato, et al.

ONO Pharmaceuticals

JP 05286922 (Der 93-383035/48).

Roche

EP 038,362, Feb. 19, 1990, Muller, et al..
EP 0372486, June, 13, 1990, Allig, et al.
EP 0381033, July, 8, 1990, Allig, et al.
EP 0384362, August 29, 1990, Allig, et al.
EP 0445796, Sept. 11, 1991, Allig, et al.
EP 0505868, Sept. 30, 1992, Allig, et al.
US 5273982-A, (Der 94-006713/01) Dec. 28, 1993
Alig, et al., J. Med. Chem., 35, 4393, 1992.

Rhone-Poulenc Rorer

US 4952562, Sept. 29, 1989, Klein et al.
US 5064814, (Der 91-353169/48) Apr. 5, 1990
WO 9104746, Sept. 25, 1990, Klein et al.
WO 91/05562, Oct. 10, 1989, Klein et al.
WO 91/07976, (Der 91-192965) Nov. 28, 1990, Klein et al.
WO 91/04746, Klein et al.
WO 92/18117, Apr. 11, 1991, Klein et al.
US 5086069, (Der 92-064426/08) Apr. 2, 1992.
WO 92/17196, Mar. 30, 1992, Klein et al.
US 5328900, (Der 94-221950/27) Jul. 12, 1992.
US 5332726, (Der 94-241043/29) Jul. 26, 1994.
WO 93/11759, Dec. 7, 1992, Klein et al.
EP 0577775, Jan 12, 1994, Klein, et al.
CA 2107088, Sept. 29, 1992, Klein, et al.

Sandoz

EP 0560730, Mar. 8, 1993, Kottirisch, et al.
Kottirisch, et al., Biorg. Med. Chem. Lett 3, 1675–1680, 1993.

Schering AG

EP 530937, Mar. 10, 1993, Noeski-Jungblut, et al.

Searle/Monsanto

EP 0319506, (Der 89-3195506) Dec. 2, 1988, Adams, et al.
EP 0462,960, June, 19. 1991, Tjoeng, et al.
US 4857508, Adams, et al.
EP 0502536, (Der 92-301855) Mar. 3, 1991, Garland, et al.
EP 0319506, Dec. 2, 1988, Adams et al.
US 4992463, Aug. 18, 1989.
US 5037808, Apr. 23, 1990.
EP 0454651 A2, Oct. 30, 1991, Tjoeng, et al..
US 4879313, July, 20, 1988.
WO 93/12074, Nov. 19, 1991, Abood, et al.
WO 93/12103, Dec. 11, 1991, Bovy, et al.
US 5091396, Feb. 25, 1992, Tjoeng, et al.
WO 92/15607, Mar. 5, 1992, Garland, et al.
WO 93/07867, Apr. 29, 1993, Bovy, et al.
US 888686, May 22, 1992, Bovy, et al.
CA 2099994, Sept. 7, 1992, Garland, et al.
US 5254573, Oct. 6, 1992, Bovy, et al.
(PF54C06), EP 0539343, Oct. 14, 1992, Bovy et al.
WO 93/12074, Nov. 27, 1992, Abood, et al.
WO 93/12103, Dec. 11, 1992, Bovy et al.
EP 0 539343, Apr. 28, 1993, Bovy, et al.
EP 0542708, May, 19, 1993, Bovy, et al.
WO 94/00424, June 23, 1993, Abood, et al.
WO 93/16038, Aug. 16, 1993, Miyano, et al.
WO 93US7975, Aug. 17, 1993, Zablocki, et al.
WO 93/18058, Sept. 16, 1993, Bovy, et al.
US 5254573, Oct. 19, 1993, Bovy, et al.
US, 5272162, Dec. 21, 1993, Tjoeng, et al.
EP 0574545, Dec. 22, 1993, Garland, et al.
WO 9401396, Jan. 20, 1994, Tjoeng, et al.
WO 9405694, (Der 94-101119/12) Mar. 17, 1994, Zablocki, et al.
US 5314902, May 24, 1994, Adams, et al.
WO 9418162, Aug, 18, 1994, Adams, et al.
WO 9419341, Sept. 1, 1994, Tjoeng, et al.
US 5344837, (Der 94-285503/35), Sept. 6, 1994, Zablocki, et al.
EP 614360, Sept. 14, 1994, Bovy, et al.

TABLE I-continued

| |
|---|
| WO 9420457, (Der 94-302907/37) Sept. 15, 1994, Tjoeng, et al. |
| WO 9421602, (Der 94-316876/39), Sept. 29, 1994, Tjoeng, et al. |
| WO 9422820, Oct. 13, 1994, Abood, et al. |
| EP 630366, Dec. 28, 1994, Bovy, et al. |
| US 5378727, Jan. 3, 1995, Bovy, et al. |
| Fok, et al., Int. J. Peptide Prot. Res., 38, 124–130, 1991. |
| Zablocki, et al., J. Med. Chem., 35, 4914–4917, 1992. |
| Tjoeng, et al., Peptide Mimetics of the RGD Sequence, In Peptides, Chem. and Biol. Proc. 12th Amer. Peptide Symp., J. A. Smith and J. E. Rivier, Ed., ESCOM, Leiden, 1992; 752. |
| Nicholson, et al., Thromb. Haem., 69, 975, 1993. |
| SmithKline Beecham |
| EP 341 915, Ali, et al. |
| EP 425 212, Ali, et al. |
| EP 557 406 Callahan, et al. |
| WO 93/09133, Callahan, et al. |
| WO 93/00095, Bondinell, et al. |
| WO 94/14776, Bondinell, et al. |
| WO 95/18619, Bondinell, et al. |
| WO 94/12478, Keenan, et. al. |
| WO 94/12478, Callahan, et. al. |
| WO 94/12478, Callahan, et. al |
| WO 94/12478, Samanen, et. al. |
| Sumitomo Pharm. Co. Ltd. |
| WO 9501336, June 6, 1994, Ikeda, et al. |
| Sumitomo Seiyaku KK |
| JP 06025290, (Der 94-077374/10) Feb. 1, 1994. |
| Taisho Pharm. (Teijin, Ltd) |
| JP 05230009, (Der 93-317431/40, Feb. 24, 1992. |
| JP 9235479, Feb. 24, 1992. |
| WO 94/17804, Aug. 18, 1994, Mizushima. |
| EP 634171, Jan. 18, 1995, Nizushima |
| Takeda |
| EP 0529858, Apr. 3, 1993, H. Sugihara, et al. |
| EP 606881, Jul. 20, 1994. |
| EP 614664, Sept. 14, 1994, Miyake, et al. |
| Tanabe |
| WO 89/07609, Lobl, et al. |
| WO 92/00995, July 9, 1991, Lobl, et al. |
| WO 93/08823, Nov. 6, 1991, McKenzie |
| CA 2087021, Jan 10, 1991, Lobl, et al. |
| WO 92/08464, Nov. 15, 1991, McKenzie, et al. |
| Telios/La Jolla Cancer Research |
| US. 4578079, Nov. 22, 1983, Ruoslahti, et al. |
| US. 4614517, June 17, 1985, Ruoslahti, et al. |
| US. 4792,525, June 17, 1985, Ruoslahti, et al. |
| US 4879237, (Der 90-154405/20) May, 24, 1985 |
| WO 91/15515, (Der 91-325173/44) Apr. 6, 1990 |
| US. 5041380, 1991, Ruoslahti, et al. |
| WO 95/00544 Jan. 5, 1995, Craig, et. al. |
| Cheng, et al., J. Medicin. Chem., 37, 1, 1994. |
| Collen, et al., 71, 95, 1994. |
| Temple University |
| WO 9409036, (Der 94-151248/18), Apr. 28, 1994. |
| Terumo KK |
| JP 6279389, Oct. 4, 1994, Obama, et al. |
| Karl Thomae/Boehringer Ingelheim |
| EP 0483667, May 6, 1992, Himmelsbach, et al. |
| EP 0496378, Jan. 22, 1992, Himmelsbach, et al. |
| EP 0503548, Sep. 16, 1992, Himmelsbach, et al. |
| AU A-86926/91, May 7, 1992, Himmelsbach, et al. |
| EP 0528369, Feb. 24, 1993, Austel, et al. |
| EP 0537696, Apr. 21, 1993 Linz, et al. |
| DE 4124942, Jan. 28, 1993, Himmelsbach, et al. |
| DE 4129603, Mar. 11, 1993, Pieper, et al. |
| EP 0547517 A1, (Der 93-198544) June 23, 1993, Soyka, et al. |
| EP 0567966, Nov. 3, 1993, Himmelsbach, et al. |
| EP 0567967, Nov. 3 1993, Weisenberger, et al. |
| EP 0567968, Nov. 3, 1993, Linz, et al. |

TABLE I-continued

| |
|---|
| EP 0574808, June 11, 1993, Pieper, et al. |
| Der 93-406657/51, Austel, et al. |
| EP 587134, (Der 94-085077/11) Mar. 16, 1994, Himmerlsbach, et al. |
| EP 589874, Apr. 6, 1994, Grell, et al. |
| (P534005), DE 4234295, Apr. 14, 1994, Pieper, et al. |
| EP 0592949, Apr. 20, 1994, Pieper, et al. |
| EP 596326, May, 11, 1994, Maier, et al. |
| DE 4241632, June 15, 1994, Himmelsbach, et al. |
| EP 0604800 A, Jul. 6, 1994, Himmelsbach, et al. |
| DE 4302051, (Der 94-235999/29) July, 28, 1994. |
| EP 0608858 A, Aug, 3, 1994, Linz, et al. |
| DE 4304650, (Der 94-256165/32), Aug, 18, 1994, Austel, et al. |
| EP 611660, Aug, 24, 1994, Austel, et al. |
| DE 4305388, (Der 94-264904/33), Aug. 25, 1994, Himmelsbach, et al. |
| (P5D4005), EP 612741, (Der 94-265886/33), Aug. 31, 1994, Himmelsbach, et al. |
| EP 0639575 A, Feb. 22, 1995, Linz, et al. |
| DE 4324580, Jan. 26, 1995, Linz, et al. |
| EP 0638553, Feb. 15, 1995, Himmelsbach, et al. |
| Hiummelsbach, et al., in XIIth Int. Symp. on Med. Chem. Basel, Book of Abstracts, 47, 1992. |
| Austel, et al., Natl. Mtg. Amer. Chem. Soc. Book of Abstracts, Denver, Div. Med. Chem., 1993. |
| Muller, et al., Orally Activity of BIBU 104, a Prodrug of the Non-peptide Fibrinogen Receptor Antagonist BIBU 52, in Mice and Monkeys, Thromb. Haem., 69, 975, 1993. |
| Univ. California |
| WO 94/14848, July, 7, 1994, Zanetti. |
| Univ. New York |
| WO 94/00144, June 29, 1993, Ojima, et al. |
| Yeda Res. and Dev. Co. |
| WO 93/09795, (Der 93-182236/22), Lido, et al. |
| Zeneca |
| WO 9422834, Oct. 13, 1994, Wayne, et al. |
| WO 9422835, Oct. 13, 1994, Wayne, et al. |
| EP 632016, Jan. 4, 1995, Brewster, et al. |
| EP 632019, Jan. 4, 1995, Brown, et al. |
| EP 632020, Jan. 4, 1995, Brown, et al. |

In one particular embodiment, the fibrinogen receptor antagonist template A is the fused 6/7 ring bicyclic ring defined in Bondinell, et al., WO 93/00095, published Jan. 7, 1993, as defined by sub-formula (VI):

(II)

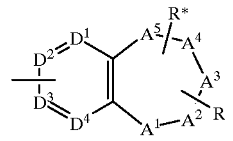

wherein $A^1$ to $A^5$ form an accessible substituted seven-membered ring, which may be saturated or unsaturated, optionally containing up to two heteroatoms chosen from the group of O, S and N wherein S and N may be optionally oxidized;

$D^1$ to $D^4$ form an accessible substituted six membered ring, optionally containing up to two nitrogen atoms;

R is at least one substituent chosen from the group of $R^7$, or Q—$C_{1-4}$alkyl, Q—$C_{2-4}$alkenyl, Q—$C_{2-4}$alkynyl, optionally substituted by one or more of =O, $R^{11}$ or $R^7$;

$R^*$ is H, Q—$C_{1-6}$alkyl, Q—$C_{1-6}$oxoalkyl, Q—$C_{2-6}$alkenyl, Q—$C_{3-4}$oxoalkenyl, Q—$C_{3-4}$oxoalkynyl, Q—$C_{2-4}$alkynyl, $C_{3-6}$cycloalkyl, Ar or Het, optionally substituted by one or more of $R^{11}$;

Q is H, $C_{3-6}$cycloalkyl, Het or Ar, $R^7$ is —$COR^8$, —$COCR'_2R^9$, —$C(S)R^8$, —$S(O)_mOR'$, —$S(O)_mNR'R''$, —RO(OR'), —$PO(OR')_2$, —$B(OR')_2$, —$NO_2$ and Tet;

$R^8$ is —OR', —NR'R'', —$NR'SO_2R'$, —NR'OR', —$OCR'_2C(O)OR'$, —$OCR'_2OC(O)$—R', —$OCR'_2C(O)NR'_2$, $CF_3$ or $AA^1$;

$R^9$ is —OR', —CN, —$S(O)_rR'$, $S(O)_mNR'_2$, —C(O)R' $C(O)NR'_2$ or —$CO_2R'$;

$R^{11}$ is H, halo, —$OR^{12}$, —CN, —$NR'R^{12}$, —$NO_2$, —$CF_3$, $CF_3S(O)_r$, —$CO_2R'$; —$CONR'_2$, Q—$C_{0-6}$alkyl-, Q—$C_{1-6}$oxoalkyl-, Q—$C_{2-6}$alkenyl-, Q—$C_{2-6}$alkynyl-, Q—$C_{0-6}$alkyloxy-, Q—$C_{0-6}$alkylamino- or Q—$C_{0-6}$alkyl-$S(O)_r$-;

$R^{12}$ is R', —C(O)R', —C(O)R', —$C(O)NR'_2$, —$C(O)OR^{15}$, —$S(O)_mR'$ or $S(O)_mNR'_2$;

$R^{13}$ is R', —$CF_3$, —SR', or —OR';

$R^{14}$ is R', C(O)R', CN, $NO_2$, $SO_2R'$ or $C(O)OR^{15}$;

$R^{15}$ is H, $C_{1-6}$alkyl or Ar—$C_{0-4}$alkyl;

R' is H, $C_{1-6}$alkyl, $C_{3-7}$cycloalkyl-$C_{0-4}$alkyl or Ar—$C_{0-4}$alkyl;

R'' is R', —C(O)R' or —$C(O)OR^{15}$;

R''' is R'' or AA2;

AA1 is an amino acid attached through its amino group and having its carboxyl group optionally protected, and AA2 is an amino acid attached through its carboxyl group, and having its amino group optionally protected;

m is 1 or 2;

n is 0 to 3;

p is 0 or 1; and t is 0 to 2; or pharmaceutically acceptable salts thereof.

With reference to formula (II), suitably, $A^1$ is $CR^1R^{1'}$, $CR^1$, $NR^1$, N, O or $S(O)_x$;

$A^2$ is $CR^2R^{2'}$, $CR^2$, $NR^2$;

$A^3$ is $CR^3R^{3'}$, $CR^3$, $NR^3$, N, O or $S(O)_x$;

$A^4$ is $CR^4R^{4'}$, $CR^4$, $NR^4$, or N;

$A^5$ is $CR^5R^{5'}$, $CR^5$, $NR^5$, N, O or $S(O)_x$;

$D^1$–$D^4$ are $CR^{11}$, $CR^6$ or N;

$R^1$ and $R^{1'}$ are $R^*$ or R, or together are ═O;

$R^2$ and $R^{2'}$ are $R^*$, R or ═O;

$R^3$ and $R^{3'}$ are $R^*$, R or ═O;

$R^4$ and $R^{4'}$ are $R^*$, R or ═O;

$R^5$ and $R^{5'}$ are $R^*$, R or ═O; and x is 0 to 2.

More suitably, $A^1$ is $CR^1R^{1'}$, $CR^1$, $NR^1$, N, O or S; $A^2$ is $CR^2R^{2'}$, $NR^2$ or $CR^2$; $A^3$ is $CR^3R^{3'}$; $A^4$ is $CR^4R^{4'}$, $CR^4$, $NR^4$, or N; $A^5$ is $CR^5R^{5'}$, $CR^5$, $NR^5$, N, O; $D^1$–$D^4$ are CH; $R^2$ or $R^4$ are R; $R^3$,$R^{3'}$ and $R^5$, $R^{5'}$ are ═O or $R^*$, H.

Preferably, $A^1$ is $CHR^1$, $CR^1$, NR'', N or S; $A^2$ is $CR^2$ or $CR^2R^{2'}$; $A^3$ is $CR^3R^{3'}$; $A^4$ is $CR^4R^{4'}$ or $NR^4$; $A^5$ is $CR^5R^{5'}$, and $D^1$–$D^4$ are CH.

In one embodiment, $A^1$ is $CR^1$, $A^2$ is $CR^2$, $A^3$ is C═O, $A^4$ is $NR^4$ and $A^5$ are $CHR^5$.

In another embodiment, $A^1$ is $NR^1$, $A^2$ is $CHCR^2$, $A^3$ is $CR^3R^{3'}$, $A^4$ is $NR^4$, and $A^5$ are C═O.

In yet another embodiment, $A^1$ and $A^4$ are C═O, $A^2$ is $NR^2$, $A^3$ is $CHR^{3'}$ and $A^5$ is $NR^5$.

In a preferred embodiment, $A^1$ is $NR^1$, $A^2$ is $CHR^2$, $A^3$ is C═O, $A^4$ is NR' and $A^5$ is $CHR^5$.

Representative sub-formulas of (II) are given by each of formulas (IIa)–(IIi) below:

(IIa)

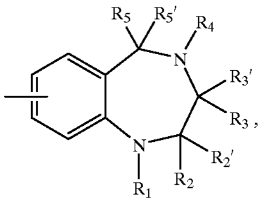

(IIb)

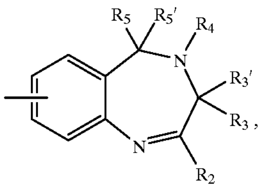

(IIc)

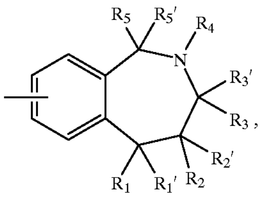

(IId)

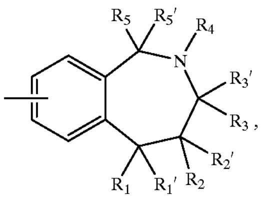

(IIe)

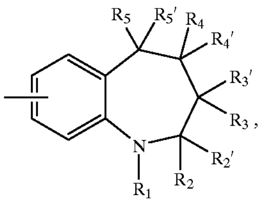

(IIf)

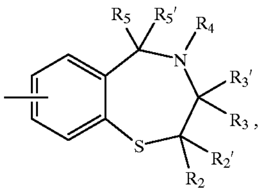

(IIg)

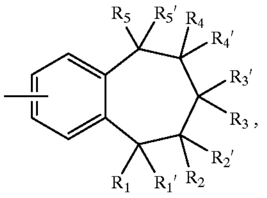

-continued (IIh)

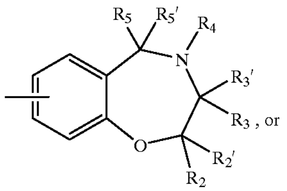

(IIi)

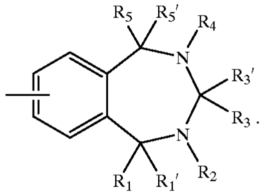

A preferred template is given by formula (III):

(III)

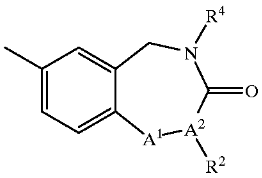

wherein $A^1$–$A^2$ is $NR^1$—CH, $NC(O)R^3$—CH, N═C, $CR^1$═C, $CHR^1$—CH, O—CH or S—CH;

$R^1$ is H, $C_{1-6}$ alkyl or benzyl;

$R^2$ is $(CH_2)_qCO_2H$;

$R^4$ is H, $C_{1-6}$alkyl, Ar—$C_{0-6}$alkyl, Het-$C_{0-6}$alkyl, or $C_{3-6}$cycloalkyl-$C_{0-6}$alkyl; and q is 1, 2 or 3.

Preferably $A^1$–$A^2$ is NH—CH and $R^2$ is $CH_2CO_2H$. Suitably, $R^3$ is methyl and W (as defined in formula (I)) is $CH_2NR'CO$. Suitably $R^i$ is substituted by NHR', CH, $CO^2H$, biotin, benzimidazole or optionally substituted phenyl.

Specific examples of vitronectin antagonists employing this template are:

(S)-2,3,4,5-Tetrahydro-4-methyl-3-oxo-7-[[[2-[2-(pyridinyl)amino]ethyl]amino]carbonyl]-1H-1,4-benzodiazepine-2-acetic acid;

(S)-2,3,4,5-Tetrahydro-4-methyl-3-oxo-7-[[[2-[(1-oxo-2-pyridinyl)amino]ethyl]amino]carbonyl]-1H-1,4-benzodiazepine-2-acetic acid;

(S)-2,3,4,5-Tetrahydro-3-oxo-7-[[[2-[2-(pyridinyl)amino]ethyl]amino]carbonyl]-1H-1,4-benzodiazepine-2-acetic acid;

(S)-2,3,4,5-Tetrahydro-3-oxo-7-[[[2-[2-(pyridinyl)amino]ethyl]amino]carbonyl]-4-(2,2,2-trifluoroethyl)-1H-1,4-benzodiazepine-2-acetic acid;

(±)-2,3,4,5-Tetrahydro-3-oxo-4-(phenylethyl)-7-[[[2-[2-(pyridinyl) amino]ethyl]amino]carbonyl]-1H-1,4-benzodiazepine-2-acetic acid;

(S)-2,3,4,5-Tetrahydro-4-methyl-7-[[[2-[2-(6-methylpyridinyl) amino]ethyl]amino]carbonyl]-3-oxo-1H-1,4-benzodiazepine-2-acetic acid;

(S)-2,3,4,5-Tetrahydro-4-methyl-3-oxo-7-[[[2- [2-(pyridinyl) amino]ethyl]methylamino]carbonyl]-1H -1,4-benzodiazepine-2-acetic acid;

(±)-2,3,4,5-Tetrahydro-4-methyl-3-oxo-7-[[[2-[2-(pyrimidinyl)amino]ethyl]amino]carbonyl]-1H-1,4-benzodiazepine-2-acetic acid;

(±)-2,3,4,5-Tetrahydro-4-methyl-7-[[2-[(6-methyl-3-pyridazinyl)amino]ethyl]amino]carbonyl]-3-oxo-1H-1,4-benzodiazepine-2-acetic acid; and (±)-2,3,4,5-Tetrahydro-4-methyl-3-oxo-7-[[2-[3-(pyridazinyl)amino]ethyl]amino]carbonyl]-1H-1,4-benzodiazepine-2-acetic acid.

A preferred compound is (S)-2,3,4,5-Tetrahydro-4-methyl-3-oxo-7-[[[2-[2-(pyridinyl) amino]ethyl]amino]carbonyl]-1H-1,4-benzodiazepine-2-acetic acid.

Another embodiment of a benzodiazepine fibrinogen receptor template a is represented by the 1,4-benzodiazepine 2,5-dione of sub-formula (IV);

(IV)

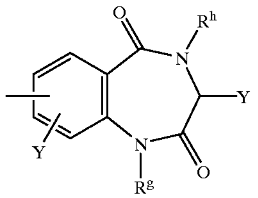

wherein:

Y is H, $C_{1-4}$alkyl, $C_{1-4}$alkoxy, $C_{1-4}$alkoxycarbonyl, F, Cl, Br, I, $CF_3$, $OR^f$, $S(O)_kR^f$, $COR^f$, $NO_2$, $N(R^f)_2$, $CO(NR^f)_2$, $CH_2N(R^f)_2$, methylenedioxy, CN, $CO_2R^f$, $OC(O)R^f$, or $NHC(O)R^f$; and $R^h$ is $(CH_2)_qCO_2R^f$.

Suitably $R^h$ is $CH_2CH_2CO_2H$ .

Entries (V)—(XV) in Table II summarize other illustrative fibrinogen receptor templates that are included within the scope of the present invention;

TABLE II (V)

A is 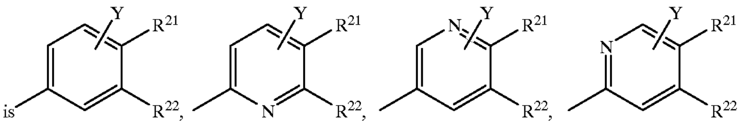

or

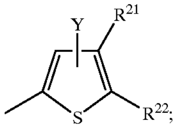

wherein:

$R^{21}$ and $R^{22}$ independently are H or —Z—$CO_2R^f$ or Z—$CON(R^f)_2$ with the proviso that one of $R^{21}$ or $R^{22}$ is —Z—$CO_2R^f$ or Z—$CON(R^f)_2$;

Z is —$CH_2$—, —$O(CH_2)_q$—, —$NR^f(CH_2)_q$—, —$S(CH_2)_q$, —$CH_2CH_2$—, —$CH(CH_3)CH_2$—, —$(CH_2)_3$—, —CH=CH—, —$C(CH_3)$=CH—, $CH_2$—CH=CH— or CH=$CHCH_2$; and Y is H, $C_{1-4}$alkyl, $C_{1-4}$alkoxy, $C_{1-4}$alkoxycarbonyl, F, Cl, Br, I, $CF_3$, $OR^f$, $S(O)_kR^f$, $COR^f$, $NO_2$, $N(R^f)_2$, $CO(NR^f)_2$, $CH_2N(R^f)_2$, methylenedioxy or Z—$COR^f$, disclosed in Alig, et al., EP 0 381 033, published Aug. 8, 1990.

(VI)

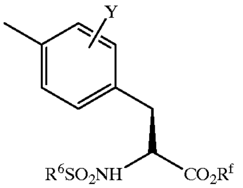

wherein:

$R^6$ is aryl, $C_{1-10}$alkyl, $C_{3-6}$cycloalkyl, $C_{4-10}$aralkyl, $C_{1-10}$alkoxyalkyl, $C_{1-10}$alkaryl, $C_{1-10}$alkylthioalkyl, $C_{1-10}$alkoxythioalkyl, $C_{1-10}$alkylamino, $C_{4-10}$aralkylamino, $C_{1-10}$alkanoylamino, $C_{4-10}$aralkanoylamino, $C_{1-10}$alkanoyl, $C_{4-10}$aralkanoyl, or $C_{1-10}$carboxyalkyl; and Y is H, $C_{1-4}$alkyl, $C_{1-4}$alkoxy, $C_{1-4}$alkoxycarbonyl, F, Cl, Br, I, $CF_3$, $OR^f$, $S(O)_kR^f$, $COR^f$, $NO_2$, $N(R^f)_2$, $CO(NR^f)_2$, $CH_2N(R^f)_2$, methylenedioxy, CN, $CO_2R^f$, $OC(O)R^f$, or $NHC(O)R^f$, disclosed in Egbertson, et al., EP 0 478 328, published Apr. 1, 1992.

(VII)

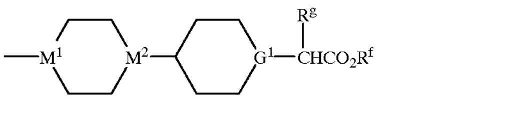

wherein:

$M^1$ is CH or N;

$M^2$ is CH or N, with the proviso that when $M^1$ is CH, $M^2$ is N; and

G' is N or N⊕R", disclosed in Eldred, et al., EP 0542 363, published May 19, 1993.

(VIII)

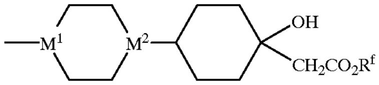

wherein:

$M^1$ is CH or N; and $M^2$ is CH or N, with the proviso that when $M^1$ is CH, $M^2$ is N, disclosed in Porter, et al., EP 0 537 980, published Apr. 21, 1993.

(IX)

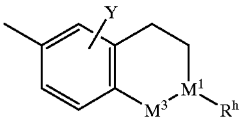

wherein:

$M^1$ is CH or N;

Y is H, $C_{1-4}$alkyl, $C_{1-4}$alkoxy, $C_{1-4}$alkoxycarbonyl, F, Cl, Br, I, $CF_3$, $OR^f$, $S(O)_kR^f$, $COR^f$, $NO_2$, $N(R^f)_2$, $CO(NR^f)_2$, $CH_2N(R^f)_2$, methylenedioxy, CN, $CO_2R^f$, $OC(O)R^f$, or $NHC(O)R^f$;

$D^3$ is $CH_2$ or C=O; and $R^h$ is $(CH_2)_qCO_2R^f$;

disclosed in Klinnick, et al., EP 0 635,492, published Jan. 25, 1995.

(X)

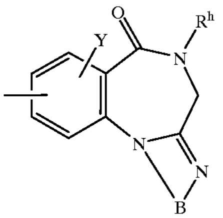

wherein:

Y is H, $C_{1-4}$alkyl, $C_{1-4}$alkoxy, $C_{1-4}$alkoxycarbonyl, F, Cl, Br, I, $CF_3$, $OR^f$, $S(O)_kR^f$, $COR^f$, $NO_2$, $N(R^f)_2$, $CO(NR^f)_2$, $CH_2N(R^f)_2$, methylenedioxy, CN, $CO_2R^f$, $OC(O)R^f$, or $NHC(O)R^f$;

$R^h$ is $(CH_2)_nCO_2R^f$; and

B is 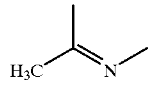, 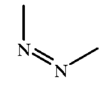, 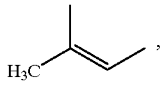, or

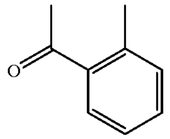

disclosed in Blackburn, et al., WO 95/04057, published Feb. 9, 1995.

(XI)

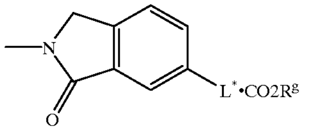

wherein:

L* is —C(O)NR$^g$—(CH$_2$)—, —C(O)—(CH$_2$)$_q$—, NR$^g$—(CH$_2$)$_q$—, —O—(CH$_2$)$_q$—, or S(O)$_k$—(CH$_2$)$_q$—, disclosed in Hartman, et al., EP 0 540 331, published May 5, 1993.

(XII)

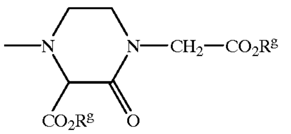

disclosed in Sugihara, et al., EP 0 529,858, published Mar. 3, 1993.

(XIII)

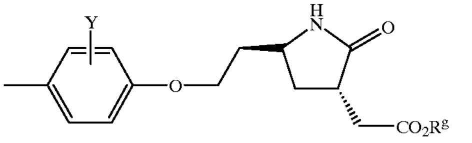

wherein:

Y is H, $C_{1-4}$alkyl, $C_{1-4}$alkoxy, $C_{1-4}$alkoxycarbonyl, F, Cl, Br, I, $CF_3$, $OR^f$, $S(O)_kR^f$, $COR^f$, $NO_2$, $N(R^f)_2$, $CO(NR^f)_2$, $CH_2N(R^f)_2$, methylenedioxy, CN, $CO_2R^f$, $OC(O)R^f$, or $NHC(O)R^f$, disclosed in Himmeisbach, et al., EP 0 483 667, published May 6, 1992.

(XIV)

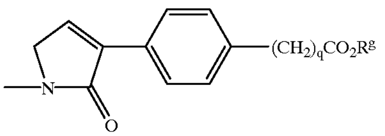

disclosed in Linz, et al., EP 0 567 968, published Nov. 3, 1993.

(XV)

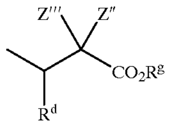

wherein:

$R^d$ is Het-$C_{0-6}$alkyl; and

Z'', Z''' independently are hydrogen, $C_{1-4}$alkyl, halo, $OR^f$, CN, $S(O)_kR^f$, $CO_2R^f$, or OH, disclosed in Bovy, et al., EP 0 539 343, published Apr. 28, 1993.

The above descriptions of fibrinogen receptor templates for use in the present invention were taken from pending published patent applications. Reference should be made to such patent applications for their full disclosures, including the variations possible for such templates and methods of preparing said templates, the entire disclosure of such patent applications being incorporated herein by reference.

In cases wherein the compounds of this invention may have one or more chiral centers, unless specified, this invention includes each unique nonracemic compound which may be synthesized and resolved by conventional techniques. In cases in which compounds have unsaturated carbon—carbon double bonds, both the cis (Z) and trans (E) isomers are within the scope of this invention. The meaning of any substituent at any one occurrence is independent of its meaning, or any other substituent's meaning, at any other occurrence.

Abbreviations and symbols commonly used in the peptide and chemical arts are used herein to describe the compounds of this invention. In general, the amino acid abbreviations follow the IUPAC-IUB Joint Commission on Biochemical Nomenclature as described in *Eur. J. Biochem.,* 158, 9 (1984).

$C_{1-4}$alkyl as applied herein means an optionally substituted alkyl group of 1 to 4 carbon atoms, and includes methyl, ethyl, n-propyl, isopropyl, n-butyl, isobutyl and t-butyl. $C_{1-6}$alkyl additionally includes pentyl, n-pentyl, isopentyl, neopentyl and hexyl and the simple aliphatic isomers thereof. $C_{0-4}$alkyl and $C_{0-6}$alkyl additionally indicates that no alkyl group need be present (e.g., that a covalent bond is present).

Any $C_{1-4}$alkyl or $C_{1-6}$alkyl, $C_{2-6}$alkenyl, $C_{2-6}$alkynyl or $C_{1-6}$oxoalkyl may be optionally substituted with the group $R^x$, which may be on any carbon atom that results in a stable structure and is available by conventional synthetic techniques. Suitable groups for $R^x$ are $C_{1-4}$alkyl, OR', SR', $C_{1-4}$alkyl, $C_{1-4}$alkylsulfonyl, $C_{1-4}$alkylsulfoxyl, —CN, $N(R')_2$, $CH_2N(R')_2$, —$NO_2$, —$CF_3$, —$CO_2R'$, —$CON(R')_2$, —CO R', —N R'C(O)R', OH, F, Cl, Br, I, $N_3$ or $CF_3S(O)_r$—, wherein r is 0 to 2 and R' is defined with respect to formula (II).

Ar, or aryl, as applied herein, means phenyl or naphthyl, or phenyl or naphthyl substituted by one to three substituents, such as those defined above for alkyl, especially $C_{1-4}$alkyl, $C_{1-4}$alkoxy, $C_{1-4}$alkthio, $CO_2H$, $N_3$, trifluoroalkyl, OH, F, Cl, Br or I.

Het, or heterocycle, indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are benzofuryl, benzimidazole, benzopyran, benzothiophene, biotin, furan, imidazole, indoline, morpholine, piperidine, piperazine, pyrrole, pyrrolidine, tetrahydropyridine, pyridine, thiazole, thiophene, quinoline, isoquinoline, and tetra- and perhydroquinoline and isoquinoline. Any accessible combination of up to three substituents on the Het ring, such as those defined above for alkyl that are available by chemical synthesis and are stable are within the scope of this invention.

$C_{3-7}$cycloalkyl refers to an optionally substituted carbocyclic system of three to seven carbon atoms, which may contain up to two unsaturated carbon—carbon bonds. Typical of $C_{3-7}$cycloalkyl are cyclopropyl, cyclobutyl, cyclopentyl, cyclopentenyl, cyclohexyl, cyclohexenyl and cycloheptyl. Any combination of up to three substituents, such as those defined above for alkyl, on the cycloalkyl ring that is available by conventional chemical synthesis and is stable, is within the scope of this invention.

The ring represented by

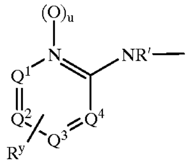

is a six-membered ring containing at least one nitrogen which is substituted in the 2 position with a nitrogen atom. The ring may optionally have an additional nitrogen atom in the ring, and hence may be a pyrazine, pyridazine or a pyrimidine. The substituent $R^y$ may be in any position on $Q^1$–$Q^4$ which results in a stable structure. It will be apparent that when the value of u is 1 the compound described will be an N-oxide; whereas, when the value of u is 0 there is no oxygen substituent on the nitrogen. A pyridine ring is preferred.

Certain radical groups are abbreviated herein. t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical, BrZ refers to the o-bromobenzyloxycarbonyl radical, ClZ refers to the o-chlorobenzyloxycarbonyl radical, Bzl refers to the benzyl radical, 4-MBzl refers to the 4-methyl benzyl radical, Me refers to methyl, Et refers to ethyl, Ac refers to acetyl, Alk refers to $C_{1-4}$alkyl, Nph refers to 1- or 2-maphthyl and CHex refers to cyclohexyl. Tet refers to 5-tetrazolyl.

Certain reagents are abbreviated herein DCC refers to dicyclohexylcarbodiimide, DMAP refers to dimethylaminopyridine, DIEA refers to diisopropylethyl amine, EDC refers to 1-(3-dimethylaminopropyl)-3-ethylcarbodiimide, hydrochloride. HOBt refers to 1-hydroxybenzotriazole, THF refers to tetrahydrofuran, DIEA refers to diisopropylethylamine, DME refers to dimethoxyethane, DMF refers to dimethylformamide, NBS refers to N-bromosuccinimide, Pd/C refers to a palladium on carbon catalyst, PPA refers to 1-propanephosphonic acid cyclic anhydride, DPPA refers to diphenylphosphoryl azide, BOP refers to benzotriazol-1-yloxy-tris(dimethylamino) phosphonium hexafluorophosphate, HF refers to hydrofluoric acid, TEA refers to triethylamine, TFA refers to trifluoroacetic acid, PCC refers to pyridinium chlorochromate.

Compounds of the formula (I) are generally prepared by reacting a compound of formula (XVI) with a compound of formula (XVII), wherein $L^1$ and $L^2$ are groups which may react to form a covalent bond in the moiety W, by methods generally known in the art.

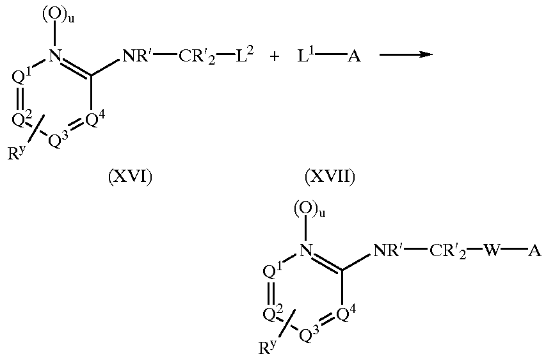

(XVI) (XVII)

(I)

Typical methods include coupling to form amide bonds, nucleophilic displacement reactions and palladium catalyzed couplings.

For instance, when W contains an ether or amine linkage, the bond may be formed by a displacement reaction, and one of $L^1$ and $L^2$ will contain an amino or hydroxy group and the other will contain a displaceable group, such as a chloro, bromo or iodo group. When W contains an amide bond, typically one of $L^1$ and $L^2$ will contain an amino group, and the other will contain a carboxylic acid group. In another approach, $L^1$ may be an aryl or heteroaryl bromide, iodide or trifluoromethylsulfonyloxy derivative and $L^2$ may contain an amino group and the amide linkage may be formed by palladium-catalyzed aminocarbonylation with carbon monoxide in a suitable solvent such as dimethylformamide or toluene.

It will be apparent that the precise identity of $L^1$ and $L^2$ will be dependent upon the site of the linkage being formed. General methods for preparing the linkage—$(CHR'')_r$—U—$(CHR'')_s$—V— are described, for example, in EP-A 0 372 486 and EP-A 0 381 033 and EP-A 0 478 363, which are incorporated herein by reference.

For instance, if V is CONH, $L^1$ may be —$NH_2$, $L^2$ may be OH (as in an acid) or Cl (as in an acid chloride). For instance, (pyrid-2-yl) aminomethyl$(CH_2)_a$—COCl may be reacted with a suitable amine. When $L^2$ is OH, a coupling agent is used.

Similarly, if V is NHCO, $L^1$ may be —$CO_2H$ or CO—Cl, $L^2$ may be —$NH_2$. For instance, (pyrid-2-yl)aminomethyl $(CH_2)_a$—NHR' may be reacted with a suitable carboxylic acid.

Where V is $NHSO_2$, $L^1$ may be $SO_2Cl$, $L^2$ may be —$NH_2$ as above. Where V is $SO_2NH$, $L^1$ may be —$NH_2$ and $L^2$ may be $SO_2Cl$. Methods to prepare such sulfonyl chlorides are disclosed, for instance, in *J. Org. Chem.,* 23, 1257 (1958).

If V is CH═CH, $L^1$ may be —CHO, $L^2$ may be CH═P—$Ph_3$. Alternately, $L^1$ may be CH═P—$Ph_3$ and $L^2$ may be CHO. For instance, (pyrid-2-yl)aminomethyl $(CH_2)_a$—CHO may be reacted with a suitable phosphorane.

Where V is $CH_2CH_2$ may be obtained by reduction of a suitably protected compound wherein V is CH═CH.

Where V is $CH_2O$, $CH_2N$ or C≡C, $L^1$ may be —OH, —NH or —C≡CH,respectively; $L^2$ may be —Br or —I. Similarly where U or V is $OCH_2$, $NR'CH_2$ or C≡C, $L^1$ may be —$CH_2Br$ and $L^2$ may be —OH, —NH or —C≡CH, respectively. For example, (pyrid-2-yl) aminomethyl$(CH_2)_a$—Br may be reacted with an appropriate amine, alkoxide or acetylene. Alternately, when U or V is C≡C, $L^1$ may be Br, I or $CF_3SO_3$, $L^2$ may be C≡CH and the coupling may be catalyzed by palladium and a base.

Compounds wherein V is $CHOHCH_2$ may be prepared from a suitably protected compound where V is CH═CH by the procedure disclosed in *J. Org. Chem.,* 54, 1354 (1989).

Compounds wherein V is $CH_2CHOH$ may be obtained from a suitably protected compound where V is CH═CH by hydroboration and basic oxidation as disclosed in *Tet. Lett.,* 31, 231 (1990).

The core 6–7 fused ring fibrinogen template of formula (II) is prepared by methods well known in the art, e.g., Hynes, et al., *J. Het. Chem.,* 1988, 25, 1173; Muller, et al., *Helv. Chim. Acta.,* 1982, 65, 2118; Mori, et al., *Heterocycles,* 1981, 16, 1491. Similarly, methods for preparing benzazepines, 1,4-benzothiazepines, 1,4-benzoxazepines and 1,4-benzodiazepines are known and are disclosed, for instance, in Bondinell, et al., International Patent Application WO 93/00095.

Representative fibrinogen antagonist templates may be prepared according to Schemes A–CC, which follow:

Scheme A describes a method of preparing exemplary fibrinogen receptor templates described in Blackburn, et. al., WO 93/08174.

Scheme A

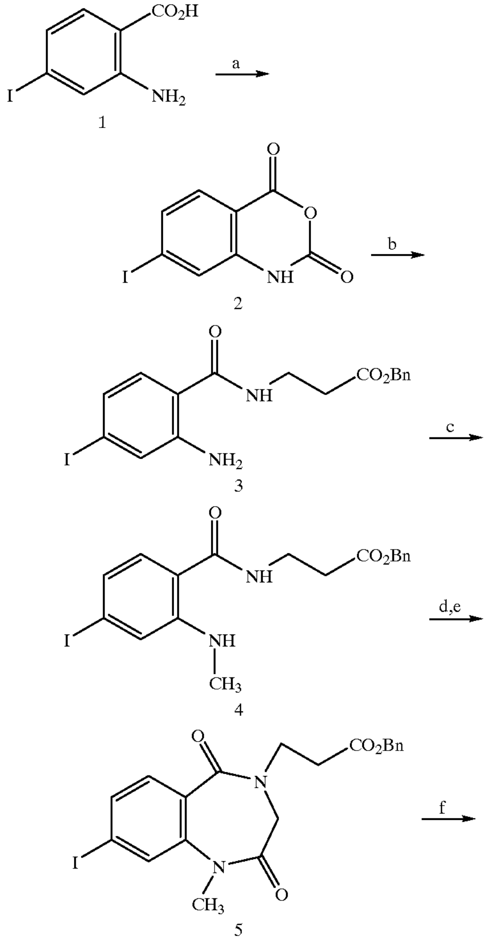

1
2
3
4
5

-continued

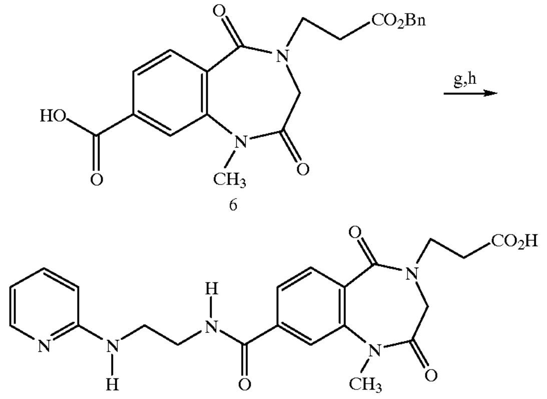

6
7 a) $COCl_2$, $Na_2CO_3$, toluene; b) β-alanine benzyl ester tosylate, DMAP, pyridine; c) $CH_3I$, 2,6-lutidine, DMF; d) α-bromoacetyl bromide, $Et_3N$, $CH_2Cl_2$; e) NaH, DMF, f) $Pd(OAc)_2$, dppf, CO, DMSO, 65° C., 18 h; g) N-(2-pyridinyl)ethylenediamine, EDC, HOBT·$H_2O$, DIEA, $CH_3CN$; h) $H_2$, 10% Pd/C, EtOH.

Scheme B describes a method of preparing exemplary fibrinogen receptor templates described in Blackburn, et. al., WO 95/04057.

Scheme B

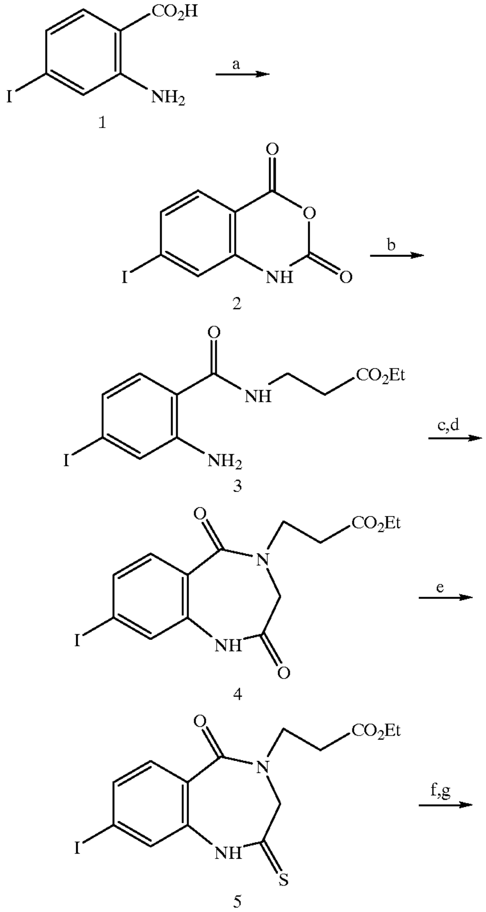

1
2
3
4
5

-continued

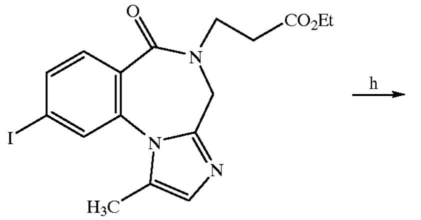

6

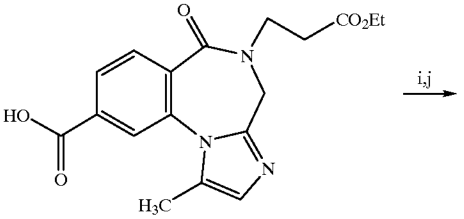

7

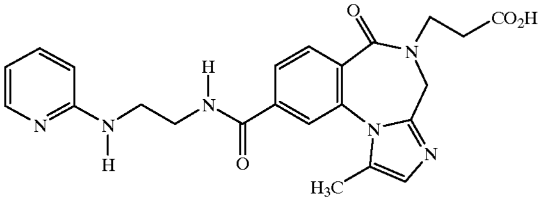

8 a) $COCl_2$, $NaHCO_3$, toluene; b) β-alanine ethyl ester hydrochloride, DMAP, pyridine; c) α-bromoacetyl bromide, $Et_3N$, $CH_2Cl_2$; d) NaH, DMF; e) Lawesson's reagent, THF, 50° C., 2 h; f) $CH_3I$, NaOH, $(n—Bu)_4N.HSO_4$, $CH_2Cl_2/H_2O$, RT, 2 h; g) propargyl amine, toluene, pyridine hydrochloride, reflux, 6 h; h) $Pd(OAc)_2$, dppf, CO, DMSO, 65° C., 18 h; i) N-(2-pyridinyl)ethylenediamine, EDC, HOBT·$H_2O$, DIEA, $CH_3CN$; j) LiOH, $H_2O$, THF, 18 h.

Scheme C describes a method of preparing exemplary fibrinogen receptor templates described in Porter, et al., EP 0542363.

a) $NaBH_3CN$, HCl, $CH_3OH$; b) HCl, dioxane, $CH_2Cl_2$; c) 1-chloro-3-[(2-pyridinyl) amino]propane, DIEA, THF; d) NaOH, $H_2O$, $CH_3OH$.

Scheme D describes a method of preparing exemplary fibrinogen receptor templates described in Porter, et al., EP 0537980.

Scheme D

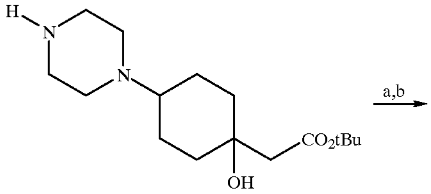

1

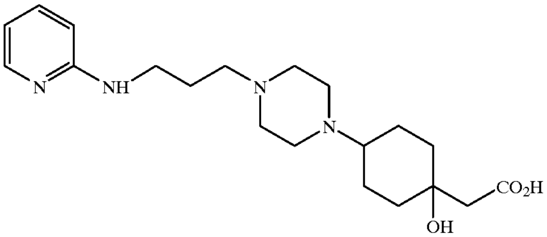

2 a) 1-chloro-3-[(2-pyridinyl)amino]propane, DIEA, THF; b) NaOH, $H_2O$, $CH_3OH$.

D-1 is alkylated with 1-chloro-3-[(2-pyridinyl)amino] propane with DIEA in THF, the resulting ester is saponified with NaOH in aqueous $CH_3OH$ to give D-2. Alternatively, the tert-butyl ester can be cleaved with TFA or HCl in a suitable solvent such as $CH_2Cl_2$ or dioxane.

Scheme E describes a method of preparing exemplary fibrinogen receptor templates described in Porter, et al., EP 0542363.

Scheme C

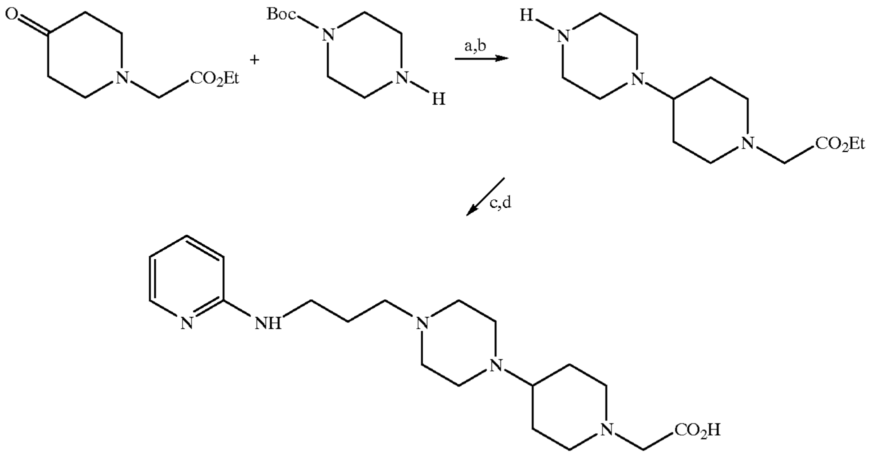

Scheme E

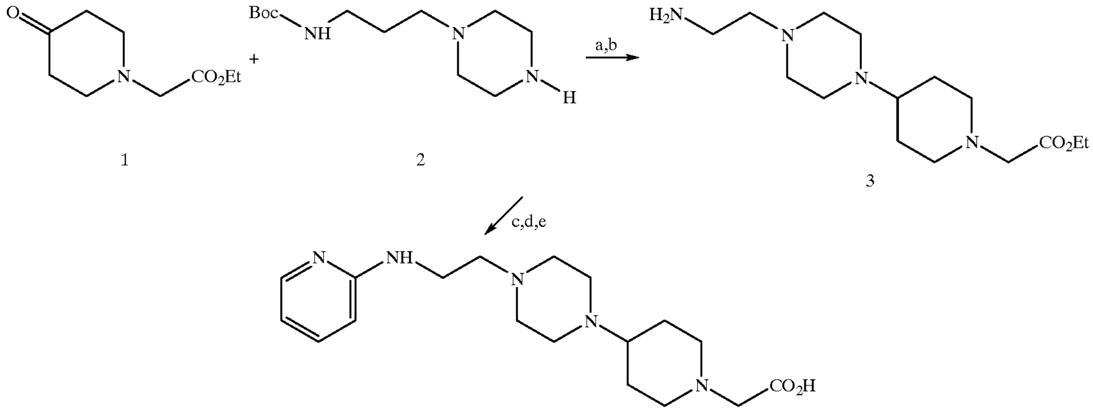

1 2 3 4 a) $NaBH_3CN$, HCl, $CH_3OH$, EtOH, molecular sieves; b) TFA, $CH_2Cl_2$; c) 2-chloropyridine-N-oxide, $NaHCO_3$, butanol; d) $HCO_2K$, 10% Pd/C, $CH_3OH$; e) 1 N NaOH, $CH_3OH$.

Reductive amination of E-1 with E-2 using NaBH3CH, HCl, and molecular sieves in $CH_3OH$ and EtOH, followed by treatment of the product with TFA in $CH_2Cl_2$ gives E-3. Treatment of E-3 with 2-chloropyridine-N-oxide and $NaHCO_3$ in butanol with heating, followed by reduction of the N-oxide with $HCO_2K$ and 10% Pd/C in $CH_3OH$, and saponification of the ethyl ester with 1 N NaOH in $CH_3OH$ gives E-4.

Scheme F describes a method of preparing exemplary fibrinogen receptor templates described in Porter, et al., EP 0537980.

Scheme F

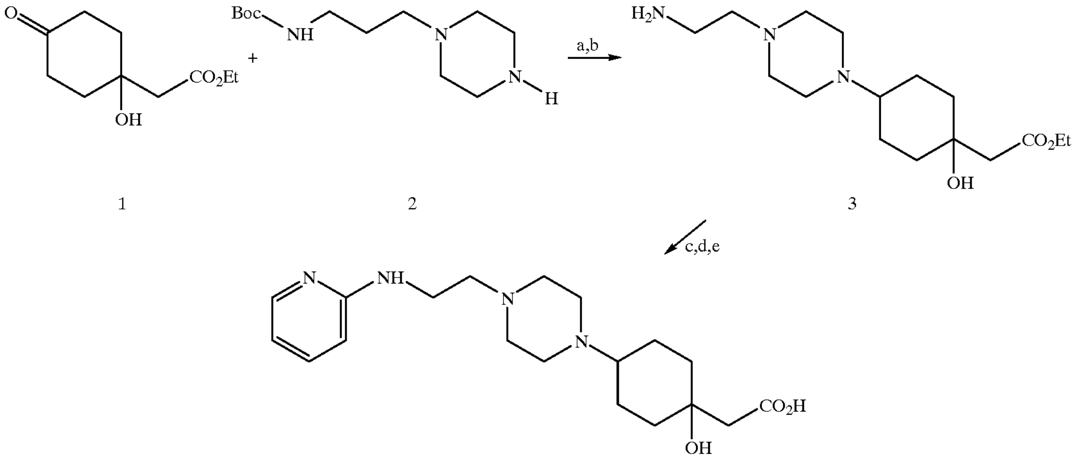

1 2 3 4 a) $NaBH_3CH$, HCl, $CH_3OH$, EtOH, molecular sieves; b) TFA, $CH_2Cl_2$; c) 2-chloropyridine-N-oxide, $NaHCO_3$, butanol; d) $HCO_2K$, 10% Pd/C, $CH_3OH$; e) 1 N NaOH, $CH_3OH$.

Reductive amination of F-1 with F-2 using NaBH3CN, HCl, and molecular sieves in $CH_3OH$ and EtOH, followed by treatment of the product with TFA in $CH_2Cl_2$ gives F-3. Treatment of E-3 with 2-chloropyridine-N-oxide and $NaHCO_3$ in butanol with heating, followed by reduction of the N-oxide with $HCO_2K$ and 10% Pd/C in $CH_3OH$, and saponification of the ethyl ester with 1 N NaOH in $CH_3OH$ gives F-4.

Scheme G describes a method of preparing exemplary fibrinogen receptor templates describes in Beavers, et al., WO 95/25091.

Scheme G

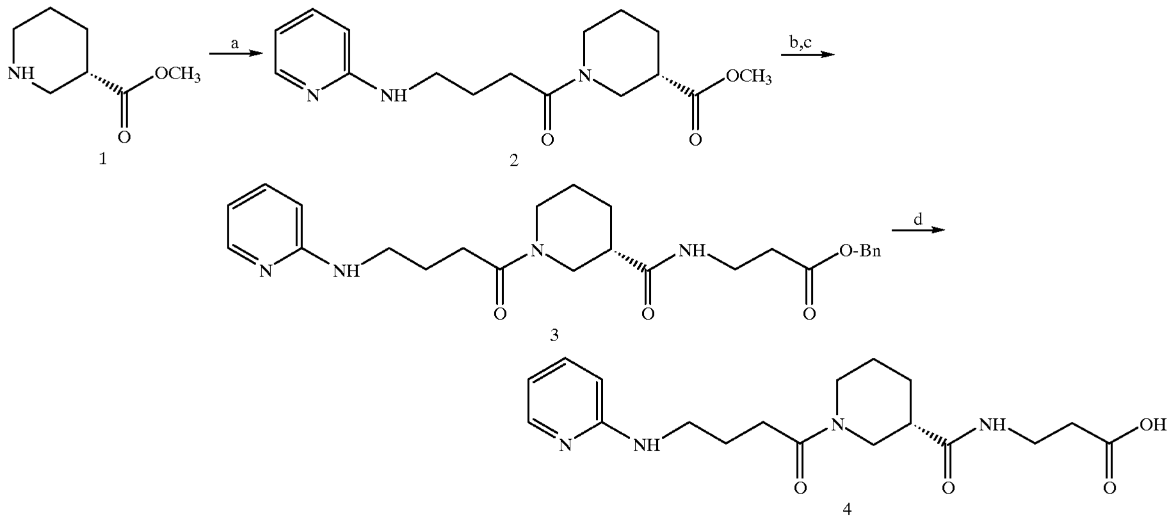

1 2 3 4 a) N-[2-(pyridinyl)amino]butyric acid, BOP—Cl, NMM, $CH_2Cl_2$; b) LiOH, $H_2O$, THF; c) β-alanine benzyl ester, EDC, HOBT, NMM, $CH_2Cl_2$; d) $H_2$, 10% Pd/C, AcOH, THF, $H_2O$.

Following the procedures of Beavers, et al., WO 95/25091, Example 1, except substituting N-[2-(pyridinyl) amino]butyric acid, for $N^{\alpha}$-Boc-D-lys(Cbz)-OH, gives F-4.

Scheme H describes a method of preparing exemplary fibrinogen receptor templates described in Hartman, et al., EP 0540334.

Scheme H

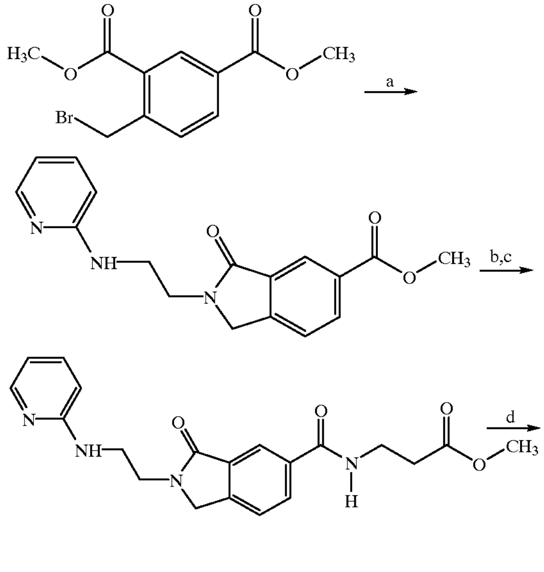

-continued

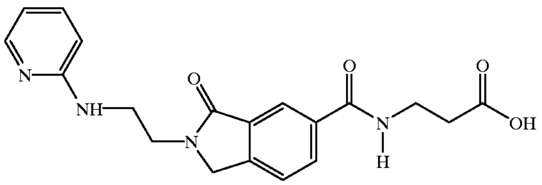

4 a) N-(2-pyridinyl)ethylenediamine, $Et_3N$, benzene; b) 1.0 N LiOH, $H_2O$, $CH_3OH$; c) β-alanine ethyl ester, BOP, $Et_3N$, $CH_3CN$; d) LiOH, $H_2O$, THF, $CH_3OH$.

Dimethyl 4-(bromomethyl)benzene-1,3-dicarboxylate, H-1, is treated with a suitably functionalized amine, such as N-(2-pyridinyl)ethylenediamine, under the general conditions described for 2,3-dihydro-N-(2-carboxy-ethyl)-2-[2-(piperidinyl)ethyl]-3-oxo-1 H-isoindole-5-carboxamide in Hartman, et al., EP 0540334, to give H-4.

Scheme I describes a method of preparing exemplary fibrinogen receptor templates described in Egbertson, et al., EP 0478363.

Scheme I

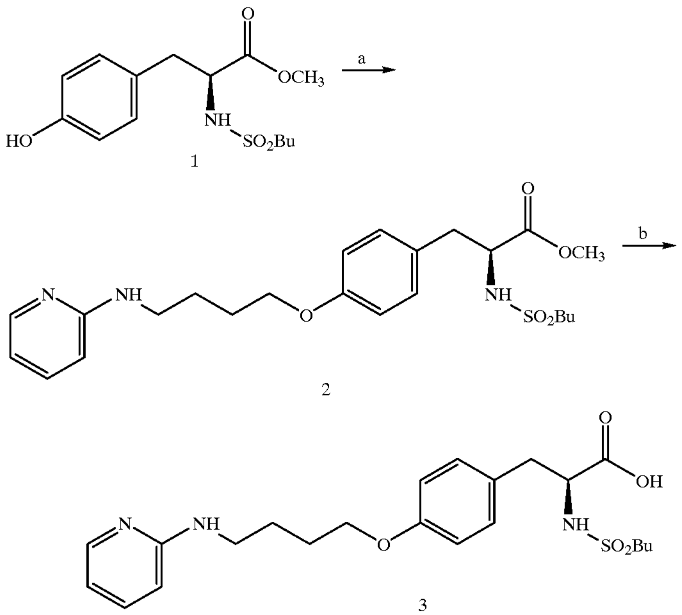

1

2

3 a) 4-[(2-pyridinyl)amino]butanol, $Ph_3P$, DEAD, $CH_2Cl_2$, benzene; b) 1.0 N LiOH, THF, $H_2O$.

N-(n-Butylsulfonyl)-L-tyrosine methyl ester, I-1, is treated with a suitably functionalized alcohol, such as 4-[(2-pyridinyl)amino]butanol, to give I-3.

Scheme J describes a method of preparing exemplary fibrinogen receptor templates described in Duggan, et al., *J. Med. Chem.* 1995, 38, 3332.

Scheme J

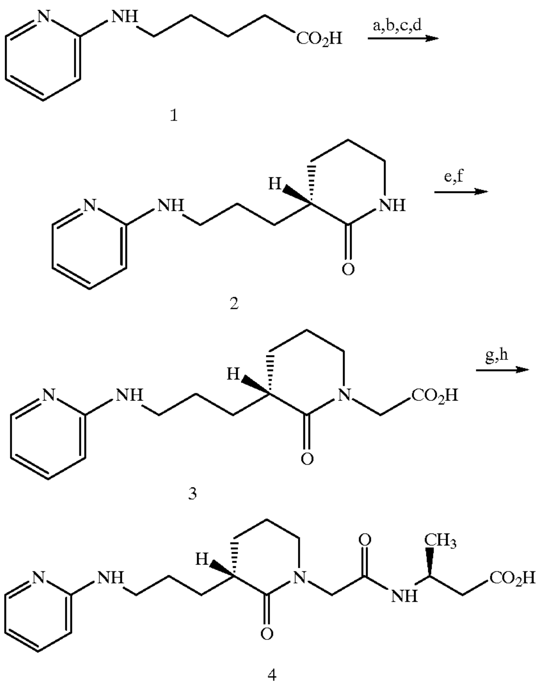

1

2

3

4 a) pivaloyl chloride, $Et_3N$, THF, (S)-4-benzyl-2-oxazolidinone; b) $Ti(O\text{-}i\text{-}Pr)Cl_2$, acrylonitrile, DIEA, $CH_2Cl_2$; c) $H_2$, $PtO_2$, $CH_3OH$, $CHCl_3$; d) $NaHCO_3$, $CH_3CN$: e) NaHMDS, ethyl bromoacetate; f) 1 N NaOH, $CH_3OH$; g) 3(R)-methyl-β-alanine ethyl ester HCl, EDC, HOBT, $Et_3N$, DMF; h) 1 N NaOH, $CH_3OH$.

A suitably functionalized carboxylic acid, such as 5-[(pyrid-2-yl)amino]pentanoic acid, J-1, is activated and reacted with a chiral auxiliary such as lithium (S)-4-benzyl-2-oxazolidinone to form a chiral Evans reagent. Alkylation of the titanium enolate with acrylonitrile, followed by nitrile reduction and lactam formation affords lactam J-2. Alkylation of the lactam with agents such as ethyl bromoacetate followed by ester saponification yields the carboxylic acid J-3. The resulting carboxylic acid derivative J-3 is converted to an activated form of the carboxylic acid using, for example, EDC and HOBt, or $SOCl_2$, and the activated form is subsequently reacted with an appropriate amine, for instance the 3(R)-methyl-β-alanine ethyl ester, in a suitable solvent such as DMF, $CH_2Cl_2$, or $CH_3CN$. Depending on whether acid neutralization is required, an added base, such as DIEA or pyridine, may be used. Many additional methods for converting a carboxylic acid to an amide are known, and can be found in standard reference books, such as "Compendium of Organic Synthetic Methods", Vol. I–VI (published by Wiley-Interscience), or Bodansky, "The Practice of Peptide Synthesis" (published by Springer-Verlag). Hydrolysis of the ethyl ester is accomplished according to the general conditions described for the conversion of J-2 to J-3, to provide the carboxylic acid J-4. Alternatively, the intermediate carboxylate salt of can be isolated, if desired, or a carboxylate salt of the free carboxylic acid can be prepared by methods well-known to those of skill in the art.

Scheme K describes a method of preparing exemplary fibrinogen receptor templates described in WO 93/07867.

Scheme K

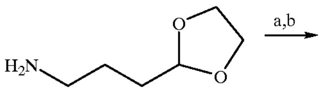

1

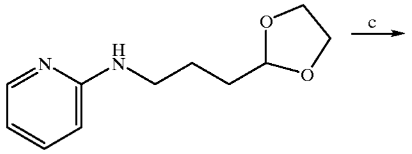

2

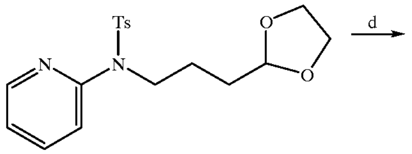

3

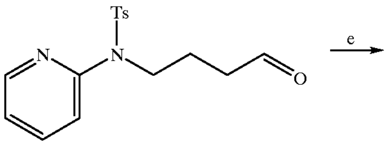

4

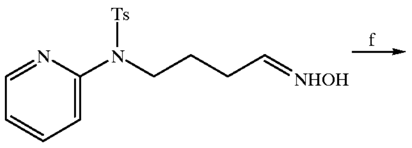

5

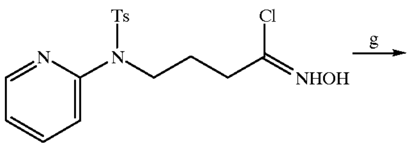

6

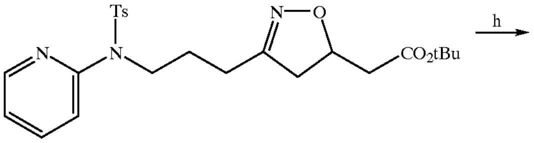

7

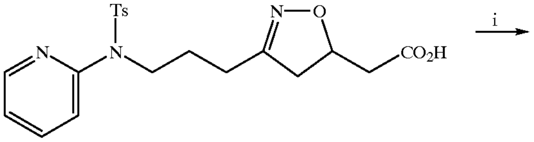

8

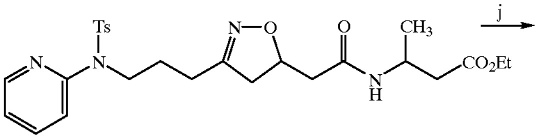

9

-continued

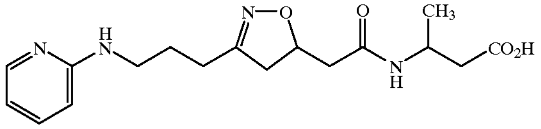

10 a) 2-chloropyridine N-oxide hydrochloride, $NaHCO_3$, tert-amyl alcohol; b) $HCO_2NH_4$, Pd/C, EtOH; c) TsCl, NaH, THF; d) p-TsOH·$H_2O$, acetone, $H_2O$; e) $NH_2OH$·HCl, NaOAc, $CH_3OH$: f) NCS, DMF; g) tert-butyl 3-butenoate, $Et_3N$; h) 4 M HCl, dioxane, $CH_2Cl_2$; i) ethyl 3-aminobutyrate, EDC, HOBt·$H_2O$, DIEA, $CH_3CN$; j) 1.0 N LiOH, THF, $H_2O$.

Readily available 2-(3-aminopropyl)-1,3-dioxolane, K-1, *Chem. Pharm. Bull.* 1982, 30, 909–914, is converted to the pyridyl derivative K-2 according to the general protocol described by Misra, *Bioorg. Med. Chem. Lett.* 1994, 4, 2165–2170. Protection of one of the nitrogen atoms of the aminopyridine moiety in K-2 can be accomplished by reaction with a sulfonyl chloride, for instance p-toluenesulfonyl chloride, in the presence of a suitable base, generally NaH or an aqueous alkali metal hydroxide, in an inert solvent, preferably THF, to afford K-3. Alternative protecting groups known to those of skill in the art may be used, as long as they are compatible with the subsequent chemistry and can be removed when desired. Such protecting groups are described in Greene, "Protective Groups in Organic Synthesis" (published by Wiley-Interscience). Removal of the dioxolanyl protecting group of K-3 to afford the aldehyde K-4 can be conveniently accomplished under mild acidic conditions, such as p-toluenesulfonic acid, in an appropriate solvent, preferably aqueous acetone. The aldehyde is converted to the aldoxime K-5 by standard procedures known to those of skill in the art, and this aldoxime is oxidized to the oximinoyl chloride derivative K-6 by the methods described in WO 95/14682 and WO 95/14683. Reaction of K-6 with an olefin, such as tert-butyl 3-butenoate (*Tet. Lett.* 1985, 26, 381–384), in the presence of a suitable base, for instance $Et_3N$ or DIEA, in an inert solvent such as benzene or toluene, according to the protocol described in WO 95/14682 and WO 95/14683, gives the cycloadduct K-7. The tert-butyl ester of K-7 is removed under standard acidic conditions, generally TFA in $CH_2Cl_2$ or HCl in dioxane, to give the carboxylic acid K-8. The carboxylic acid is activated using, for example, EDC and HOBt, or $SOCl_2$, and the activated form is subsequently reacted with an appropriate amine, for instance a suitable derivative of β-alanine, in a neutral solvent, such as DMF, $CH_2Cl_2$, or $CH_3CN$, to afford K-9. Depending on whether acid neutralization is required, an added base, such as DIEA or pyridine, may be used. Many additional methods for converting a carboxylic acid to an amide are known, and can be found in standard reference books, such as "Compendium of Organic Synthetic Methods", Vol. I–VI (published by Wiley-Interscience), or Bodansky, "The Practice of Peptide Synthesis" (published by Springer-Verlag). Derivatives of β-alanine are readily available in either racemic or optically pure form by a variety of methods known to those of skill in the art. A representative method is described in WO 93/07867. The ethyl ester and sulfonyl protecting groups of K-9 are removed using aqueous base, for example, LiOH in aqueous THF or NaOH in aqueous $CH_3OH$ or EtOH. The intermediate carboxylate salt is acidified with a suitable acid, for instance TFA or HCl, to afford the carboxylic acid K-10. Alternatively, the intermediate carboxylate salt can be isolated, if desired, or a carboxylate salt of the free carboxylic acid can be prepared by methods well-known to those of skill in the art.

Scheme L describes a method of preparing exemplary fibrinogen receptor templates described in Alig, et al., EP 0372486.

Scheme L

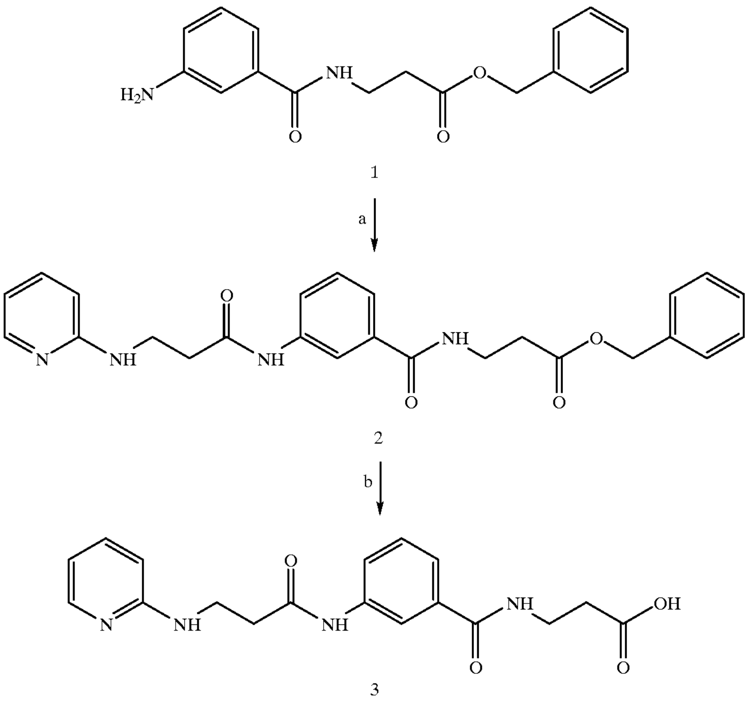

a) N-(2-pyridinyl)-β-alanine, EDC, DIEA, DMF; b) NaOH, $H_2O$, $CH_3OH$.

L-1, prepared as described in Alig et al., EP 0372486, is condensed with a suitable substituted carboxylic acid, such as N-(2-pyridinyl)-β-alanine, in the presence of EDC and DIEA, and in a suitable solvent, e.g., DMF or $CH_3CN$, to give L-2. Many additional methods for converting a carboxylic acid to an amide are known, and can be found in standard reference books, such a "Compendium of Organic Synthesis", Vol. I–VI (published by Springer-Verlag). Hydrolysis of the ester in L-2 is accomplished by saponification with a suitable reagent, e.g., NaOH, in a suitable solvent, e.g., aqueous $CH_3OH$. Alternatively, the benzyl ester in L-2 may be converted to the acid by treatment with hydrogen and a suitable catalyst, e.g., Pd/C, in a suitable solvent, e.g., $CH_3OH$, EtOH, or AcOH.

Scheme M describes a method of preparing exemplary fibrinogen receptor templates described in Alig, et al., EP 0505868.

Scheme M

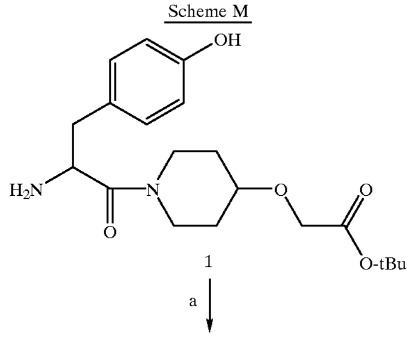

-continued

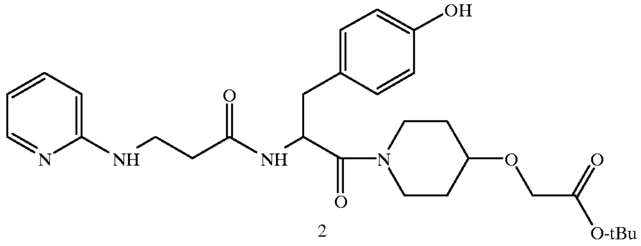

2

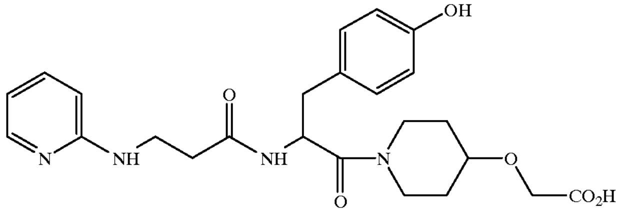

3 a) N-(2-pyridinyl)-β-alanine, EDC, DIEA, DMF; b) $CF_3CO_2H$, $CH_2Cl_2$.

M-1, prepared as described in Alig et al., EP 0505868, is condensed with a suitable substituted carboxylic acid, such as N-(2-pyridinyl)-β-alanine, in the presence of EDC and DIEA, in a suitable solvent, e.g., DMF or $CH_3CH$, to give M-2. Many additional methods for converting a carboxylic acid to an amide are known, and can be found in standard reference books, such as "Compendium of Organic Synthesis", Vol. I–VI (published by Springer-Verlag). Hydrolysis of the ester in M-2 is accomplished with trifluoroacetic acid or hydrogen chloride to give M-3. Alternatively, the ester in M-2 may be saponified with a suitable reagent, e.g., 1 N NaOH, in a suitable solvent, e.g., $CH_3OH$.

Scheme N describes a method of preparing exemplary fibrinogen receptor templates described in WO 93/07867.

Scheme N

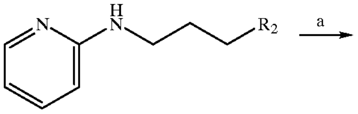

1

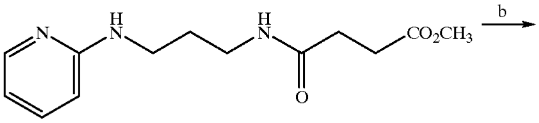

2

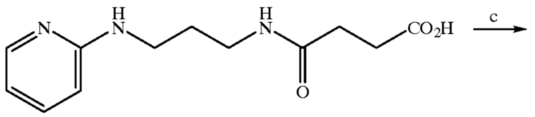

3

-continued

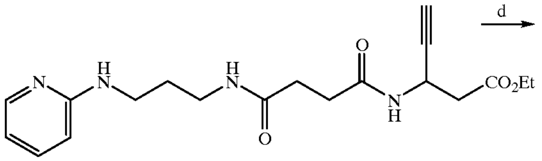

4

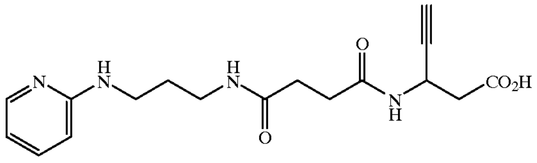

5 a) 3-(carbomethoxy)propionyl chloride, DIEA, $CH_2Cl_2$; b) 1.0 N NaOH, $CH_3OH$; c) ethyl 3-amino-4-pentynoate, EDC, HOBt·$H_2O$, DIEA, $CH_3CN$; d) 1.0 N LiOH, THF, $H_2O$.

A suitably functionalized amine, such as 2-[(3-aminoprop-1-yl)amino]pyridine, is reacted with 3-(carbomethoxy)propionyl chloride in the presence of an appropriate acid scavenger, such as $Et_3N$, DIEA, or pyridine, in a neutral solvent, generally $CH_2Cl_2$, to afford N-2. The methyl ester of N-2 is hydrolyzed using aqueous base, for example, LiOH in aqueous THF or NaOH in aqueous $CH_3OH$ or EtOH, and the intermediate carboxylate salt is acidified with a suitable acid, for instance TFA or HCl, to afford the carboxylic acid N-3. Alternatively, N-1 can be reacted with succinic anhydride in the presence of an appropriate base, such as $Et_3N$, DIEA, or pyridine, in a neutral solvent, generally $CH_2Cl_2$, to afford N-3 directly. The resulting carboxylic acid derivative N-3 is converted to an activated form of the carboxylic acid using, for example, EDC and HOBt, or $SOCl_2$, and the activated form is subsequently reacted with an appropriate amine, for instance the known ethyl 3-amino-4-pentynoate (WO 93/07867), in a suitable solvent such as DMF, $CH_2Cl_2$, or $CH_3CN$, to N-4. Depending on whether acid neutralization is required, an added base, such as DIEA or or pyridine, may be used. Many additional methods for converting a carboxylic acid to an amide are known, and can be found in standard reference books, such as "Compendium of Organic Synthetic Methods", Vol. I–VI (published by Wiley-Interscience), or Bodansky, "The Practice of Peptide Synthesis" (published by Springer-Verlag). Hydrolysis of the ethyl ester of N-4 is accomplished according to the general conditions described for the conversion of N-2 to N-3, to provide the carboxylic acid N-5. Alternatively, the intermediate carboxylate salt of can be isolated, if desired, or a carboxylate salt of the free carboxylic acid can be prepared by methods well-known to those of skill in the art.

Scheme O describes a method of preparing exemplary fibrinogen receptor templates described in Sugihara, et al., EP 0529858.

Scheme O

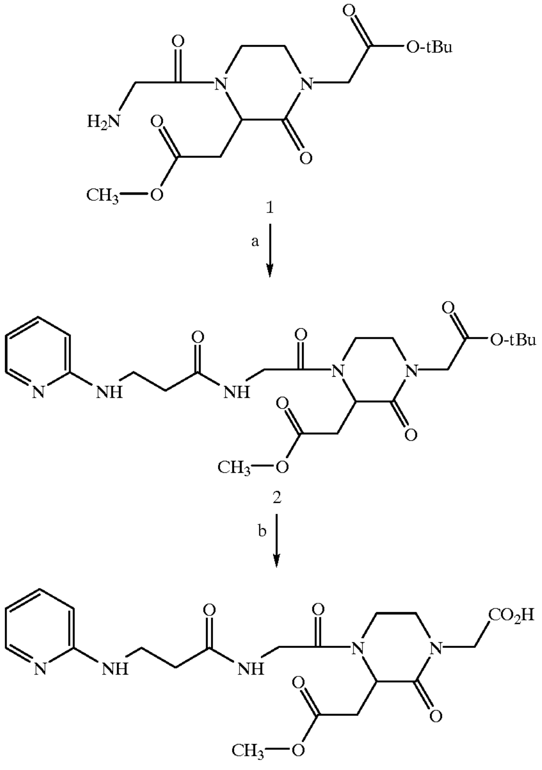

1

2

3 a) N-(2-pyridinyl)-β-alanine, EDC, DIEA, DMF; b) $CF_3CO_2H$, $CH_2Cl_2$.

O-1, prepared as described in Sugihara, et al., EP 0529858, is condensed with a suitable substituted carboxylic acid, such N-(2-pyridinyl)-β-alanine, to give O-2, and the tert-butyl ester is cleaved with TFA, following the general procedure of Sugihara, et al., Example 59, to give O-3. Many additional methods for converting a carboxylic acid to an amide are known, and can be found in standard reference books, such as "Compendium of Organic Synthesis", Vol. I–VI (published by Springer-Verlag).

Scheme P describes a method of preparing exemplary fibrinogen receptor templates described in Himmelsbach, et. al., AU-A-86926/91.

Scheme P

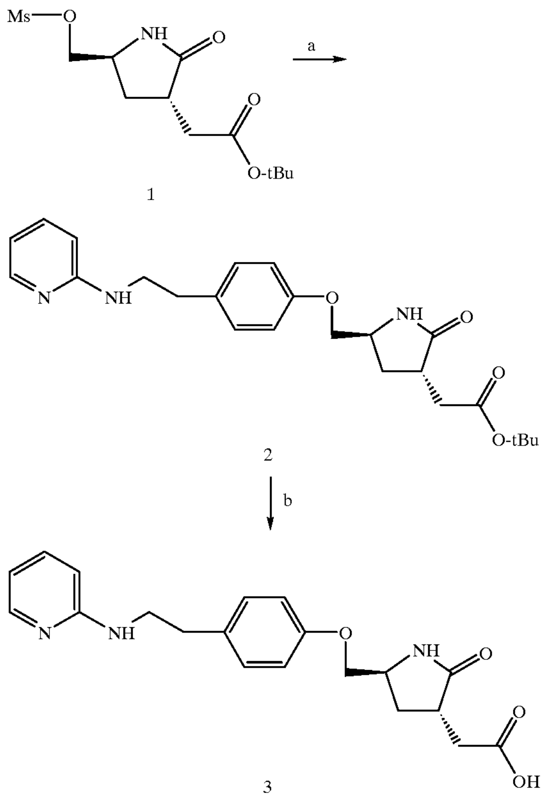

1

2

3 a) 4-[(6-amino-2-pyridinyl)methyl]phenol, $Cs_2CO_3$, DMF; b) 1 N NaOH, $CH_3OH$.

Compound P-1, prepared as described by Himmelsbach, et al., AU-A-86926/91, Example VI(28), is treated with a suitable substituted phenol, such as 4-[2-[2-(pyridinyl) amino]ethyl]phenol, following the general method of Himmelsbach et al., Example 3(51), to give P-2. The tert-butyl ester in P-2 is hydrolyzed with 1 N NaOH in $CH_3OH$ to give P-3. Alternatively, the tert-butyl ester may be cleaved with TFA or HCl in a suitable solvent such as $CH_2Cl_2$.

Scheme Q describes a method of preparing exemplary fibrinogen receptor templates described in Linz, et al., EP 0567968.

Scheme Q

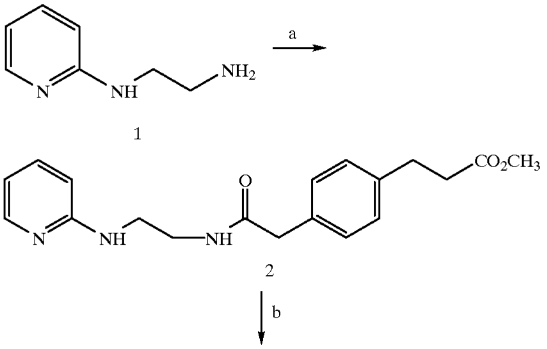

1

2

-continued

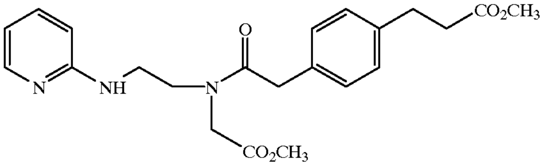

3 c,d

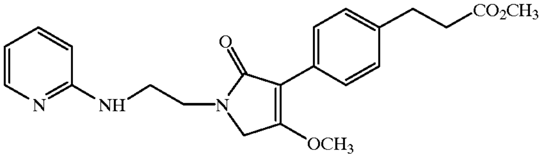

4 e

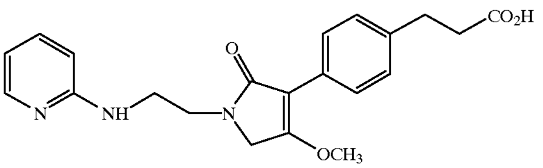

5 a) N-(2-pyridinyl)ethylenediamine, $Ph_2POCl$, $Et_3N$, DMAP, THF; b) NaH, $BrCH_2CO_2CH_3$, DMF; c) KOtBu, $CH_3I$, DMF; e) LiOH, $H_2O$, THF.

Following the procedures of Linz, et al., EP 0567968, except substituting N-(2-pyridinyl) ethylenediamine for 4-cyanoaniline, gives Q-5.

Scheme R describes a method of preparing exemplary fibrinogen receptor templates described in Wayne, et al., WO 94/22834.

Scheme R

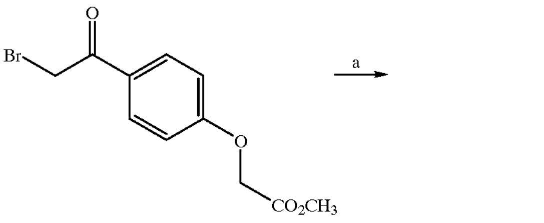

1

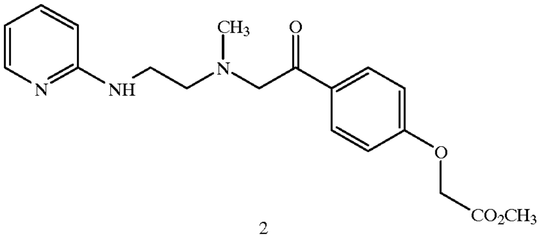

2 b

-continued

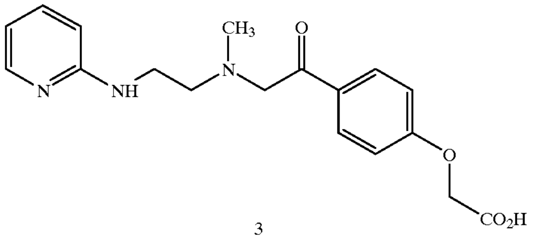

3 a) N-methyl-N'-(2-pyridinyl)ethylenediamine, $CH_3CN$; b) 1 N NaOH, $CH_3OH$

Following the procedures of Wayne, et al., WO 94/22834, Example 1–2, except substituting N-methyl-N'-(2-pyridinyl) ethylenediamine for 1-(4-pyridyl)piperazine gives R-3.

Scheme S describes a method of preparing exemplary fibrinogen receptor templates described in Wayne, et al., WO 94/22834.

Scheme S

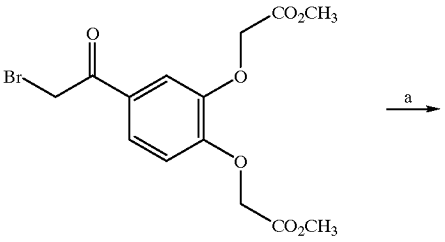

1

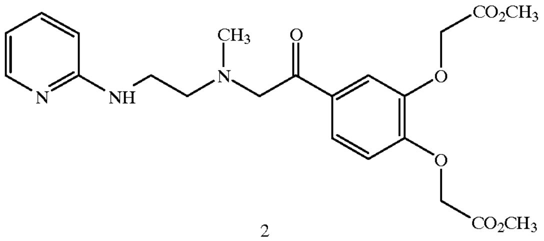

2 b

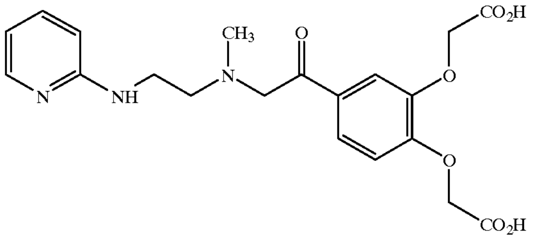

3 a) N-methyl-N'-(2-pyridinyl)ethylenediamine, $CH_3CN$; b) 1 N NaOH, $CH_3OH$

Following the procedures of Wayne, et al., WO 94/22834, Example 3–4, except substituting N-methyl-N'-(2-pyridinyl) ethylenediamine for 1-(4-pyridyl)piperazine gives S-3.

Scheme T describes a method of preparing exemplary fibrinogen receptor templates described in Alig, et al., EP 0381033.

Scheme T

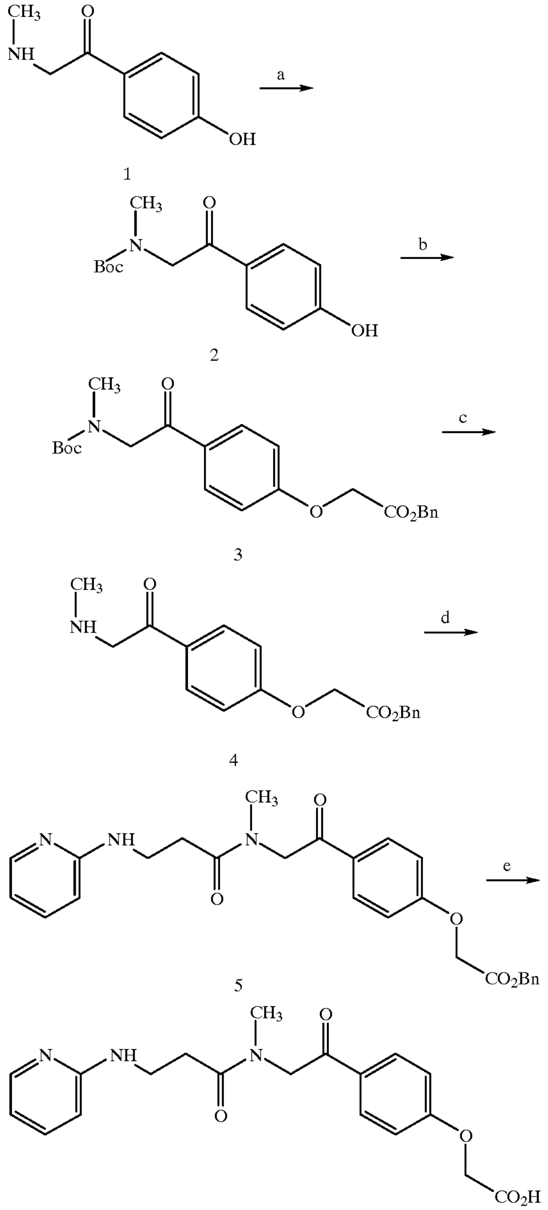

1 2 3 4 5 6 a) $(Boc)_2O$, NaOH, dioxane, $H_2O$; b) $BrCH_2CO_2Bn$, $K_2CO_3$, acetone; c) 4M HCl, dioxane; d) N-(2-pyridinyl)-β-alanine, EDC, DIEA, DMF; e) 1 N NaOH, $CH_3OH$.

T-1 is treated with di-tert-butyl dicarbonate and sodium hydroxide in aqueous dioxane to afford T-2, which is alkylated on the phenolic oxygen with benzyl bromoacetate and potassium carbonate in acetone to give T-3. The Boc group in T-3 is removed with hydrogen chloride in dioxane, and the resulting T-4 is acylated on nitrogen with N-(2-pyridinyl)-β-alanine, EDC and DIEA in DMF to give T-F. The benzyl ester in T-5 is saponified to give T-6. Alternatively, the benzyl ester may be cleaved by treatment with $H_2$ and a suitable catalyst, such as Pd/C, in a suitable solvent, such as $CH_3OH$, EtOH, or AcOH.

Scheme U describes a method of preparing exemplary fibrinogen receptor templates described in Alig, et al., EP 0381033.

Scheme U

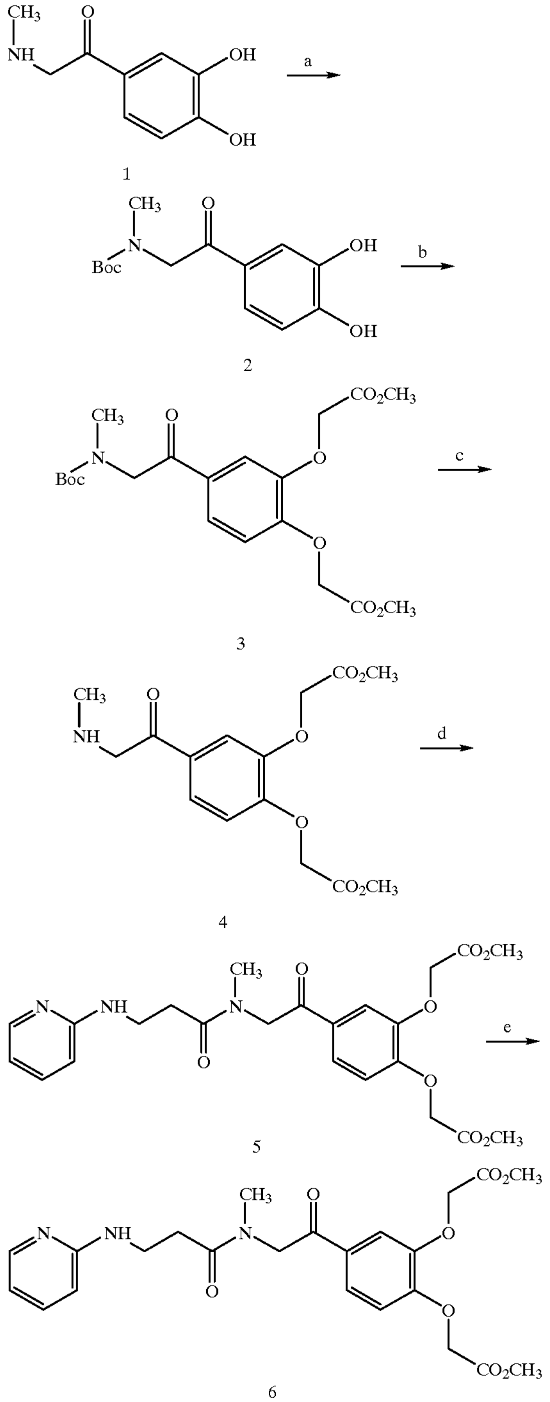

1 2 3 4 5 6 a) $(Boc)_2O$, NaOH, dioxane, $H_2O$; b) $BrCH_2CO_2CH_3$, $K_2CO_3$, acetone; c) 4M HCl, dioxane; d) N-(2-pyridinyl)-β-alanine, EDC, DIEA, DMF; e) 1N NaOH, $CH_3OH$.

U-1 is treated with di-tert-butyl dicarbonate and sodium hydroxide in aqueous dioxane to afford U-2, which is alkylated on the phenolic oxygens with methyl bromoacetate and potassium carbonate in acetone to give U-3. The Boc group in U-3 is removed with hydrogen chloride in dioxane, and the resulting U-4 is acylated on nitrogen with N-(2-pyridinyl)-β-alanine, EDC and DIEA in DMF to give U-5.

The methyl esters in U-5 are cleaved by treatment with 1M NaOH in $CH_3OH$ to give U-6.

Scheme V describes a method of preparing exemplary fibrinogen receptor templates described in Himmelsbach, et al., EP 0587134.

Scheme V

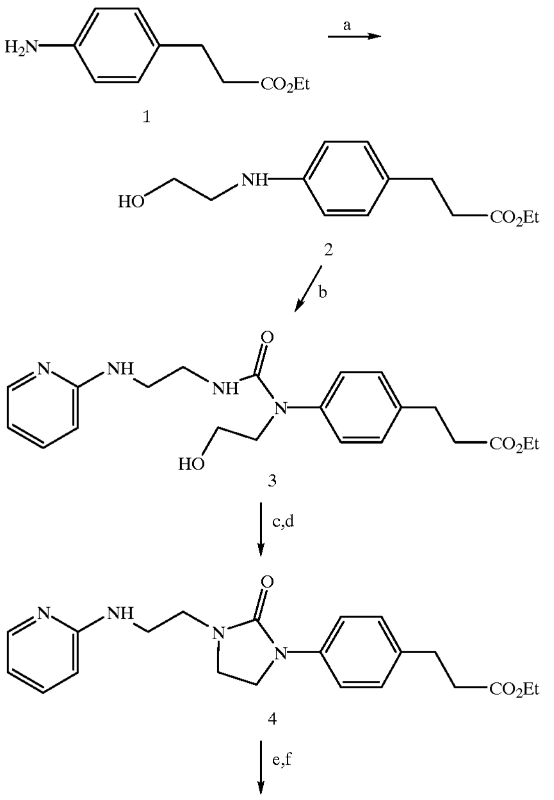

-continued

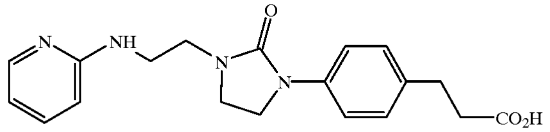

5 a) glycolaldehyde dimer, $NaBH_3CN$, $H_2O$, $CH_3CN$, pH 6–7; b) N-(2-pyridinyl)ethylenediamine, $COCl_2$; c) $CH_3SO_2Cl$, $Et_3N$, $CH_2Cl_2$; d) NaI, $KN(TMS)_2$ THF, acetone, reflux; e) $NH_2NH_2$ $H_2O$; f) 1 N NaOH, EtOH.

Scheme V provides a method for the preparation of 2-oxo-imidazolidine compounds, e.g., V-5, wherein reductive amination of an amine, for example V-1, with glycolaldehyde dimer and sodium cyanoborohydride, gives a secondary amine, such as V-2. A primary amine, as exemplified by N-(2-pyridinyl)ethylenediamine, is treated with phosgene to give an isocyanate, which is allowed to react, without isolation, with the secondary hydroxyethylamine to give a hydroxyethylurea, as exemplified by compound V-3. The hydroxyl group is converted into a leaving group, such as a methanesulfonate or iodide, and is allowed to cyclize to a 2-oxo-imidazolidine, V-4, employing methods known in the art, Himmelsbach, et al., EP 0587134, such as treating the hydroxyethylurea 4 with trifluorosulfonyl chloride and $Et_3N$, followed by NaI and then potassium bis (trimethylsilyl)azide, as described in Himmelsbach, et al., EP 0587134, Example III. Treatment of V-4 with hydrazine and saponification of the ester give V-5.

Scheme W provides a method for the preparation of 1,2,3,4-tetrahydroisoquinoline compounds as exemplary fibrinogen receptor antagonists, as described in M. J. Fisher et al., EP 0635492.

Scheme W

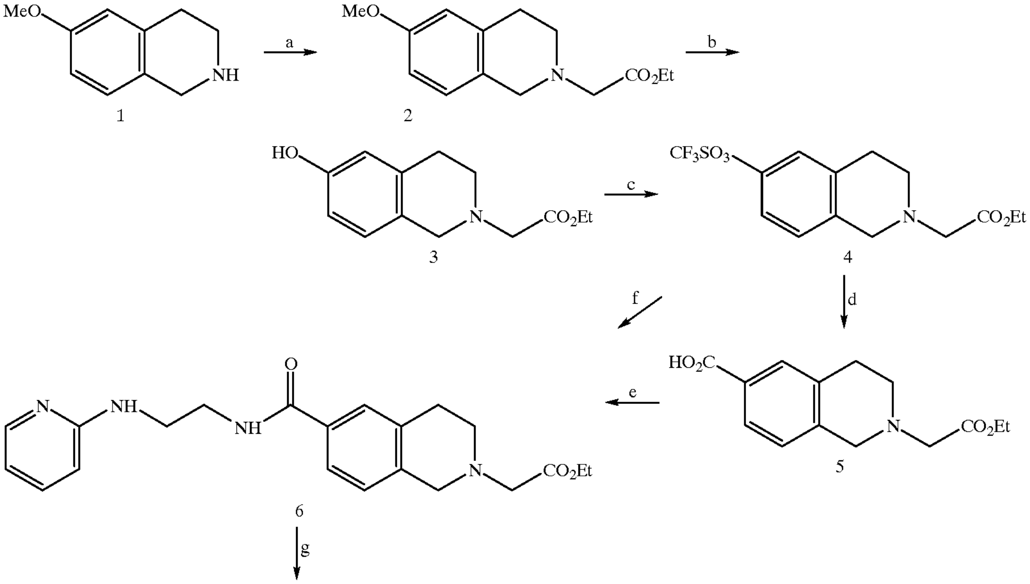

-continued

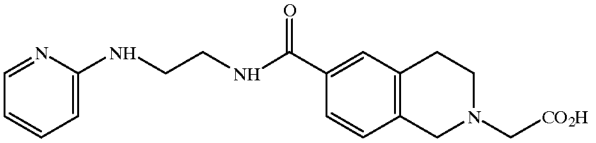

7 a) $ClCH_2CO_2Et$, $Et_3N$, DMF; b) $BBr_3$, $CH_2Cl_2$; c) $(CF_3SO_2)_2O$, pyridine; d) CO, $Pd(OAc)_2$, $PPh_3$, DIEA, NMP, $NH_4HCO_3$, $H_2O$; e) N-(2-pyridinyl)ethylenediamine, EDC, HOBt, DIEA, DMF; f) N-(2-pyridinyl)ethylenediamine, CO, $Pd(OAc)_2$, $PPh_3$, DIEA, NMP, $NH_4HCO_3$, $H_2O$; g) 1N NaOH, EtOH.

Accordingly, a 6-methoxy-3,4-dihydroisoquinoline, such as compound W-1 is prepared by the method described by D. J. Sall and G. L. Grunewald, *J. Med. Chem.* 1987, 30, 2208–2216. The isoquinoline is treated with a haloacetic acid ester in the presence of a tertiary amine to afford the 2-acetic acid ester, as exemplified by compound W-2. The 6-methoxy compound is converted into the corresponding 6-hydroxy compound by methods known in the art, for exemplified by N-(2-pyridinyl)ethylenediamine, employing a standard amide bond forming reagent to give the desired amide, such as compound W-6. Saponification affords the title compound of Example W, W-7. Alternatively, the palladium-catalyzed carbonylation reaction with the triflate, exemplified by compound W-4, may be trapped with N-(2-pyridinyl)ethylenediamine to provide, after saponification, W-7.

Scheme X provides a method for the preparation of 3,4-dihydroisoquinolin-1-one compounds as exemplary fibrinogen receptor antagonists, as described M. J. Fisher et al., EP 0635492.

Scheme X

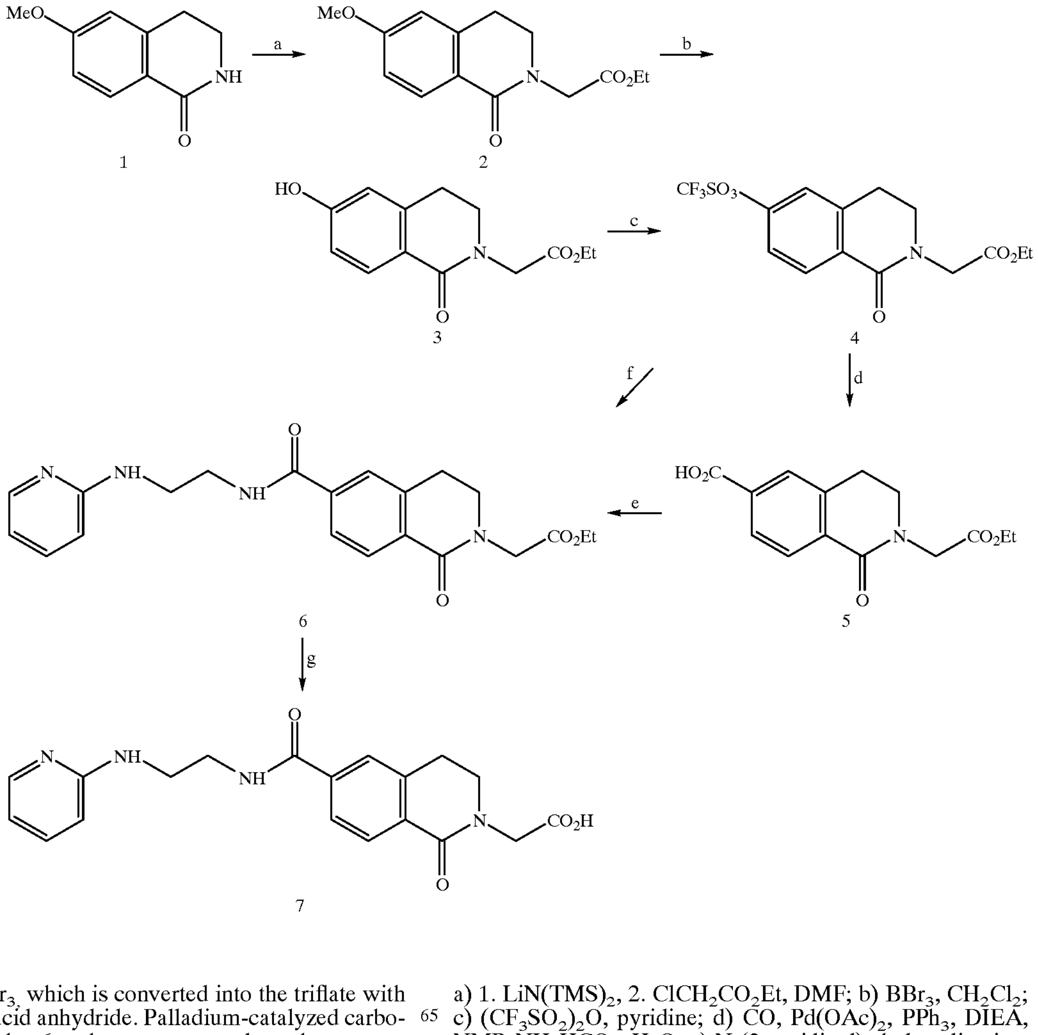

example with $BBr_3$ which is converted into the triflate with trifluorosulfonic acid anhydride. Palladium-catalyzed carbonylation affords the 6-carboxy compound, such as compound W-5, which is then condensed with an amine, as a) 1. $LiN(TMS)_2$, 2. $ClCH_2CO_2Et$, DMF; b) $BBr_3$, $CH_2Cl_2$; c) $(CF_3SO_2)_2O$, pyridine; d) CO, $Pd(OAc)_2$, $PPh_3$, DIEA, NMP, $NH_4HCO_3$, $H_2O$; e) N-(2-pyridinyl)ethylenediamine, EDC, HOBt, DIEA, DMF; f) N-(2-pyridinyl)

ethylenediamine, CO, $Pd(OAc)_2$, $PPh_3$, DIEA, NMP, $NH_4HCO_3$, $H_2O$; g) 1N NaOH, EtOH.

Accordingly, the 1-oxo compound X-1, prepared by the method described by D. J. Sall and G. L. Grunewald, *J. Med. Chem.* 1987, 30, 2208–2216, is treated with a base, such as $LiN(TMS)_2$, and a haloacetic acid ester to give a 2-acetic acid ester, as exemplified by compound X-2. The 1-oxo compound is then employed in the analogous series of reactions deployed in Scheme U, substituting the corresponding 1-oxo analog, as shown in Scheme U, to provide the title compound of Example X, X-7. As in Scheme U, alternatively, the palladium-catalyzed carbonylation reaction with the triflate, exemplified by compound X-4, may be trapped with an amine, as exemplified by N-(2-pyridinyl) ethylenediamine, provides, after saponification, the amide exemplified by the title compound of Example X, X-7.

Accordingly, a 6-amino-2-tert-butyloxycarbonyl-tetral-1-one, exemplified by compound Y-1, which is prepared according to the methods described in M. J. Fisher et al., EP 0635492, is condensed with an activated derivative of a carboxylic acid obtained N-(2-pyridinyl)-β-alanine to provide, after deesterification, the amide Y-2.

Scheme Z provides a method for the preparation of 6-aminoacyltetralin compounds as exemplary fibrinogen receptor antagonists, as described M. J. Fisher et a., EP 0635492.

Scheme Z

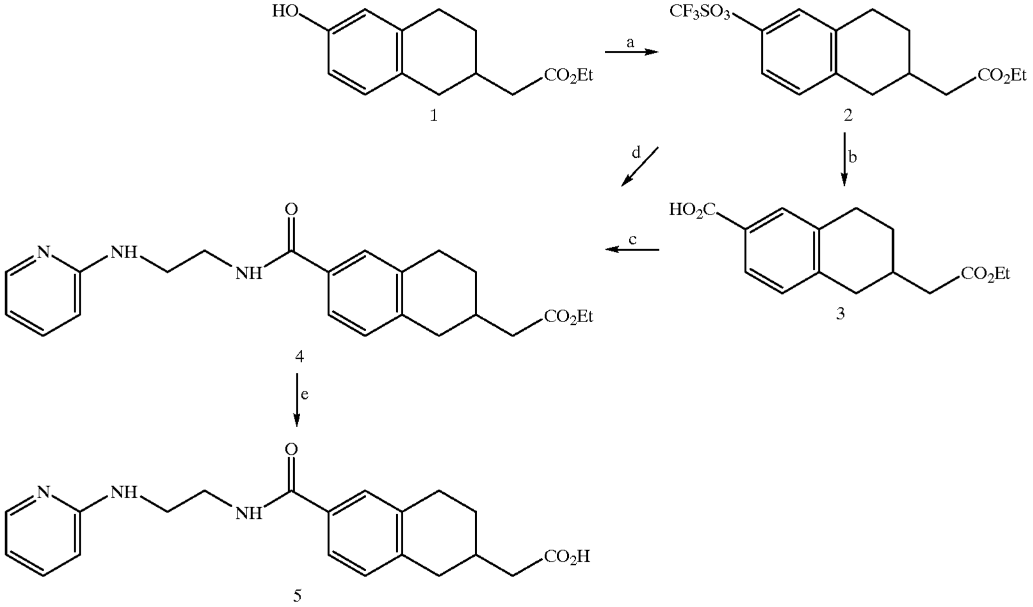

Scheme Y provides a method for the preparation of 6-acylaminotetraline compounds as exemplary fibrinogen receptor antagonists, as described M. J. Fisher et al., EP 0635492.

Scheme Y

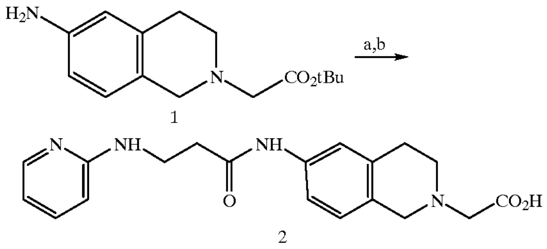

a) N-(2-pyridinyl)-β-alanine, EDC, HOBt, DIEA, DMF; b) TFA, $CH_2Cl_2$.

a) $(CF_3SO_2)O$, pyridine; b) CO, $Pd(OAc)_2$, $PPh_3$, DIEA, NMP, $NH_4HCO_3$, $H_2O$; c) N-(2-pyridinyl)ethylenediamine, EDC, HOBt, DIEA, DMF; d) N-(2-pyridinyl) ethylenediamine, CO, $Pd(OAc)_2$, $PPh_3$, DIEA, NMP, $NH_4HCO_3$, $H_2O$; e) 1N NaOH, EtOH.

Accordingly, an ethoxycarbonylmethyl-6-hydroxy-tetral-1-one, exemplified by compound Z-1, which is prepared according to the methods described in M. J. Fisher et al., EP 0635492, is treated with triflic anhydride to provide the triflate, as exemplified by compound Z-2, which is employed in a palladium-catalyzed carbonylation reaction to afford a carboxylic acid, such as compound Z-3, which is then condensed with an amine such as N-(2-pyridinyl) ethylenediamine to provide, after deesterification, the 6-aminoacyl compound exemplified by Example Z, Z-5. Alternatively, the palladium-catalyzed carbonylation reaction with the triflate exemplified by compound Z-2, may be trapped with N-(2-pyridinyl)ethylenediamine to provide, after saponification, the corresponding 6-aminoacyl compound exemplified by Example Z, Z-5.

Scheme AA provides a method for the preparation of 5-acylaminobenzofuran and 5-acylaminodihydrobenzofuran compounds as exemplary fibrinogen receptor antagonists, as described in M. L. Denney, et al., EP 0655439.

Scheme AA

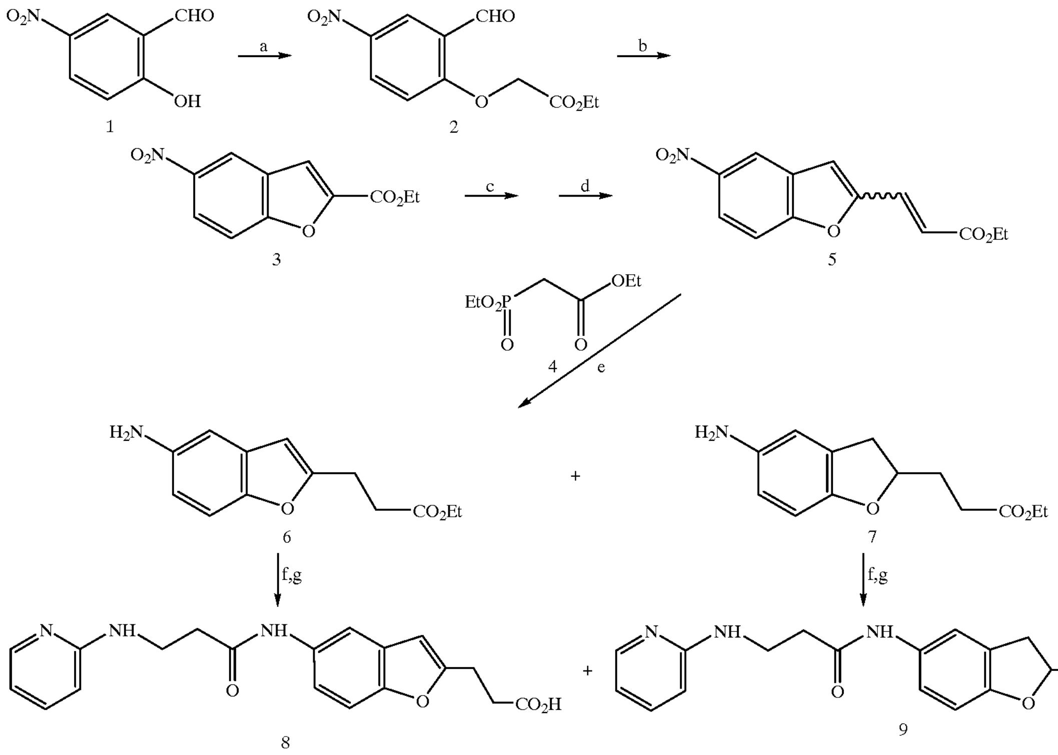

a) $BrCH_2CO_2Et$, $K_2CO_3$, NaI, THF; b) 1. DBU, EtOH, 2. HCl, EtOH; c) DiBAL, −78° C., THF; d) NaH, THF; e) $H_2$, 10% Pd/C, EtOH; f) N-(2-pyridinyl)-β-alanine, EDC, HOBT, $Et_3N$, DMF; g) 1N NaOH, $CH_3OH$.

Accordingly, a 5-nitrosalicylaldehyde, exemplified by compound AA-1, is treated with a haloacetic acid ester to give the phenoxyacetic acid ester, exemplified by compound AA-2. A 2-alkoxycarbonylfuran, exemplified by compound AA-3, is obtained by treating the aldehyde with base, for example with DBU. The 2-alkoxycarbonyl group is reduced to the aldehyde, for example with DiBAL. Wittig reaction affords the 2-acrylate ester, exemplified by compound AA-5, which is reduced to the benzofuran-2-propionic acid ester, exemplified by compound AA-6 and the dihydrobenzofuran-2-propionic acid ester, exemplified by compound AA-7. The amine AA-6 is then condensed with an activated derivative of a carboxylic acid, such as N-(2-pyridinyl)-β-alanine, to provide, after deesterification, the amide exemplified by the title compound of Example AA, AA-8. Alternatively, the amine AA-7 is condensed with an activated derivative of a carboxylic acid, such as N-(2-pyridinyl)-β-alanine, to provide, after deesterification, the amide exemplified by AA-9.

Schemes BB-1, BB-2 and BB-3 provide a method for the preparation of 5-aminoacylbenzofuran and 5-aminoacyldihydrobenzofuran compounds as exemplary fibrinogen receptor antagonists, as described in M. L. Denney, et al., EP 0655439.

Scheme BB-1

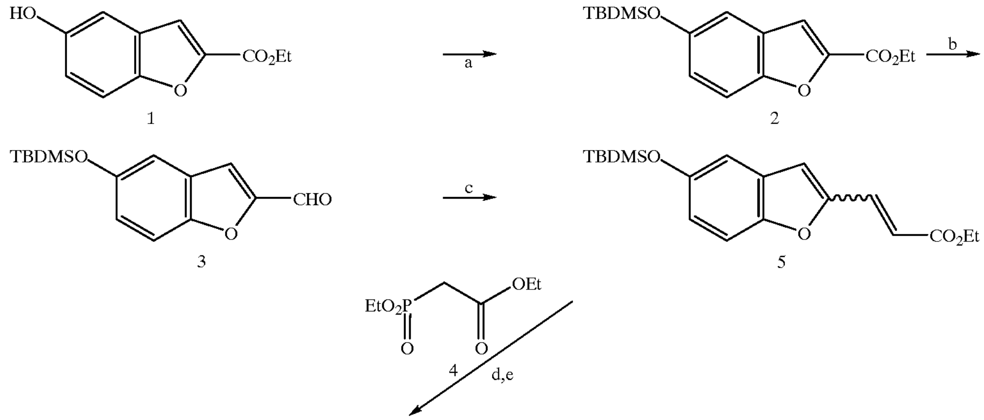

-continued
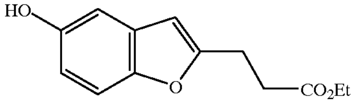
6
+
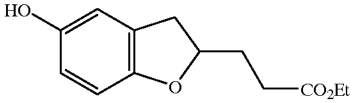
7
a) TBDMS—Cl, imidazole, THF; b)DiBAL, −78° C., THF; c) NaH, THF; d) $H_2$, 5% Pd/C, EtOH; e) $Et_4NF$, THF.
Scheme BB-2
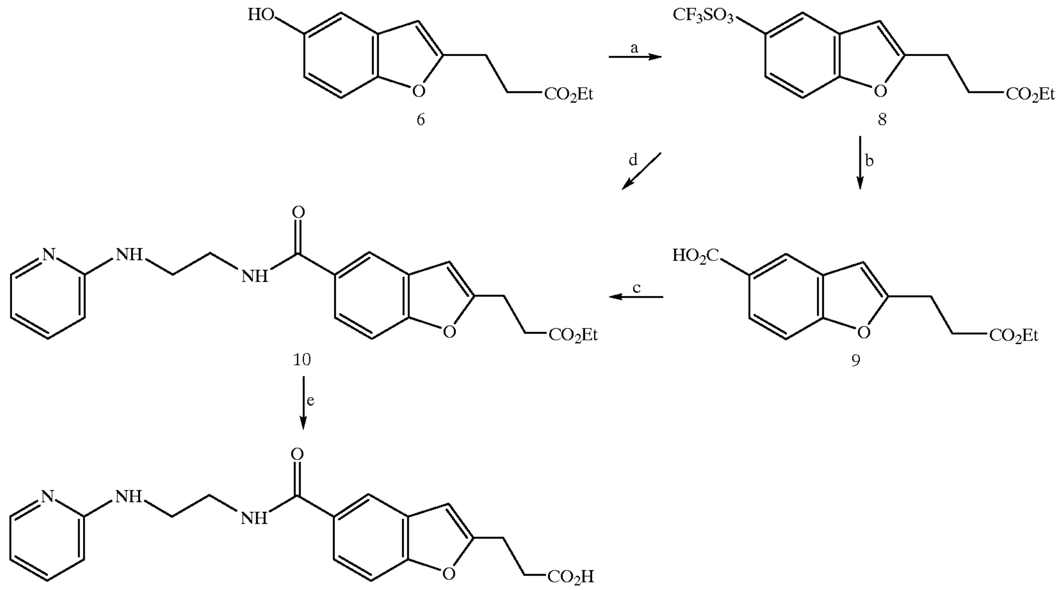
6, 8, 9, 10, 11
a) $(CF_3SO_2)_2O$, pyridine; b) CO, $Pd(OAc)_2$, $PPh_3$, DIEA, NMP, $NH_4HCO_3$, $H_2O$; c) N-(2-pyridinyl)ethylenediamine, EDC, HOBt, DIEA, DMF; d) N-(2-pyridinyl) ethylenediamine, CO, $Pd(OAc)_2$, $PPh_3$, DIEA, NMP, $NH_4HCO_3$, $H_2O$ e) 1N NaOH, EtOH.
Scheme BB-3
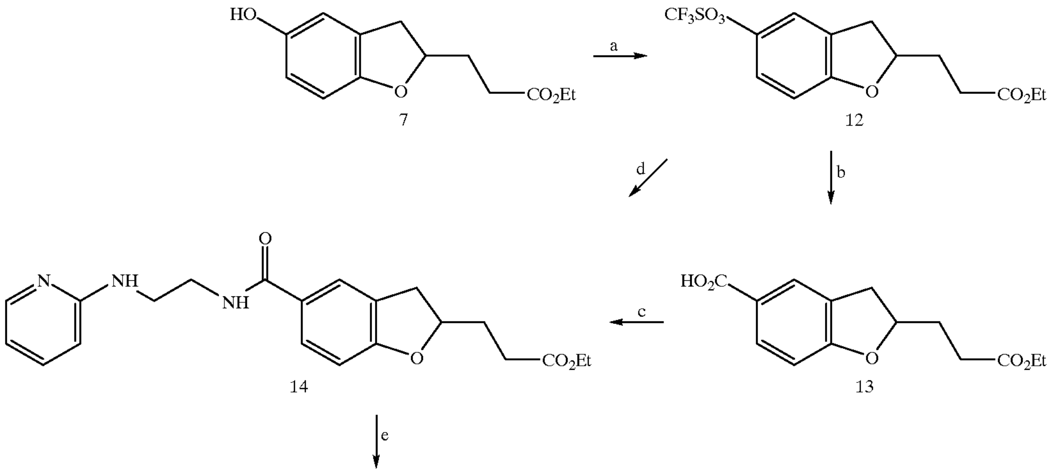
7, 12, 13, 14

-continued

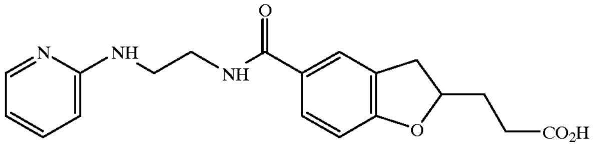

15 a) $(CF_3SO_2)_2O$, pyridine; b) CO, $Pd(OAc)_2$, $PPh_3$, DIEA, NMP, $NH_4HCO_3$, $H_2O$; c) N-(2-pyridinyl)ethylenediamine, EDC, HOBt, DIEA, DMF; d) N-(2-pyridinyl) ethylenediamine, CO, $Pd(OAc)_2$, $PPh_3$, DIEA, NMP, $NH_4HCO_3$, $H_2O$; e) 1N NaOH, EtOH.

Accordingly, a 5-hydroxybenzofuran-2-carboxylic acid ester, such as compound BB-1-1, prepared in the manner of M. L. Denney, et al., EP 0655439, is treated with TBDMS—Cl to provide the TBDMS derivative of the ester, BB-1-2. The ester is reduced to an aldehyde, such as compound BB-1-3. Wittig reaction affords an acrylic acid ester, as exemplified by compound BB-1-5. Catalytic reduction affords a benzofuran-2-acetic acid ester and a dihydrobenzofuran-2-acetic acid ester. Cleavage of the silyl ether group of each ester, by methods known to the art, affords a benzofuran-2-acetic acid ester, as exemplified by compound BB-1-6 and a dihydrobenzofuran-2-acetic acid ester as exemplified by compound BB-1-7.

As shown in Schemes BB-2 and BB-3, each phenol may be converted to a carboxylic acid via palladium-catalyzed carbonylation, such as compound BB-2-9 or BB-3-13, which are then condensed with an amine, such as N-(2-pyridinyl)ethylenediamine, to provide, after deesterification, the amide of the title compound of Example CC (BB-2-11) or DD (BB-3-15). Alternatively, the palladium-catalyzed carbonylation reaction with the triflates exemplified by compounds BB-2-8, or BB-3-12, may be trapped with N-(2-pyridinyl)ethylenediamine to provide, after deesterification, the corresponding 6-aminoacyl compounds, Example CC (BB-2-11) or DD (BB-3-15).

Scheme CC describes a method of preparing a further exemplary fibrinogen receptor template.

Scheme CC

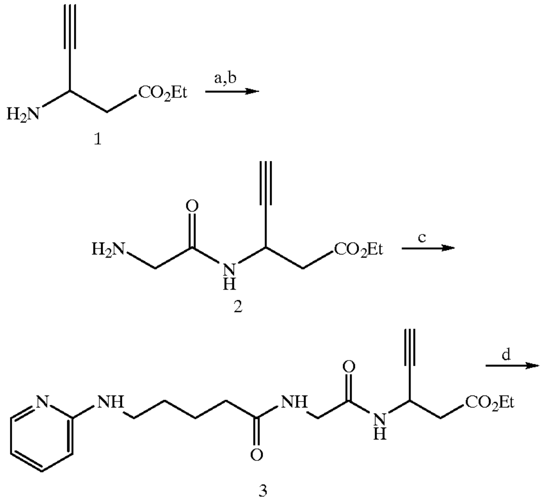

-continued

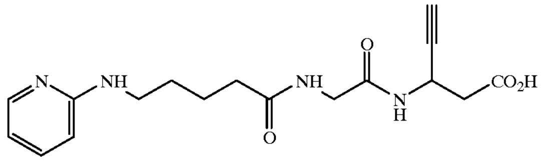

4 a) Boc-Gly, EDC, HOBT, DIEA, $CH_3CN$; b) TFA, $CH_2Cl_2$; c) 5-[(pyrid-2-yl)amino]pentanoic acid, EDC, HOBT, DIEA, DMF; d) 1N LiOH, THF, $CH_3CN$.

The preparation of the intermediate CC-2 begins with the coupling of the known ethyl 3-amino-4-pentynoate (WO 93/07867) with commercially available tert-butoxycarbonylglycine (Boc-Gly) under standard peptide bond forming conditions described in the previously referenced Bodansky publication. The product of this reaction is deprotected to CC-2 under acidic conditions which are known to effect removal of a Boc protecting group. Such conditions are described in the previously referenced Bodansky and Greene publications. The two intermediates CC-2 and 5-[(pyrid-2-yl)amino]pentanoic acid are coupled under standard peptide coupling conditions to give CC-3, which is hydrolyzed to CC-4 with lithium hydroxide in aqueous THF and $CH_3CN$.

Acid addition salts of the compounds are prepared in a standard manner in a suitable solvent form the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$ and $NH_4^+$ are specific examples of cations present in pharmaceutically acceptable salts.

This invention also provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds maybe encapsulated, tableted or prepared in a emulsion or syrup for oral administration. Pharmaceutically acceptable solid or liquid carriers may be added to enhance or stabilized the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

The compounds described herein are antagonists of the vitronectin receptor, and are useful for treating diseases wherein the underlying pathology is attributable to ligand or cell which interacts with the vitronectin receptor. For instance, these compounds are useful for the treatment of diseases wherein loss of the bone matrix creates pathology. Thus, the instant compounds are useful for the treatment of ostoeporosis, hyperparathyroidism, Paget's disease, hypercalcemia of malignancy, osteolytic lesions produced by bone metastasis, bone loss due to immobilization or sex hormone deficiency. The compounds of this invention are also believed to have utility as antitumor, antiinflammatory, anti-angiogenic and anti-metastatic agents, and be useful in the treatment of cancer, atherosclerosis and restenosis.

The peptide is administered either orally or parenterally to the patient, in a manner such that the concentration of drug is sufficient to inhibit bone resorption, or other such indication. The pharmaceutical composition containing the peptide is administered at an oral dose of between about 0.1 to about 50 mg/kg in a manner consistent with the condition of the patient. Preferably the oral dose would be about 0.5 to about 20 mg/kg. For acute therapy, parenteral administration is preferred. An intravenous infusion of the peptide in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg. The compounds are administered one to four times daily at a level to achieve a total daily dose of about 0.4 to about 400 mg/kg/day. The precise level and method by which the compounds are administered is readily determined by one routinely skilled in the art by comparing the blood level of the agent to the concentration required to have a therapeutic effect.

The compounds may be tested in one of several biological assays to determine the concentration of compound which is required to have a given pharmacological effect.

INHIBITION OF VITRONECTIN BINDING

Solid-Phase [$^3$H]-SK&F-107260 Binding to $\alpha_v\beta_3$: Human placenta or human platelet $\alpha_v\beta_3$ (0.1–0.3 mg/mL) in buffer T (containing 2 mM $CaCl_2$ and 1% octylglucoside) was diluted with buffer T containing 1 mM $CaCl_2$, 1 mM $MnCl_2$, 1 mM $MgCl_2$ (buffer A) and 0.05% $NaN_3$, and then immediately added to 96-well ELISA plates (Corning, New York, N.Y.) at 0.1 mL per well. 0.1–0.2 μg of $\alpha_v\beta_3$ was added per well. The plates were incubated overnight at 4° C. At the time of the experiment, the wells were washed once with buffer A and were incubated with 0.1 mL of 3.5% bovine serum albumin in the same buffer for 1 hr at room temperature. Following incubation the wells were aspirated completely and washed twice with 0.2 mL buffer A.

Compounds were dissolved in 100% DMSO to give a 2 mM stock solution, which was diluted with binding buffer (15 mM Tris-HCl (pH 7.4), 100 mM NaCl, 1 mM $CaCl_2$, 1 mM $MnCl_2$, 1 mM $MgCl_2$) to a final compound concentration of 100 μM. This solution is then diluted to the required final compound concentration. Various concentrations of unlabeled antagonists (0.0001–100 μM) were added to the wells in triplicates, followed by the addition of 5.0 nM of [$^3$H]-SK&F-107260 (65–86 Ci/mmol).

The plates were incubated for 1 hr at room temperature. Following incubation the wells were aspirated completely and washed once with 0.2 mL of ice cold buffer A in a well-to-well fashion. The receptors were solubilized with 0.1 mL of 1% SDS and the bound [$^3$H]-SK&F-107260 was determined by liquid scintillation counting with the addition of 3 mL Ready Safe in a Beckman LS Liquid Scintillation Counter, with 40% efficiency. Nonspecific binding of [$^3$H]-SK&F-107260 was determined in the presence of 2 μM SK&F-107260 and was consistently less than 1% of total radioligand input. The $IC_{50}$ (concentration of the antagonist to inhibit 50% binding of [$^3$H]-SK&F -107260) was determined by a nonlinear, least squares curve-fitting routine, which was modified from the LUNDON-2 program. The $K_i$ (dissociation constant of the antagonist) was calculated according to the equation: $K_i=IC_{50}/(1+L/K_d)$, where L and $K_d$ were the concentration and the dissociation constant of [$^3$H]-SK&F-107260, respectively.

Compounds of the present invention inhibit vitronectin binding to SK&F 107260 in the concentration range of 0.01 to 25 micromolar. Preferred compounds inhibit vitronectin binding at a concentration of less than 1 micromolar.

Compounds of this invention are also tested for in vitro and in vivo bone resorption in assays standard in the art for evaluating inhibition of bone formation, such as the pit formation assay disclosed in EP 528 587, which may also be performed using human osteoclasts in place of rat osteoclasts, and the ovarectomized rat model, described by Wronski et al., *Cells and Materials* 1991, Sup. 1, 69–74.

PARATHYROIDECTOMIZED RAT MODEL

Each experimental group consists of 5–6 male Sprague-Dawley rats. The rats are parathyroidectomized (by the vendor, Taconic Farms) 7 days prior to use. Twenty four hours prior to use, circulating ionized calcium levels are measured in whole blood immediately after it has been withdrawn by tail venipuncture into heparinized tubes. Rats are included if ionized Ca level (measured with a Ciba-Corning model 634 calcium pH analyzer) is $^2$1.2 mM/L. The rats are then put on a diet of calcium-free chow and deionized water. At the start of the experiment the rats weight approximately 100 g. Baseline Ca levels are measured and the rats are administered control vehicle (saline) or compound (dissolved in saline) as a single intravenous (tail vein) bolus injection followed immediately by a single subcutaneous injection of either human parathyroid hormone 1-34 peptide (hPTH1-34, dose 0.2 mg/kg in saline/0.1% bovine serum albumen, Bachem, Ca) or the PTH vehicle. The calcemic response to PTH (and any effect of compound on this response) is measured 2 h after compound/PTH administration.

RAT ULNA DRIFT MODEL

Each experimental group consists of 8–10 male Sprague-Dawley or Wistar rats of approximately 30–40 g body weight at the start of the experiment. The agent being tested is administered by an appropriate route as single or multiple daily doses for a period of seven days. Prior to administration of the first dose, the rats are given a single dose of a fluorescent marker (tetracycline 25 mg/kg, or calcein 10 mg/kg) that labels the position of bone forming surfaces at that point in time. After dosing of compound has been completed, the rats are killed and both forelimbs are removed at the elbow, the foot is removed at the ankle and the skin removed. The sample is frozen and mounted vertically on a microtome chuck. Cross sections of the midshaft region of the ulna are cut in the cryostat. The rate of bone resorption is measured morphometrically in the medial-dorsal portion of the cortical bone. The measurement is done as follows: the amount of bone resorbed at the periosteal surface is equal to the distance by which the periosteal surface has advanced towards the fluorescent label which had been incorporated at the endosteal bone formation surface on day zero; this distance is calculated by subtracting the width of bone between the label and the periosteal surface on day 7 from the width on day zero; the resorption rate in microns per day is calculated by dividing the result by 7.

HUMAN OSTEOCLAST RESORPTION ASSAY ("PIT ASSAY")

Aliquots of osteoclastoma-derived cell suspensions are removed from liquid nitrogen strorage, warmed rapidly at 37° C. and washed ×1 in RPMI-1640 medium by centrifugation (1000 rpm, 5 mins at 4° C.).

Aspirate the medium and replace it with murine anti-HLA-DR antibody, diluted 1:3 in RPMI-1640 medium. Incubate for 30 mins on ice and mix the cell suspension frequently.

The cells are washed ×2 with cold RPMI-1640 by centrifugation (1000 rpm, 5 mins at 4° C.) and the cells are transferred to a sterile 15 ml centrifuge tube. The number of mononuclear cells are enumerated in an improved Neubauer counting chamber.

Sufficient magnetic beads (5/mononuclear cell), coated with goat anti-mouse IgG, are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated ×10. The bead-coated cells are discarded.

The osteoclasts are enumerated in a counting chamber, using a large-bore disposable plastic pasteur to charge the chamber with the sample.

The cells are pelleted by centrifugation and the density of osteoclasts adjusted to $1.5\times10^4$/ml in EMEM medium, supplemented with 10% fetal calf serum and 1.7 g/liter of sodium bicarbonate.

3 ml aliquots of the cell suspension (per treatment) are decanted into 15 ml centrifuge tubes. The cells are pelleted by centrifugation.

To each tube 3 ml of the appropriate treatment are added (diluted to 50 uM in the EMEM medium). Also included are appropriate vehicle controls, a positive control (87MEM1 diluted to 100 ug/ml) and an isotype control (IgG2a diluted to 100 ug/ml). Incubate at 37° C. for 30 mins.

0.5 ml aliquots of the cells are seeded onto sterile dentine slices in a 48-well plate and incubated at 37° C. for 2 hours. Each treatment is screened in quadruplicate.

The slices are washed in six changes of warm PBS (10 ml/well in a 6-well plate) and then placed into fresh treatment or control. Incubate at 37° C. for 48 hours. tartrate resistant acid phosphatase (trap) procedure (selective stain for cells of the osteoclast lineage).

The slices are washed in phosphate buffered saline and fixed in 2% gluteraldehyde (in 0.2M sodium cacodylate) for 5 mins.

They are washed in water and incubated in TRAP buffer for 5 mins at 37° C.

Following a wash in cold water they are incubated in cold acetate buffer/fast red garnet for 5 mins at 4° C.

Excess buffer is aspirated, and the slices are air dried following a wash in water.

The TRAP positive osteoclasts are enumerated by bright-field microscopy and are then removed form the surface of the dentine by sonication.

Pit volumes are determined using the Nikon/Lasertec ILM21W confocal microscope.

INHIBITION OF RGD-MEDIATED GPIIB-IIIA BINDING

Purification of GPIIb-IIIa

Ten units of outdated, washed human platelets (obtained from Red Cross) were lyzed by gentle stirring in 3% octylglucoside, 20 mM Tris-HCl, pH 7.4, 140 mM NaCl, 2 mM $CaCl_2$ at 4° C. for 2 h. The lysate was centrifuged at 100,000 g for 1 h. The supernatant obtained was applied to a 5 mL lentil lectin sepharose 4B column (E.Y. Labs) preequilibrated with 20 mM Tris-HCl, pH 7.4, 100 mM NaCl, 2 mM $CaCl_2$, 1% octylglucoside (buffer A). After 2 h incubation, the column was washed with 50 mL cold buffer A. The lectin-retained GPIIb-IIIa was eluted with buffer A containing 10% dextrose. All procedures were performed at 4° C. The GPIIb-IIIa obtained was >95% pure as shown by SDS polyacrylamide gel electrophoresis.

Incorporation of GPIIb-IIIa in Liposomes

A mixture of phosphatidylserine (70%) and phosphatidylcholine (30%) (Avanti Polar Lipids) were dried to the walls of a glass tube under a stream of nitrogen. Purified GPIIb-IIIa was diluted to a final concentration of 0.5 mg/mL and mixed with the phospholipids in a protein:phospholipid ratio of 1:3 (w:w). The mixture was resuspended and sonicated in a bath sonicator for 5 mins. The mixture was then dialyzed overnight using 12,000–14,000 molecular weight cutoff dialysis tubing against a 1000-fold excess of 50 mM Tris-HCl, pH 7.4, 100 mM NaCl, 2 mM CaCl2 (with 2 changes). The GPIIb-IIIa-containing liposomes wee centrifuged at 12,000 g for 15 min and resuspended in the dialysis buffer at a final protein concentration of approximately 1 mg/mL. The liposomes were stored at −70° C. until needed.

Competitive Binding to GPIIb-IIIa

The binding to the fibrinogen receptor (GPIIb-IIIa) was assayed by an indirect competitive binding method using $[^3H]$-SK&F-107260 as an RGD-type ligand. The binding assay was performed in a 96-well filtration plate assembly (Millipore Corporation, Bedford, Mass.) using 0.22 um hydrophilic durapore membranes. The wells were precoated with 0.2 mL of 10 μg/mL polylysine (Sigma Chemical Co., St. Louis, Mo.) at room temperature for 1 h to block nonspecific binding. Various concentrations of unlabeled benzadiazapines were added to the wells in quadruplicate [$^3$H]-SK&F-107260 was applied to each well at a final concentration of 4.5 nM, followed by the addition of 1 μg of the purified platelet GPIIb-IIIa-containing liposomes. The mixtures were incubated for 1 h at room temperature. The GPIIb-IIIa-bound [3H]-SK&F-107260 was separated from the unbound by filtration using a Millipore filtration manifold, followed by washing with ice-cold buffer (2 times, each 0.2 mL). Bound radioactivity remaining on the filters was counted in 1.5 mL Ready Solve (Beckman Instruments, Fullerton, Calif.) in a Beckman Liquid Scintillation Counter (Model LS6800), with 40% efficiency. Nonspecific binding was determined in the presence of 2 μM unlabeled SK&F-107260 and was consistently less than 0.14% of the total radioactivity added to the samples. All data points are the mean of quadruplicate determinations.

Competition binding data were analyzed by a nonlinear least-squares curve fitting procedure. This method provides the IC50 of the antagonists (concentration of the antagonist which inhibits specific binding of [$^3$H]-SK&F-107260 by 50% at equilibrium). The IC50 is related to the equilibrium dissociation constant (Ki) of the antagonist based on the Cheng and Prusoff equation: Ki=IC50/(1+L/Kd), where L is the concentration of [3H]-SK&F-107260 used in the competitive binding assay (4.5 nM), and Kd is the dissociation constant of [3H]-107260 which is 4.5 nM as determined by Scatchard analysis.

Preferred compounds of this invention have an affinity for the vitronectin receptor relative to the fibrinogen receptor of greater than 4:1. More preferred compounds have a ratio of activity of greater than 10:1.

Vascular Smooth Muscle Cell Migration Assay

The compounds of the instant invention were tested for their ability to inhibit the migration and proliferation of smooth muscle tissue in an artery or vein in order to assess their ability to prevent restenosis of an artery, such as that which typically occurs following angioplasty.

Rat or human aortic smooth muscle cells were used. The cell migration was monitored in a Transwell cell culture chamber by using a polycarbonate membrane with pores of 8 um (Costar). The lower surface of the filter was coated with vitronectin. Cells were suspended in DMEM supplemented with 0.2% bovine serum albumin at a concentration of 2.5–5.0×$10^6$ cells/mL, and were pretreated with test compound at various concentrations for 20 min at 20° C. The solvent alone was used as control. 0.2 mL of the cell suspension was placed in the upper compartment of the chamber. The lower compartment contained 0.6 mL of DMEM supplemented with 0.2% bovine serum albumin. Incubation was carried out at 37° C. in an atmosphere of 95% air/5% $CO_2$ for 24 hr. After incubation, the non-migrated cells on the upper surface of the filter were removed by gentle scraping. The filter was then fixed in methanol and stained with 10% Giemsa stain. Migration was measured either by a) counting the number of cells that had migrated to the lower surface of the filter or by b) extracting the stained cells with 10% acetic acid followed by determining the absorbance at 600 nM.

EXAMPLES

Nuclear magnetic resonance spectra were recorded at either 250 or 400 MHz using, respectively, a Bruker AM 250 or Bruker AC 400 spectrometer. $CDCl_3$ is deuteriochloroform, DMSO-$d_6$ is hexadeuteriodimethylsulfoxide, and $CD_3OD$ is tetradeuteriomethanol. Chemical shifts are reported in parts per million (δ) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Infrared (IR) spectra were recorded on a Perkin-Elmer 683 infrared spectrometer in transmission mode. IR band positions are reported in inverse wavenumbers ($cm^{-1}$). Mass spectra were taken on either VG 70 FE, PE Syx API III, or VG ZAB HF instruments, using fast atom bombardment (FAB) or electrospray (ES) ionization techniques. Elemental analyses were obtained using a Perkin-Elmer 240C elemental analyzer. Melting points were taken on a Thomas-Hoover melting point apparatus and are uncorrected. All temperatures are reported in degrees Celsius.

Analtech Silica Gel GF and E. Merck Silica Gel 60 F-254 thin layer plates were used for thin layer chromatography. Both flash and gravity chromatography were carried out on E. Merck Kieselgel 60 (230–400 mesh) silica gel. Analytical and preparative HPLC were carried out on Rainin or Beckman chromatographs. ODS refers to an octadecylsilyl derivatized silica gel chromatographic support. 5 μApex-ODS indicates an octadecylsilyl derivatized silica gel chromatographic support having a nominal particle size of 5 μ, made by Jones Chromatography, Littleton, Colo. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp,. Denver, Colo.

Methyl (±)-7-carboxy-2,3,4,5-tetrahydro-4-methyl-3-oxo-1H-1,4-benzodiazepine-2-acetate and methyl (±)-7-carboxy-2,3,4,5-tetrahydro-3-oxo-4-phenylethyl-1H-1,4-benzodiazepine-2-acetate was prepared by the method of Bondinell et al. WO 93/00095. Tert-butyl 3-(bromomethyl)-4-fluorobenzoate and methyl (S)-7-carboxy-2,3,4,5-tetrahydro-4-methyl-3-oxo-1H-1,4-benzodiazepine-2-acetate was prepared by the method of Bondinell et al. WO 95/18619.

PREPARATION OF INTERMEDIATE COMPOUNDS

Preparation A

Preparation of Benzyl 3-[3,4-dihydro-8-carboxy-1-methyl-2,5-dioxo-1H-1,4-benzodiazepine]-4-propanoate a) 4-Iodo-2-amino Benzoic Acid Oxidation of 4-iodo-2-nitrotoluene according to Sasson, et. al., J. Org. Chem. 1986, 51, 2880–83, to give 4-iodo-2-nitro benzoic acid followed by reduction of the nitro group using iron and acetic acid gives the title compound.

b) 7-Iodoisatoic Anhydride

To a mechanically stirred ice cold solution of the compound of Preparation A(a) (26.3 g, 0.1 mol), $Na_2CO_3$ (10.6 g, 0.1 mol) and $H_2O$ (250 mL), is slowly added, via an addition funnel, a solution of 1.93M $COCl_2$ in toluene (80 mL). After 2 h, the precipitated product is isolated by filtration, and the solid is washed successively with $H_2O$ (200 mL), a 1:1 mixture of EtOH:$Et_2O$ (300 mL), and $Et_2O$ (200 mL), and dried under vacuum to yield the title compound.

c) Benzyl N-(2-amino-4-iodobenzoyl)-β-alanine

A magnetically stirred solution of the compound of Preparation A(b) (5.0 g, 0.0173 mol), β-alanine benzyl ester tosylate (5.85 g, 0.0173 mol), and DMAP (0.5 g, 0.0041 mol) in pyridine (35 mL) is heated for 2 h at 80° C. The reaction mixture is allowed to cool to RT and concentrated. The resulting residue is dissolved in EtOAc (100 mL), and washed successively with 10% cupric sulfate (2×50 mL), saturated $NaHCO_3$ (1×50 mL) and brine (1×50 mL), dried ($Na_2SO_4$), filtered, and concentrated to afford the title compound after chromatography (silica gel, 1:1 EtOAc/hexanes).

d) Benzyl N-(2-methylamino-4-iodobenzoyl)-β-alanine

A magnetically stirred solution of the compound of Preparation A(c) (2.0 mmol), 2,6-lutidine (0.35 mL, 3.0 mmol) and $CH_3I$ (0.19 mL, 3.0 mmol) in DMF (15 mL) is heated at 50° C. for 15 h. The reaction mixture is allowed to cool to RT and concentrated. The resulting residue is dissolved in EtOAc (75 mL), and washed successively with 10% citric acid (1×50 mL), saturated $NaHCO_3$ (1×50 mL) and brine (1×50 mL), dried ($Na_2SO_4$), filtered, and concentrated to afford the title compound after chromatography (silica gel, gradient 35–65% EtOAc/hexanes).

e) Benzyl 3-[3,4-dihydro-8-iodo-1-methyl-2,5-dioxo-1H-1,4-benzodiazepine]-4-propanoate To a cold (−30° C.) magnetically stirred solution of the compound of Preparation A(d) (0.305 g, 0.69 mmol), $Et_3N$ (0.144 g, 1.04 mmol) in $CH_2Cl_2$ (3 mL) is added slowly a solution of α-bromoacetyl bromide (0.09 mL, 1.04 mmol) in $CH_2Cl_2$ (2 mL) under argon atmosphere. The reaction mixture is allowed to warm to RT and stir for 2 h. The mixture is diluted with $CH_2Cl_2$ (40 mL) and washed successively with 10% citric acid (1×50 mL), saturated $NaHCO_3$ (1×50 mL), dried ($Na_2SO_4$), filtered, and concentrated. The resulting residue is dissolved in DMF (3 mL) and added via an addition funnel to a slurry of NaH (25 mg, 1.04 mmol) in DMF (2 mL) which is cooled to 0° C. After 2 h of stirring, the mixture is poured into an ice cold solution of 10% citric acid (50 mL) and extracted with EtOAc (3×40 mL). The combined extracts are washed with saturated $NaHCO_3$ (1×50 mL), dried ($Na_2SO_4$), filtered, and concentrated to afford the title compound after chromatography (silica gel, gradient 40–70% EtOAc/hexanes).

f) Benzyl 3-[3,4-dihydro-8-carboxy-1-methyl-2,5-dioxo-1H-1,4-benzodiazepine]-4-propanoate A solution of the compound of Preparation A(e) (3.2 mmol), $Pd(OAc)_2$ (0.16 mmol), and 1,1'-bis(diphenylphosphine)ferrocene (0.64 mmol,) in DMSO (20 mL) is heated to 65° C. under a carbon monoxide balloon for 18 h. The reaction mixture is diluted with water, acidified with 1 N HCl and extracted with $CH_2Cl_2$. The combined organic extracts are washed with water, dried ($Na_2SO_4$), filtered, and concentrated to afford the title compound after chromatography (silica gel).

Preparation B

Ethyl 3-[4H-imidazo[1,2-a][1,4]benzodiazepine-5(6H)-1-methyl-6-oxo-9-carboxyl-5-propanoic Acid a) Ethyl N-(2-amino-4-iodobenzoyl)-β-alanine A magnetically stirred solution of the compound of Preparation A(b) (0.0173 mol), β-alanine ethyl ester hydrochloride (0.0173 mol), and DMAP (0.5 g, 0.0041 mol) in pyridine (35 mL) is heated for 2 h at 80° C. The reaction mixture is allowed to cool to RT and concentrated. The resulting residue is dissolved in EtOAc (100 mL), and washed successively with 10% cupric sulfate (2×50 mL), saturated $NaHCO_3$ (1×50 mL) and brine (1×50 mL), dried ($Na_2SO_4$), filtered, and concentrated to afford the title compound after chromatography (silica gel, 1:1 EtOAc/hexanes).

b) Ethyl 3-[3,4-dihydro-8-iodo-2,5-dioxo-1H-1,4-benzodiazepine]-4-propanoate

To a cold (−30° C.) magnetically stirred solution of the compound of Preparation B(a) (0.69 mmol), and $Et_3N$ (0.144 g, 1.04 mmol) in $CH_2Cl_2$ (3 mL) is added slowly a solution of α-bromoacetyl bromide (0.09 mL, 1.04 mmol) in $CH_2Cl_2$ (2 mL) under argon atmosphere. The reaction mixture is allowed to warm to RT and stir for 2 h. The mixture is diluted with $CH_2Cl_2$ (40 mL) and wash successively with 10% citric acid (1×50 mL), saturated $NaHCO_3$ (1×50 mL), dried ($Na_2SO_4$), filtered, and concentrated. The resulting residue is dissolved in DMF (3 mL) and added via an addition funnel to a slurry of NaH (25 mg, 1.04 mmol) in DMF (2 mL) which is cooled to 0° C. After 2 h of stirring, the mixture is poured into an ice cold solution of 10% citric acid (50 mL) and extracted with EtOAc (3×40 mL). The combined extracts are washed with saturated $NaHCO_3$ (1×50 mL), dried ($Na_2SO_4$), filtered, and concentrated to afford the title compound after chromatography (silica gel).

c) Ethyl-3-[3,4-dihydro-8-iodo-2-thioxo-5-oxo-1H-1,4-benzodiazepine]-4-propanoate To a solution of the compound of Preparation B(b) (1.0 g, 2.49 mmol) in THF 10 mL) at RT and under an atmosphere of nitrogen is added Lawesson's reagent (1.0 g) and the reaction is heated at 50° C. for 2 h. The reaction mixture is allowed to cool to RT and is concentrated. Purifying the resulting residue by chromatography (silica gel, gradient, 40–60% EtOAc/hexane) gives the title compound.

d) Ethyl 3-[4H-imidazo[1,2-a][1,4]benzodiazepine-5(6H)-1-methyl-6-oxo-9-iodo]-5-propanoate To a vigorously stirred biphasic solution of the compound of Preparation B(c) (0.95 g, 2.27 mmol), $CH_3I$ (0.2 g) and a catalytic amount of tetrabutylammonium hydrogen sulfate in $CH_2Cl_2$ (10 mL) and $H_2O$ (10 mL), is added 2 N NaOH (1.2 mL) at RT. After 2 h, the layers are separated and the aqueous layer is washed with $CH_2Cl_2$ (2×25 mL). The combined organic extracts are dried ($Na_2SO_4$), filtered, and concentrated. The resulting residue is dissolved in toluene (10 mL) and allowed to react with propargyl amine (0.64 mL) and pyridine hydrochloride (0.23 g). The reaction is heated to reflux for 6 h, allowed to cool to RT, and concentrated to give the title compound after chromatography (silica gel, EtOAc).

e) Ethyl 3-[4H-imidazo[1,2-a][1,4]benzodiazepine-5(6H)-1-methyl-6-oxo-9-carboxy]-5-propanoic Acid A solution of the compound of Preparation B(d) (3.2 mmol), $Pd(OAc)_2$ (0.16 mmol), and 1,1'-bis(diphenylphosphine)ferrocene (0.64 mmol) in DMSO (20 mL) is heated at 65° C. under a carbon monoxide balloon for 18 h. The reaction mixture is diluted with $H_2O$, acidified with 1 N HCl and extracted with $CH_2Cl_2$ (3×). The combined organic extracts are washed with $H_2O$, dried ($Na_2SO_4$), filtered, and concentrated to afford the title compound after chromatography (silica gel).

Preparation C

Preparation of Ethyl 4-(1-piperazinyl)-1-piperidineacetate a) Ethyl 4-[4-(tert-butoxycarbonyl)-1-piperazinyl]-1-piperidineacetate The titled compound is prepared from tert-butyl 1-piperazinecarboxylate (Aldrich) and ethyl 4-oxo-1-piperidineacetate, Porter, et. al., EP 0 542 363 A2, by reductive amination with $NaBH_3CN$ according to the method of Porter, et. al., EP 0 542 363 A2.

b) Ethyl 4-(1-piperazinyl)-1-piperidineacetate

A solution of Preparation C(a) and 4M HCl in dioxane/ $CH_2Cl_2$ is stirred at RT for 18 h. The reaction mixture is concentrated to give the title compound as the hydrochloride salt.

Preparation D

Preparation of 3-Chloro-1-(2-pyridinyl)propylamine a) 3-[(1-Oxo-2-pyridinyl)amino]-1-propanol A mixture of 3-amino-1-propanol, 2-chloropyridine-N-oxide hydrochloride, and $NaHCO_3$ in n-butanol is heated to 100° C. for 18 h. The mixture is filtered, concentrated, partitioned between aqueous $NaHCO_3$ and EtOAc. The aqueous phase is extracted with EtOAc, dried, concentrated, and purified to give the title compound.

b) 3-(2-Pyridinyl)amino-1-propanol

A mixture of the compound of Preparation D(a), potassium formate, and 10% Pd/C in $CH_3OH$ is heated to reflux under argon for 48 h. The mixture is filtered, concentrated, and purified by chromatography to give the title compound.

c) 3-Chloro-1-(2-pyridinyl)propylamine

A solution of Preparation D(b) is treated with thionyl chloride in $CH_2Cl_2$ for 18 h. The mixture is concentrated to give the title compound.

Preparation E

Preparation of Ethyl 4-[4-(2-aminoethyl)-1-piperazinyl]-1-piperidineacetate a) Ethyl 4-[4-[2-(butoxycarbonylamino)ethyl]-1-piperazinyl]-1-piperidineacetate Following the general procedure of Porter, et. al., EP 0 542 363 A2, except substituting 4-[2-(butoxycarbonylamino)ethyl]-1-piperazine for 1-benzylpiperazine and ethyl 4-oxo-1-piperidineacetate for 1,1-dimethylethyl 4-oxo-1-piperidineacetate, gives the title compound.

b) Ethyl 4-[4-(2-aminoethyl)-1-piperazinyl]-1-piperidineacetate

The compound of Preparation E(a) is treated with TFA in $CH_2Cl_2$ to give the title compound.

Preparation F

Preparation of Ethyl 1-hydroxy-4-[4-(2-aminoethyl)-1-piperazinyl]cyclohexaneacetate Following the procedure of Preparation E, except substituting ethyl 1-(hydroxy)cyclohexaneacetate for ethyl 4-oxo-1-piperidineacetate, gives the title compound.

Preparation G

Preparation of N-[2-(Pyridinyl)amino]butyric Acid

Following the procedure of Preparation V(c), except substituting N-(1-oxo-2-pyridinyl)aminobutyric acid, Tortorella, et, al., Gazz. Chim. Ital., 1967, 97, 85–95, for the compound of Preparation V(b), gives the title compound.

Preparation H

Preparation of 2-(4-Hydroxybut-1-ylamino]pyridine a) 2-(4-Hydroxybut-1-ylamino)pyridine-N-oxide A mixture of 4-amino-1-butanol (1.76 g, 20 mmol), 2-chloropyridine N-oxide hydrochloride (3.98 g, 24 mmol), and $NaHCO_3$ (8.40 g, 100 mmol) in tert-amyl alcohol (50 mL) is heated at reflux under argon. After 48 h, the reaction is cooled, diluted with EtOH, filtered, and concentrated. The residue is reconcentrated from toluene, and chromatographed (silica gel) to give the title compound.

b) 2-(4-Hydroxybut-1-ylamino]pyridine

A briskly stirred mixture of the compound of Preparation H(a) (1.82 g, 10 mmol), ammonium formate (3.15 g, 50 mmol), and 10% Pd/C (10.64 g, 10 mmol) in absolute EtOH (50 mL) is warmed at 40° C. overnight, then is cooled to RT, and filtered through Celite®. The filtrate is concentrated, and the residue is partitioned between $H_2O$ (50 mL) and $CHCl_3$ (50 mL). The layers are separated, and the aqueous layer is extracted with $CHCl_3$. The combined organic layers are dried ($Na_2SO_4$), concentrated, and the residue is chromatographed (silica gel) to give the title compound.

Preparation I

Preparation of 5-[(Pyrid-2-yl)amino]pentanoic acid

A) Ethyl 5-[(pyrid-2-yl)amino]pentanoate N-oxide

A mixture of ethyl 5-aminopentanoate (2.9 g, 20 mmol), 2-chloropyridine N-oxide hydrochloride (3.98 g, 24 mmol), and $NaHCO_3$ (8.40 g, 100 mmol) in tert-amyl alcohol (50 mL) is heated at reflux under argon. After 48 h, the reaction is cooled, diluted with EtOH, filtered, and concentrated. The residue is reconcentrated from toluene and chromatographed (silica gel) to give the title compound.

b) Ethyl 5-[(pyrid-2-yl)amino]pentanoate

A briskly stirred mixture of the compound of Preparation I(a) (2.38 g, 10 mmol), ammonium formate (3.15 g, 50 mmol), and 10% Pd/C (10.64 g, 10 mmol) in absolute EtOH (50 mL) is warmed at 40° C. overnight, then is cooled to RT, and filtered through Celite®. The filtrate is concentrated, and the residue is partitioned between $H_2O$ (50 mL) and $CHCl_3$ (50 mL). The layers are separated, and the aqueous layer is extracted with $CHCl_3$. The combined organic layers are dried ($Na_2SO_4$) and concentrated. Chromatography (silica gel) gives the title compound.

c) 5-[(Pyrid-2-yl)amino]pentanoic acid

A mixture of the compound of Preparation I(b) (444 mg, 2.0 mmol), 1.0 N LiOH (3.0 mL, 3.0 mmol), THF (10 mL), and $H_2O$ (7 mL) is stirred at RT overnight, then is concentrated. The residue is taken up in $H_2O$ (5 mL) and neutralized with 1.0 N HCl. The precipitate is collected and dried in vacuum to give the title compound.

Preparation J

Preparation of 4-[N-Pyrid-2-yl-N-(toluenesulfonyl)amino]butanal oxime a) 2-[3-(Pyrid-2-yl)aminoprop-1-yl]-1,3-dioxolane N-oxide A mixture of 2-(3-aminopropyl)-1,3-dioxolane (100 mmol), 2-chloropyridine N-oxide hydrochloride (120 mmol), and $NaHCO_3$ (500 mmol) in tert-amyl alcohol (250 mL) is heated at reflux under argon. On completion, the reaction is cooled, diluted with EtOH, filtered, and concentrated. The residue is reconcentrated from toluene and chromatographed (silica gel) to give the title compound.

b) 2-[3-(Pyrid-2-yl)aminoprop-1-yl]-1,3-dioxolane

A briskly stirred mixture of the compound of Preparation J(a) (60 mmol), ammonium formate (300 mmol), and 10% Pd/C (60 mmol) in absolute EtOH (300 mL) is warmed at 40° C. overnight, cooled to RT, and filtered through Celite®. The filtrate is concentrated, and the residue is partitioned between $H_2O$ and $CHCl_2$. The layers are separated, and the aqueous layer is extracted with $CHCl_3$. The combined organic layers are dried ($Na_2SO_4$) and concentrated. Chromatography (silica gel) gives the title compound.

c) 2-[3-[N-Pyrid-2-yl-N-(toluenesulfonyl)amino]prop-1-yl]-1,3-dioxolane

Sodium hydride (55 mmol) is added carefully to a solution of the compound of Preparation J(b) (50 mmol) and 4-toluenesulfonyl chloride (55 mmol) in dry THF (200 mL). The reaction is stirred at RT until complete, then is quenched with saturated $NH_4Cl$ (200 mL), and the mixture is extracted with EtOAc. The combined organic extracts are dried ($MgSO_4$) and concentrated, and the residue is purified by chromatography (silica gel) to give the title compound.

d) 4-[N-Pyrid-2-yl-N-(toluenesulfonyl)amino]butanal

A solution of the compound of Preparation J(c) (40 mmol) and p-TsOH.$H_2O$ (4 mmol) in acetone (180 mL) and $H_2O$ (20 mL) is stirred at RT. When complete, the reaction is diluted with $Et_2O$ and washed sequentially with 5% $NaHCO_3$ and saturated brine. Drying ($MgSO_4$), concentration, and chromatography (silica gel) gives the title compound.

e) 4-[N-Pyrid-2-yl-N-(toluenesulfonyl)amino]butanal oxime

Hydroxylamine hydrochloride (33 mmol) is added to a solution of the compound of Preparation J(d) (30 mmol) and anhydrous NaOAc (66 mmol) in $CH_3OH$ (150 mL) at 0° C. The reaction is stirred at 0° C. until complete, then is concentrated, and the residue is partitioned between $H_2O$ and EtOAc. The layers are separated, and the aqueous layer is extracted with EtOAc. The combined organic layers are washed sequentially with 5% $NaHCO_3$ and saturated brine, dried ($MgSO_4$), and concentrated to afford the title compound.

Preparation K

Preparation of 2-[(3-Aminoprop-1-yl)amino]pyridine dihydrochloride

A) 2-[3-[(tert-Butoxycarbonyl)amino]prop-1-ylamino]pyridine-N-oxide

A mixture of N-Boc-1,3-diaminopropane (3.48 g, 20 mmol), 2-chloropyridine N-oxide hydrochloride (3.98 g, 24 mmol), and $NaHCO_3$ (8.40 g, 100 mmol) in tert-amyl alcohol (50 mL) is heated at reflux under argon. After 48 h, the reaction is cooled, diluted with EtOH, filtered, and concentrated. The residue is reconcentrated from toluene and chromatographed (silica gel) to give the title compound.

b) 2-[3-[(tert-Butoxycarbonyl)amino]prop-1-ylamino]pyridine

A briskly stirred mixture of the compound of Preparation K(a) (2.67 g, 10 mmol), ammonium formate (3.15 g, 50 mmol), and 10% Pd/C (10.64 g, 10 mmol) in absolute EtOH (50 mL) is warmed at 40° C. overnight, then is cooled to RT and filtered through Celite®. The filtrate is concentrated, and the residue is partitioned between $H_2O$ (50 mL) and $CHCl_3$ (50 mL). The layers are separated, and the aqueous layer is extracted with $CHCl_3$. The combined organic layers are dried ($Na_2SO_4$) and concentrated. Chromatography (silica gel) gives the title compound.

c) 2-[(3-Aminoprop-1-yl)amino]pyridine dihydrochloride

4 M HCl in dioxane (25 mL, 100 mmol) is added to a solution of the compound of Preparation K(b) (1.26 g, 5.0 mmol) in anhydrous $CH_2Cl_2$ (25 mL) at 0° C. The reaction is stirred at RT overnight and concentrated to afford the title compound.

Preparation L

Preparation of 4-[2-[2-(Pyridinyl)amino]ethyl]phenol

Following the procedure of Preparation V(a) and (c), except, substituting 4-(2-aminoethyl)phenol for N-(acetyl)ethylenediamine, gives the title compound.

Preparation M

Preparation of Benzyl 4-[2-(methylamino)acetyl]phenoxyacetate hydrochloride a) 4-[2-(Boc-methylamino)acetyl]phenol A solution of di-tert-butyl dicarbonate (5.96 g, 27.3 mmol) in 1,4-dioxane (25 mL) was added dropwise at 0° C. to a mixture of 4-[2-(methylamino)acetyl]phenol hydrochloride (5.0 g, 24.8 mmol), 1,4-dioxane (30 mL), $H_2O$ (25 mL) and 1.0 N NaOH (25 mL, 25 mmol). After 24 h, the reaction was warmed to RT and stirred for 1.5 h. More 1.0 N NaOH (25 mL, 25 mmol) was added, and the reaction was stirred for an additional 0.5 h at RT, and concentrated. The residue was diluted with EtOAc (80 mL), and the mixture was acidified to pH 2 using 1.0 M $NaHSO_4$. The resulting mixture was extracted with EtOAc, and the combined organic layers were washed with $H_2O$ and dried ($Na_2SO_4$). Filtration and concentration gave the title compound (6.39 g, 99%): $^1H$ NMR (250 MHz, $CDCl_3$) δ6.70–8.05 (m, 4 H), 4.53 (s, 2H), 2.98 (s, 3H), 1.50 (s, 9H).

b) Benzyl 4-[2-(Boc-methylamino)acetyl]phenoxyacetate

A mixture of the compound of Preparation L(a) (5.04 g, 19.0 mmol) and $K_2CO_3$ (2.63 g, 19.0 mmol) in acetone (100 mL) was stirred at reflux under argon for 1 h. The mixture was cooled to RT and benzyl bromoacetate (5.23 g, 22.8 mmol) was added. The reaction was heated at reflux for 18 h, then was cooled and filtered. The filter cake was washed with acetone, and the filtrate was concentrated. The residue was dissolved in $CH_2Cl_2$ (300 mL) was washed sequentially with $H_2O$ (50 mL) and brine (50 mL). Drying ($Na_2SO_4$), concentration, and flash chromatography (silica gel, 1:3 EtOAc/hexanes) yielded the title compound (7.28 g, 93%): $^1H$ NMR (250 MHz, $CDCl_3$) δ6.85–7.95 (m, 9 H), 5.23 (s, 2H), 4.71 (s, 2H, 4.55 (d, 2H), 2.95 (d, 3H), 1.45 (d, 9H).

c) Benzyl 4-[2-(methylamino)acetyl]phenoxyacetate hydrochloride

A mixture of the compound of Preparation L(b) (7.26 g, 17.57 mmol) and 4 M HCl in 1,4-dioxane (150 mL) was stirred for 1 h at RT. Concentration and trituration with $Et_2O$ afforded the title compound as a white powder (5.93 g, 97%): $^1H$ NMR (250 MHz, $CD_3OD$) δ7.05–8.00 (m, 9 H), 5.23 (s, 2H), 4.88 (s, 2H), 4.65 (s, 2H), 2.80 (s, 3H).

Preparation N

Preparation of Dimethyl 4-[2-(methylamino)acetyl]-1,2-phenylenedioxydiacetate hydrochloride a) 4-[2-(Boc-methylamino)acetyl]-1,2-dihydroxybenzene Following the procedure of Preparation L(a), except substituting adrenalone hydrochloride (5.0 g, 23.0 mmol) for 4-[2-(methylamino)acetyl]phenol hydrochloride, the title compound (1.2 g, 19%) was prepared following flash chromatography (silica gel, 1:1 EtOAc/hexanes): MS (ES) m/e 282.2 $[M+H]^+$.

b) Dimethyl 4-[2-(Boc-methylamino)acetyl]-1,2-phenylenedioxydiacetate

Following the procedure of Preparation L(b), except substituting the compound of Preparation M(a) (0.9 g, 3.2 mmol) for the compound of Preparation L(a) and methyl bromoacetate (1.23 g, 8.0 mmol) for benzyl bromoacetate, the title compound (1.11 g, 81%) was prepared: MS (ES) m/e 426.2 $[M+H]^+$.

c) Dimethyl 4-[2-(methylamino)acetyl]-1,2-phenylenedioxydiacetate hydrochloride

Following the procedure of Preparation L(c), except substituting the compound of Preparation M(b) (1.11 g, 2.6 mmol) for the compound of Preparation L(b), the title compound was prepared (1.1 g, quantitative): Ms (ES) m/e 326.0 $[M+H]^+$.

Preparation O

Preparation of Ethyl (6-carboxy-1,2,3,4-tetrahydroisoquinolin-2-yl)acetate a) Ethyl (6-Methoxy-1,2,3,4-tetrahydroisoquinolin-2-yl) acetate A solution of 6-methoxy-1,2,3,4-tetrahydroisoquinoline, Sall and Grunewald, J. Med. Chem. 1987, 30, 2208–2216 (1.1 mmol), ethyl chloroacetate (1.17 mmol), and $K_2CO_3$ (1.17 mmol) in $CH_3CN$ (10 mL) is stirred for 18 h. The mixture is partitioned between EtOAc and $H_2O$. The organic phase is concentrated to an oil, which is purified by chromatography (silica gel, gradient, 20–80% EtOAc/hexane) to afford the title compound.

b) Ethyl (6-Hydroxy-1,2,3,4-tetrahydroisoquinolin-2-yl) acetate

A solution of compound of Preparation O(a)(0.249 g, 1.0 mmol), 1M $BBr_3$ in $CH_2Cl_2$ (1.0 mL, 1.0 mmol) is stirred at −70° C. for 2 h and then stirred at RT for 12 hr. The solution is concentrated, and the solution of the resulting oil in EtOAc is washed with $H_2O$, 5% $NaHCO_3$, and $H_2O$, dried ($Mg_2SO_4$), filtered, and concentrated to an oil to afford the title compound (0.223 g, 95%).

c) Ethyl[6-(trifluoromethylsulfonyloxy)-1,2,3,4-tetrahydroisoquinolin-2-yl]acetate A solution of the compound of Preparation O(b)(0.235 g, 1.0 mmol), trifluorosulfonic acid anhydride (0.23 mL, 1.1 mmol,) and $Et_3N$ (0.32 mL, 1.5 mmol) in $CH_2Cl_2$ (5 mL) is stirred for 8 h. The solution is concentrated to an oil which is taken up in EtOAc. The organic phase is washed with 5% $NaHCO_3$ and $H_2O$. The organic phase is dried ($Na_2SO_4$), filtered, concentrated to afford the title compound (0.300 g, 82%).

d) Ethyl (6-carboxy-1,2,3,4-tetrahydroisoquinolin-2-yl) acetate

A solution of the compound of Preparation O(c)(0.367 g, 1.0 mmol), $Pd(OAc)_2$ (0.022 g, 0.1 mmol,), $Ph_3P$ (0.262 g, 1.0 mmol), diisopropylamine (0.34 mL, 2.5 mmol), and NMP (5 mL) in 10% $NH_4CO_3$ is stirred for 8 h under an atmosphere of CO. The solution is concentrated to an oil which is purified by chromatography (silica gel, gradient, 10–33% $CH_3OH/CH_2Cl_2$) to afford the title compound (0.19 g, 72%).

Preparation P

Preparation of Ethyl (6-carboxy-1,2,3,4-tetrahydro-1-oxo-isoquinolin-2-yl)acetate a) Ethyl (6-Methoxy-1-oxo-1,2,3,4-tetrahydroisoquinolin-2-yl)acetate A mixture of 6-methoxy-1,2,3,4-tetrahydro-1-oxo-isoquinoline, Sall and Grunewald, J. Med. Chem. 1987, 30, 2208–2216 (0.39 mmol) and NaH (0.17 g, 0.43 mmol, 60% oil dispersion) in THF (5 mL) is heated to reflux for 1 h and then allowed to cool to RT. Ethyl chloroacetate (0.43 mmol) is added and the mixture is allowed to stir for 1 h. The mixture is quenched with $H_2O$ (10 mL) and washed with EtOAc. The organic layers are combined, washed with $H_2O$ (10 mL) and concentrated to an oil which is purified by (silica gel, gradient, 10–33% $CH_3OH/CH_2Cl_2$) to afford the title compound.

b) Ethyl (6-Hydroxy-1-oxo-1,2,3,4-tetrahydroisoquinolin-2-yl)acetate

A solution of the compound of Preparation P(a) (0.263 g, 1.0 mmol) and 1M $BBr_3$ in $CH_2Cl_2$ (1.1 mL) is stirred at −70° C. for 2 h and then at RT for 4 h. The solution is concentrated to an oil which is taken up in EOAc. The organic phase is washed with $H_2O$, 5% $NaHCO_3$, $H_2O$, dried ($MgSO_4$), filtered, and concentrated to afford the title compound (0.20 g, 80%).

c) Ethyl [6-(trifluoromethylsulfonyloxy)-1,2,3,4-tetrahydro-1-oxo-isoquinolin-2-yl]acetate A solution of the compound of Preparation P(b) (3.4 mmol) and trifluorosulfonic acid anhydride (3.4 mmol, mL) in pyridine (5 mL) is chilled at 0° C. and allowed to warm RT for 1 h. The mixture is quenched with $H_2O$ (5 mL) and washed with EtOAc. The organic layers are combined, washed with $H_2O$ (7 mL) and concentrated to an oil. The residue is purified chromatography (by silica gel, gradient, 14–75% EtOAc/hexane) to afford the title compound.

d) Ethyl (6-carboxy-1-oxo-1,2,3,4-tetrahydroisoquinolin-2-yl)acetate

A solution of the compound of Preparation P(c) (0.23 g, 1.0 mmol), $Pd(OAc)_2$ (0.026 g, 0.1 mmol), $Ph_3P$ (0.262 g, 1.0 mmol), diisopropylamine (0.23 mL, 2.0 mmol) and NMP (7 mL) in 10% $NH_4CO_3$ is stirred for 8 h under an atmosphere of CO. The solution is concentrated to an oil which is purified by chromatography (silica gel, gradient, 25–75% $CH_3OH/CH_2Cl_2$) to afford the title compound (0.31 g, 70%).

Preparation Q

Preparation of Ethyl (6-carboxy-tetralin-2-yl)acetate a) Ethyl [6-(trifluoromethylsulfonyloxy)-tetralin-2-yl] acetate Following the procedure of Preparation O(c), except substituting ethyl (6-hydroxy-tetralin-2-yl)actate, Fisher, et. al., EP 0635492, Scheme 6 and Example 20, parts A–D for the compound of Preparation O(b), gives the title compound.

b) Ethyl (6-carboxy-tetralin-2-yl)acetate

Following the procedure of Preparation O(d), except substituting the compound of Preparation Q(a) for the compound of Preparation O(c), gives the title compound.

Preparation R

Preparation of Ethyl (5-aminobenzofuran-2-yl) propionate and Ethyl (5-amino-2,3-dihydro-benzofuran-2-yl]propionate a) 2-(Ethoxycarbonyl)methoxy-5-nitrobenzaldehyde A solution of 5-nitrosalicylaldehyde (Aldrich) (0.167 g, 1.0 mmol), ethyl bromoacetate (0.166 g, 1.0 mmol), $K_2CO_3$ (0.276 g, 2.0 mmol) and NaI (0.015 g, 0.1 mmol) in THF (10 mL) is heated to 80° C. for 24 h. The solution is concentrated and the residue is purified by chromatography (silica gel, gradient, 5–20% $CH_3OH$ in $CH_2Cl_2$) to afford the title compound (0.20 g, 87%).

b) Ethyl (5-nitrobenzofuran-2-yl)carboxylate

A solution of the compound of Preparation R(a) (0.229 g, 1.0 mmol) and DBU (0.152 g, 1.0 mmol) in EtOH (10 mL) is allowed to stir at RT for 18 h. The solution is concentrated and the residue is treated with EtOH (10 mL). The solution is bubbled with HCl gas for 2 min and refluxed for 5 h. The solution is concentrated and the residue is treated with EtOAc. The organic phase is washed with $H_2O$, 5% citric acid, $H_2O$, 5% $NaHCO_3$, and $H_2O$. The organic phase is concentrated to afford the title compound (0.19 g, 81%).

c) Ethyl (5-nitrobenzofuran-2-yl)carboxaldehyde

A cold solution (−78° C.) of the compound of Preparation R(b) (0.235 g, 1.0 mmol) in THF (5 mL) is treated with 1M DiBAL in THF (1.0 mL, 1.0 mmol). The solution is stirred at −78° C. for 30 min and at RT for 3 h. The solution is treated with $CH_3CO_2H$ (3 mL) followed by $H_2O$ (2 mL). The solution is concentrated and the residue is treated with toluene to azeotrope off the acetic acid. Drying in vacuo afforded the title compound (0.100 g, 52%).

d) Ethyl (5-nitrobenzofuran-2-yl)propenoate

A solution of triethyl phosphonoacetate (0.224 g, 1.0 mmol) in THF (5 mL) is treated with NaH (60% suspension in mineral oil, 0.04 g, 1.0 mmol) at 0° C. for 1 h. To the solution is added the compound of Preparation R(c)(0.235 g, 1.0 mmol). The solution is stirred at RT for 18 h, concentrated, and the residue is purified by chromatography (silica gel, gradient, 5–20% EtOAc/hexane) (EtOAc/Hexane 0.5:9 to 4:1) to afford the title compound (0.2 g, 77%.

e) Ethyl (5-aminobenzofuran-2-yl)propionate and Ethyl (5-amino-2,3-dihydrobenzofuran-2-yl]propionate A solution of the compound of Preparation R(d) (0.261 g, 1.0 mmol) in EtOH (5 mL) containing 10% Pd/C (0.026 g) is hydrogenated at 45 psi for 1 h. The solution is filtered through Celite and the filtrate is concentrated and chromatographed (silica gel, gradient, 25–75% EtOAc/hexane) affords the title compounds.

Preparation S

Preparation of Ethyl (5-carboxy-benzofuran-2-yl) propionate a) Ethyl [5-(tert-butyldimethylsilyloxy)benzofuran-2-yl] carboxylate A solution of ethyl [5-(hydroxy)benzofuran-2-yl] carboxylate, Denny, et. al., EP 0655439, (0.206 g, 1.0 mmol), tert-(butyl)dimethylsilyl chloride (0.23 mL, 1.0 mmol) and imidazole (0.34 g, 1.0 mmol) in THF is allowed to stir for 4 h. The solution is concentrated and the residue is treated with EtOAc. The organic phase is washed with $H_2O$, dried ($Na_2SO_4$), and concentrated to afford the title compound (0.35 g, 90%).

b) Ethyl [5-[tert-(butyl)dimethylsilyloxy]benzofuran-2-yl]propenoate

Following the procedure of Preparation R(c) and (d), except substituting the compound of Preparation S(a) for the compound of Preparation R(b), gives the title compound.

c) Ethyl [5-(hydroxy)benzofuran-2-yl]propionate and Ethyl [5-hydroxy-2,3-dihydrobenzofuran-2-yl]propionate A mixture of the compound of Preparation S(b) (0.234 g, 1.2 mmol) and 10% Pd/C (0.023 g, 10% wt) in EtOH(5 mL) is hydrogenated at 50 psi for 1 h. The mixture is filtered through Celite and concentrated. A solution of the residue (0.34 g, 1.0 mmol) and $Et_4NF$ (0.149 g, 1.0 mmol) in THF (10 mL) is allowed to stir at RT for 18 h. The solution is concentrated and purified by chromatography (silica gel) to give the title compounds (0.25 g, 57%).

d) Ethyl [5-(trifluoromethylsulfonyloxy)benzofuran-2-yl] propionate

Following the procedure of Preparation O(c), except substituting ethyl [5-(hydroxy)benzofuran-2-yl]propionate of Preparation S(c) for the compound of Preparation O(b), gives the title compound.

e) Ethyl (5-carboxy-benzofuran-2-yl)propionate

Following the procedure of Preparation O(d), except substituting the compound of Preparation S(d) for the compound of Preparation O(c), gives the title compound.

Preparation T

Preparation of Ethyl (5-carboxy-2,3-dihydro-benzofuran-2-yl)propionate a) Ethyl [5-(trifluoromethylsulfonyloxy)-2,3-dihydro-benzofuran-2-yl]propionate Following the procedure of Preparation S(d), except substituting ethyl [5-hydroxy-2,3-dihydro-benzofuran-2-yl] propionate from Preparation S(c) for ethyl [5-(hydroxy) benzofuran-2-yl]propionate from Preparation S(c), gives the title compound.

b) Ethyl (5-carboxy-2,3-dihydro-benzofuran-2-yl) propionate

Following the procedure of Preparation S(e), except substituting the compound of Preparation T(a) for the compound of Preparation S(d), gives the title compound.

Preparation U

Preparation of Ethyl (±)-3-[(glycyl)amino]-4-pentynoate trifluoroacetate a) Ethyl (±)-3-[[(N-tert-butoxycarbonyl)glycyl]amino]-4-pentanoate DIEA (0.92 mL, 5.32 mmol) was added to a stirred solution of ethyl (±)-3-amino-4-pentynoate (0.3 g, 2.13 mmol), Boc-Gly (0.56 g, 3.19 mmol), $HOBt.H_2O$ (0.43 g, 3.19 mmol), and EDC (0.61 g, 3.19 mmol) in anhydrous $CH_3CN$ (15 mL) at RT. After 34 h, the reaction mixture was concentrated, diluted with $CH_2Cl_2$ (70 mL), and washed sequentially with 5% $NaHCO_3$ (2×15 mL) and brine (15 mL). Drying ($MgSO_4$), concentration, and chromatography (silica gel, 1:1 EtOAc/hexane) gave the title compound (0.5 g, 79%) as a colorless oil: MS (ES) m/e 299.2 $(M+H)^+$.

b) Ethyl (±)-3-[(glycyl)amino]-4-pentynoate trifluoroacetate

A solution of TFA (5 mL) and $CH_2Cl_2$ (15 mL) at RT was added all at once to the compound of Preparation S(a) (0.5 g, 1.68 mmol). After 30 min, the solution was concentrated, and the residue was reconcentrated from toluene (to remove residual TFA) to afford the title compound (0.55 g, 106%) as a light yellow syrup: MS (ES) m/e 199.2 $(M+H)^+$.

Preparation V

Preparation of N-(2-Pyridinyl)ethylenediamine a) N-Acetyl-N'-(1-oxo-2-pyridinyl)ethylenediamine A mixture of N-(acetyl)ethylenediamine (0.5 g, 5 mmol), 2-chloropyridine-N-oxide hydrochloride (1.6 g, 10 mmol), $NaHCO_3$ (1.6 g, 19 mmol), and n-butanol (5 mL) was heated to 100° C. for 18 h. The mixture was then allowed to cool, and it was filtered and the filtrate concentrated. The resulting residue was purified by chromatography (silica gel, step gradient, 2%–10% $CH_3OH/CH_2Cl_2$) to give the title compound as a pale yellow solid (0.40 g, 45%): MS (ES) m/e 196 $[M+H]^+$.

b) N-(1-Oxo-2-pyridinyl)ethylenediamine

A mixture of the compound of Preparation V(a)(0.4 g) and concentrated HCl (50 mL) was heated to 90° C. for 4 d, concentrated, and the residue was recrystallized ($CH_3OH$:$CHCl_3$) to give the title compound as off-white needles (3.2 g, 82%): MS (ES) m/e 154.2 $[M+H]^{+\cdot}$ c) N-(2-Pyridinyl)ethylenediamine A mixture of the compound of Preparation V(b)(1.0 g, 5 mmol), potassium formate (2.2 g, 25 mmol), 10% Pd/C (0.30 g), and $CH_3OH$ (20 mL) was heated to reflux under argon for 48 h. The mixture was filtered, the filtrate was concentrated, and the residue was purified by chromatography (silica gel, 10% $CH_3OH/CH_2Cl_2$) to give the title compound as an amber oil (0.30 g, 41%): MS (ES) m/e 138.1 $[M+H]^+$.

Preparation W

Preparation of Methyl (S)-2,3,4,5-Tetrahydro-7-iodo-3-oxo-1H-1,4-benzodiazepine-2-acetate a) Dimethyl (R)-malate O-triflate A solution of dimethyl (R)-malate (12.96 g, 80 mmol) and pyridine (6.8 mL, 84 mmol) in $CH_2Cl_2$ (50 mL) was added dropwise under argon at 0° C. to a solution of triflic anhydride (14.2 mL, 84 mmol) in dry $CH_2Cl_2$ (40 mL) in a flame-dried flask. The resulting yellow-orange mixture was stirred at 0° C. for 30 min, and then at RT for 4 h. The reaction was quenched by adding $H_2O$ (50 mL) and the organic phase was washed three times with $H_2O$ and brine, dried ($MgSO_4$), and concentrated to give the title compound as an off white solid (22.45 g, 95%): MS (ES) m/e 295.0 $[M+H]^+$.

b) Dimethyl N-[2-(cyano)phenyl]-(S)-aspartate

A solution of compound of Preparation W(a)(22.4 g, 76.2 mmol) in 1:1 $CH_3Cl$:hexane (80 mL) was added to a solution of 2-aminobenzonitrile (9.0 g, 76.2 mmol) and 2,6-di-tert-butylpyridine (14.5 g, 76.2 mmol) in 1:1 $CH_3Cl$-hexane (100 mL) in a flame-dried flask under argon at 0° C. The resulting mixture was stirred at 0° C. for 30 min and then at RT for 3 d. The resulting mixture was concentrated, the residue was taken up into EtOAc, washed with 5% HCl and brine, and dried ($MgSO_4$). The resulting mixture was concentrated and the residue was purified by flash chromatography (silica gel, 12% EtOAc/hexane) to give the title compound as a clear oil (12.3 g, 62%): MS (ES) m/e 263.3 $[M+H]^+$.

c) Methyl (S)-2,3,4,5-Tetrahydro-3-oxo-1H-1,4-benzodiazepine-2-acetate

A mixture of compound of Preparation W(b)(12 g, 45.7 mmol), $Et_3N$ (7.64 mL, 54.84 mmol), and Raney-Ni (46 g, prewashed by $CH_3OH$) in $CH_3OH$ (200 mL) was stirred at RT under a $H_2$ balloon for 2 d. The mixture was filtered and the catalyst was washed 3× with $CH_3OH$. The filtrate was concentrated and the residue was purified by flash chromatography (silica gel, step gradient, 0–5% $CH_3OH/CH_2Cl_2$) to yield the title compound as a white solid (7.63 g, 74%): MS (ES) m/e 235.3 $[M+H]^+$. The title compound was shown to contain approximately 23% of the (R)-enantiomer by NMR.

d) Methyl (S)-2,3,4,5-Tetrahydro-7-iodo-3-oxo-1H-1,4-benzodiazepine-2-acetate

Pyridine-ICl complex: 1M iodinemonochloride in $CH_2Cl_2$ (100 mL) was added slowly to a solution of pyridine (8.5 mL, 105 mmol) in $CH_2Cl_2$ (20 mL), stirred under argon and pre-cooled to 5° C., so as to maintain an internal temperature between 10–15° C. The mixture was stirred at 5–10° C. for 20 min. Hexane (50 mL) was added and the mixture was stirred in a cold bath for an additional 30 min. The solid which formed was collected by filtration, washed with hexane and with petroleum ether, and dried to yield pyridine-ICl complex (22.5 g) as a yellow solid which was used without further purification.

Pyridine-ICl complex (1.27 g, 5.28 mmol) was added portionwise to a solution of the compound of Preparation W(c) (1.18 g, 4.8 mmol) in 1:1 $CH_2Cl_2$: $CH_3OH$ (40 mL). The resulting mixture was stirred at RT for 40 min, treated with 1M $NaHSO_3$ (20 mL), and the resulting solid was collected by filtration, washed with $Et_2O$, and dried to yield the title compound as an off white solid (1.72 g, quantitative): MS (ES) m/e 361.2 $[M+H]^+$.

Preparation X

Preparation of Methyl (S)-7-carboxy-2,3,4,5-tetrahydro-3-oxo-4-(2,2,2-trifluoroethyl)-1H-1,4-benzodiazepine-2-acetate a) tert-Butyl 4-fluoro-3-[(2,2,2-trifluoroethyl)aminomethyl]benzoate A mixture of tert-butyl 3-bromomethyl-4-fluorobenzoate (14 g, 48 mmol) and 2,2,2-trifluoroethylamine (25 g, 250 mmol) in THF (300 mL) was stirred under argon at RT for 4 d, concentrated, and the residue partitioned between $Et_2O$ and 10% $K_2CO_3$. The organic phase was washed with 10% $K_2CO_3$ and brine, dried, and concentrated. The residue was purified by chromatography (silica gel, step gradient, 0–8% ethyl acetate/hexane) to give the title compound as a pale yellow oil (10.7, 72%): MS (ES) m/e 308.3$[M+H]^+$.

b) tert-Butyl (S)-4-fluoro-3-[[[2-(benzyloxycarbonyl)amino-1,4-dioxo-4-methoxy-1-butyl](2,2,2-trifluoroethyl)amino]methyl]benzoate Cyanuric fluoride (2.8 mL, 36 mmol) was added dropwise to a solution of Cbz-L-aspartic acid-β-methyl ester (10 g, 36 mmol) and pyridine (2.8 mL, 36 mmol) in $CH_2Cl_2$ (100 mL) stirred under argon at RT. The resulting mixture was stirred at RT overnight, diluted with $CH_2Cl_2$ (100 mL), and quenched with $H_2O$ (100 mL). The mixture was filtered, the phases were separated, and the organic phase was dried ($MgSO_4$) and concentrated to afford Cbz-L-aspartic acid-β-methyl ester acid fluoride. The acid fluoride was dissolved in $CH_2Cl_2$ (50 mL) and added dropwise to a solution of the compound of Preparation X(a) (5 g, 16 mmol) in $CH_2Cl_2$ (200 mL) and pyridine (3 mL, 37 mmol) stirred under argon at 0° C. After the addition was complete, the resulting solution was stirred at RT overnight, washed with $H_2O$, dried ($MgSO_4$), and concentrated. The residue was purified by chromatography (silica gel, $CH_2Cl_2$) to give the title compound as a colorless syrup (10 g, 100%): MS (ES) m/e 571.2 $[M+H]^+$.

c) tert-Butyl (S)-4-fluoro-3-[[[2-amino-1,4-dioxo-4-methoxy-1-butyl](2,2,2-trifluoroethyl)amino]methyl]benzoate A mixture of the compound of Preparation X(b) (10 g) and 10% Pd/C (2 g) in $CH_3OH$ (200 mL) was shaken in an atmosphere of $H_2$ (45 psi) for 2 h. The mixture was filtered, the filtrate was concentrated, and the residue was purified by chromatography (silica gel, step gradient, 0–2% $CH_3OH/CH_2Cl_2$) to give the title compound as a colorless syrup (6 g, 78%), MS (ES) m/e 436.9 $[M+H]^+$.

d) Methyl (S)-7-(t-butoxycarbonyl)-2,3,4,5-tetrahydro-3-oxo-4-(2,2,2-trifluoroethyl)-1H-1,4-benzodiazepine-2-acetate A solution of the compound of Preparation X(c) (5.8 g) in DMSO (60 mL) was heated under argon to 125° C. for 6 h. The mixture was allowed to cool, poured into ice water, and extracted 3× with EtOAc. The combined organic extracts were washed with $H_2O$ and brine, dried ($MgSO_4$), and concentrated. The residue was purified by chromatography (silica gel, step gradient, 0%–5% $CH_3OH/CH_2Cl_2$) to give the title compound as a white foam (3 g, 50%): NMR (400 MHz, $CDCl_3$) δ7.72 (d, J=8.4 Hz, 1H), 7.59 (s, 1H) 6.53 (d, J8.4 Hz, 1H), 5.49 (d, J=16.7 Hz, 1H), 5.15 (m, 1H), 4.57 (d, J=6 Hz, 1H), 4.31 (m, 1H), 3.99 (d, J=16.7 Hz, 1H), 3.80 (m 1H), 3.75 (s, 3H), 3.00 (dd, J=16.2, 6.5 Hz, 1H), 2.72 (dd, J=16, 6.4 Hz, 1H), 1.57 (s, 9H).

e) Methyl (S)-7-carboxy-2,3,4,5-tetrahydro-3-oxo-4-(2,2,2-trifluoroethyl)-1H-1,4-benzodiazepine-2-acetate Anisole (1.56 g, 14 mmol) was added to TFA (25 mL) stirred at 0° C. under argon, followed by dropwise addition of a solution the compound of Preparation X(d) (3 g, 7 mmol) in $CH_2Cl_2$ (25 mL). After the addition was complete, the solution was allowed to warm to RT and was stirred for 2 h. The mixture was concentrated and the residue was dissolved in EtOAc. The organic phase was extracted with concentrated $NH_4OH$ to bring the pH of the aqueous phase to 10. The aqueous layer was washed twice with EtOAc, brought to pH 4 with 3N HCl, and extracted with EtOAc. The organic phase was washed with brine, dried ($MgSO_4$), and concentrated to give the title compound as an off-white solid (2.1 g, 81%): MS (ES) m/e 361.1 $[M+H]^+$.

Preparation Y

Preparation of N-(6-Methyl-2-pyridinyl) ethylenediamine

Following the procedure of Preparation V, except substituting 6-methyl-2-chloropyridine-N-oxide for 2-chloropyridine-N-oxide, gave the title compound: MS (ES) m/e 152 $[M+H]^+$.

Preparation Z

Preparation of N-Methyl-N'-(2-pyridinyl) ethylenediamine a) N-Boc-N-Methyl-N'-(2-pyridinyl)ethylenediamine A mixture of N-Boc-N-(methyl)ethylenediamine (*Synth. Commun.* 1993, 23, 2443–2449)(849.2 mg, 4.87 mmol), 2-chloropyridine N-oxide hydrochloride (970 mg, 5.84 mmol), and $NaHCO_3$ (2.05 g, 24.4 mmol) in tert-amyl alcohol (12 mL) was heated at reflux under argon. After 41.5 h, the reaction was cooled, diluted with EtOH, filtered, and concentrated. The residue was reconcentrated from toluene and chromatographed (silica gel, 5% $CH_3OH/CHCl_3$) to give the title compound as a viscous, yellow oil which was used without further purification (863.1 mg, 66%), MS (ES) m/e 268 $[M+H]^+$.

b) N-Boc-N-methyl-N'-(2-pyridinyl)ethylenediamine

A briskly stirred mixture of the compound of Preparation Z(a) (863.1 mg, 3.23 mmol), ammonium formate (1.02 g, 16.2 mmol), and 10% Pd/C (344 mg, 0.32 mmol) in absolute EtOH (16 mL) was heated at reflux. After 8 h, the reaction was cooled to RT, and more ammonium formate (2.04 g, 32.4 mmol) and 10% Pd/C (3.44 g, 3.23 mmol) were added. The reaction was stirred at 40° C. for 14.5 h, cooled to RT, and filtered through Celite®. The filtrate was concentrated, and the residue was partitioned between $H_2O$ (20 mL) and $CHCl_3$ (20 mL). The phases were separated, the aqueous phase extracted with $CHCl_3$ (2×20 mL), and the combined organic phase was dried ($Na_2SO_4$), and concentrated. The resulting yellow oil was chromatographed (silica gel, 5% $CH_3OH$ in 1:1 EtOAc/$CHCl_3$) to give the title compound as a pale yellow oil (267.4 mg, 33%): MS (ES) m/e 252 $[M+H]^+$.

c) N-methyl-N'-(2-pyridinyl)ethylenediamine dihydrochloride

4 M HCl in dioxane (5.3 mL, 21.2 mmol) was added in a stream to a solution of the compound of Preparation Z(b) (267.4 mg, 1.06 mmol) in anhydrous $CH_2Cl_2$ (5.3 mL) at 0° C. The reaction was stirred at RT for 16 h and concentrated to afford the title compound as a yellow, hygroscopic solid (229.4 mg, 97%): MS (ES) m/e 152 $[M+H^+$.

Preparation AA

Preparation of N-(2-Pyrimidinyl)ethylenediamine a)N-Boc-N'-(2-Pyrimidinyl)ethylenediamine N-(Boc)ethylenediamine (0.80 g, 5.0 mmol) (*Syn. Commun.* 1990, 20, 255–264) was dissolved in 1-propanol (12 mL) and treated with $K_2CO_3$ (1.2 g, 9.0 mmol), followed by 2-chloropyrimidine (0.91 g, 8.0 mmol), and the mixture was heated to reflux for 24 h. The reaction mixture was poured into $H_2O$ (30 mL) and extracted with EtOAc (3×30 mL). The combined organic fractions were dried ($MgSO_4$) and concentrated to give the title compound as a yellow solid (1.6 g): MS (ES) m/e 238.9 $[M+H]^+$.

b) N-(2-Pyrimidinyl)ethylenediamine hydrochloride

The compound of Preparation AA(a) (1.6 g, 6.7 mmol) was dissolved in $CH_2Cl_2$ (6 mL) and treated with 4M HCl in dioxane (1.67 mL). The reaction mixture was stirred 2 h, concentrated, and azeotroped with $CH_2Cl_2$ (3×10 mL) to yield the title compound as a yellow salt (1.2 g, 100%): MS (ES) m/e 139.0 $[M+H]^+$.

Preparation BB

Preparation of N-(6-Methyl-3-pyridazinyl) ethylenediamine a) N-Acetyl-N'-(6-methyl-3-pyridazinyl)ethylenediamine A mixture of 3-chloro-6-methylpyridazine (1.29 g, 10 mmol), N-(acetyl)ethylenediamine (638 mg, 6.25 mmol) and $NaHCO_3$ (1.6 g) in dry DMF (10 mL) was heated at reflux under argon for 20 h. The mixture was filtered, the filtrate concentrated, and the residue was dissolved in $CH_2Cl_2$ and purified by flash chromatography (silica gel, step gradient, 0–8% $CH_3OH/CH_2Cl_2$) to yield the title compound as a yellow solid (700 mg, 44%): MS (ES) m/e 195.0 $[M+H]^+$.

b) N-(6-Methyl-3-pyridazinyl)ethylenediamine

A mixture of the compound of Preparation BB(a) (700 mg, 3.6 mmol) and concentrated HCl (10 mL) was heated to 90° C. for 48 h. The reaction mixture was concentrated and triturated with $Et_2O$ to give the title compound as a purple solid (691 mg): MS (ES) m/e 152.9 $[M+H]^+$.

Preparation CC

Preparation of N-(3-Pyridazinyl)ethylenediamine a) 3-Chloropyridazine 3-(2H)-Pyridazinone (1 g, 10.4 mmol) was treated with phosphorous oxychloride (10 mL) at 90° C. for 4 H. The mixture was poured into ice (100 g), basified with 50% NaOH, and extracted with $CH_2Cl_2$ (3×150 mL). The combined organic extracts were dried (MgSO4) and concentrated to give the title compound as a yellow solid (750 mg, 63%): MS (ES) m/e 115 $[M+H]^+$.

b) N-Acetyl-N'-(3-pyridazinyl)ethylenediamine

A mixture of the compound of Preparation CC(a) (750 mg, 6.6 mmol), N-(acetyl)ethylenediamine (673 mg, 6.6 mmol), and $NaHCO_3$ (2 g) in dry DMF (10 mL) was refluxed under argon for 20 h. The mixture was filtered, the filtrate concentrated, and the residue was dissolved in $CH_2Cl_2$ and purified by flash chromatography (silica gel, step gradient, 0–8% $CH_3OH/CH_2Cl_2$) to give the title compound as a yellow solid (710 mg, 60%): MS(ES) m/e 180.8 $[M+H]^+$.

c) N-(3-Pyridazinyl)ethylenediamine

A mixture of compound of Preparation CC(b) (700 mg, 3.9 mmol) and concentrated HCl (10 mL) was heated to 90° C. for 72 h. The reaction mixture was concentrated and triturated with $Et_2O$ to yield the title compound as a yellow solid: MS(ES) m/e 138.1 $[M+H]^+$.

EXAMPLES

EXAMPLE 1

Preparation of (S)-2,3,4,5-Tetrahydro-4-methyl-3-oxo-7-[[[2-[2-(pyridinyl)amino]ethyl]amino]carbonyl]-1H-1,4-benzodiazepine-2-acetic Acid a) Methyl (S)-2,3,4,5-tetrahydro-4-methyl-3-oxo-7-[[[2-[2-(pyridinyl)amino]ethyl]amino]carbonyl]-1H-1,4-benzodiazepine-2-acetate A mixture of the compound of Preparation V(c) (0.15 g, 1.1 mmol), methyl (S)-7-carboxy-2,3,4,5-tetrahydro-4-methyl-3-oxo-1H-1,4-benzodiazepine-2-acetate (0.325 g, 1.1 mmol), HOBT (0.19 g, 1.3 mmol), EDC (0.27 g, 1.3 mmol), and DIEA (1.6 mL, 9 mmol) in $CH_3CN$ (5 mL) was stirred RT for 4 d. The mixture was concentrated, and the residue was partitioned between EtOAc and $H_2O$. The aqueous layer was extracted twice with EtOAc and the combined organic extract was washed with brine, dried ($MgSO_4$), and concentrated. The residue was purified by chromatography (silica gel, step gradient, 2%–5% $CH_3OH/CH_2Cl_2$) to give the title compound as a colorless foam (0.175 g, 39%): MS (ES) m/e 412.4 $[M+H]^+$.

b) (S)-2,3,4,5-Tetrahydro-4-methyl-3-oxo-7-[[[2-[2-(pyridinyl)amino]ethyl]amino]carbonyl]-1H-1,4-benzodiazepine-2-acetic acid A solution of the compound of Example 1(a) (0.175, 0.42 mmol), $LiOH.H_wO$ (0.027 g, 0.65 mmol), THF (5 mL), and water (5 mL) was stirred at RT overnight. The mixture was concentrated and the residue was dissolved in $H_2O$. The aqueous solution was extracted with EtOAc and brought to pH 5 with 3N HCl. The solution was warmed briefly and allowed to stand overnight. The resulting crystals were collected by filtration and dried to give the title compound as a white solid (0.13 g, 77%): MS (ES) m/e 398.4 $[M+H]^+$. Anal. Calcd for $C_{20}H_{23}N_5O_4$.5/8 $H_2O$: C, 58.78; H, 5.98; N, 17.14. Found C, 58.65; H, 6.03; N, 16.96.

EXAMPLE 2

Preparation of (S)-2,3,4,5-Tetrahydro-4-methyl-3-oxo-7-[[[2-[(1-oxo-2-pyridinyl)amino]ethyl]amino]carbonyl]-1H-1,4-benzodiazepine-2-acetic acid a) Methyl (S)-2,3,4,5-tetrahydro-4-methyl-3-oxo-7-[[[2-(1-oxo-2-pyridinyl) amino]ethyl]amino]carbonyl]-1H-1,4-benzodiazepine-2-acetate Following the procedure of Example 1(a), except substituting the compound of Preparation V(b) for the compound of Preparation V(c), gave the title compound as a colorless foam: MS (ES) m/e 428.4 $[M+H]^+$.

b) (S)-2,3,4,5-Tetrahydro-4-methyl-3-oxo-7-[[[2-[(1-oxo-2-pyridinyl)amino]ethyl]amino]carbonyl]-1H-1,4-benzodiazepine-2-acetic acid Following the procedure of Example 1(b), except substituting the compound of Example 2(a) for the compound of Example 1(a), gave the title compound: MS (ES) m/e 414.5 $[M+H]^+$. Calculated for $C_{20}H_{23}N_5O_5$. 5 $H_2O$: C, 56.86; H, 5.73; N, 16.58. Found C, 56.63; H, 5.67; N, 16.32.

EXAMPLE 3

Preparation of (S)-2,3,4,5-Tetrahydro-3-oxo-7-[[[2-[2-(pyridinyl)amino]ethyl]amino]carbonyl]-1H-1,4-benzodiazepine-2-acetic acid a) Methyl (S)-2,3,4,5-Tetrahydro-3-oxo-7-[[[2-[2-(pyridinyl)amino]ethyl]amino]carbonyl]-1H-1,4-benzodiazepine-2-acetate A mixture of the compound of Preparation W(d) (720 mg, 2 mmol), the compound of Preparation V(c) (672 mg, 3 mmol), DIEA (1.8 mL, 10 mmol), and $(Ph_3P)_2PdCl_2$ (140 mg, 0.2 mmol) in N-methyl-2-pyrrolidinone (20 mL) was heated to 110° C. under CO balloon for 3 h. The mixture was concentrated and the residue was purified by flash chromatography (silica gel, step gradient, 0–7% $CH_3OH/CH_2Cl_2$) to give the title compound as a pale yellow semisolid; MS (ES) m/e 398.2 $[M+H]^+$.

b) (S)-2,3,4,5-Tetrahydro-3-oxo-7-[[[2-[2-(pyridinyl)amino]ethyl]amino]carbonyl]-1H-1,4-benzodiazepine-2-acetic acid 1M LiOH (3.8 mL, 3.8 mmol) was added dropwise to a solution of the compound of Example 3(a) (1 g, 2.5 mmol) in 1:1 $CH_3OH$:THF (20 mL) at RT. The resulting mixture was stirred for 20 h and concentrated. The residue was dissolved in $H_2O$, acidified with TFA (20%), and purified by chromatography (ODS, 6% $CH_3CN/H_2O$-0.1% TFA). Fractions containing the desired product were pooled, concentrated, and lyophilized to give the title compound [may contain approximately 23% of the R-enantiomer, see Preparation W (c)] as a pale yellow powder: MS (ES) m/e 384.2 $[M+H]^+$; Anal. Calcd for $C_{19}H_{21}N_5O_4$.2.5 TFA; C,41.87; H, 3.44; N,10.17. Found: C, 42.01; H, 3.62; N, 10.15.

EXAMPLE 4

Preparation of (S)-2,3,4,5-Tetrahydro-3-oxo-7-[[2-[2-(pyridinyl)amino]ethyl]amino]carbonyl]-4-(2,2,2-trifluoroethyl)-1H-1,4-benzodiazepine-2-acetic acid a) Methyl (S)-2,3,4,5-tetrahydro-3-oxo-7-[[[2-[2-(pyridinyl)amino]ethyl]amino]carbonyl]-4-(2,2,2-trifluoroethyl)-1H-1,4-benzodiazepine-2-acetate Following the procedure of Example 1(a), except substituting the compound of Preparation X(e) for methyl (S)-7-carboxy-2,3,4,5-tetrahydro-4-methyl-3-oxo-1H-1,4-benzodiazepine-2-acetate, gave the title compound as a white foam: MS (ES) m/e 479.7 $[M+H]^+$.

b) (S)-2,3,4,5-Tetrahydro-3-oxo-7-[[[2-[2-(pyridinyl)amino]ethyl]amino]carbonyl]-4-(2,2,2-trifluoroethyl)-1H-1,4-benzodiazepine-2-acetic acid Following the procedure of Example 1(b), except substituting the compound of Example 4(a) for the compound of Example 1(a), gave the title compound as white solid: MS (ES) m/e 466.1 $[M+H]^+$. Anal. Calcd for $C_{21}H_{22}F_3N_5O_4$.0.8 $H_2O$: C, 52.56; H, 4.96; N, 14.60. Found C, 52.88; H, 5.00; N, 14.10.

EXAMPLE 5

Preparation of (±)-2,3,4,5-Tetrahydro-3-oxo-4-(phenylethyl)-7-[[[2-[2-(pyridinyl)amino]ethyl]amino]carbonyl]-1H-1,4-benzodiazepine-2-acetic acid a) Methyl (±)-2,3,4,5-tetrahydro-3-oxo-4-(phenylethyl)-7-[[[2-[2-(pyridinyl)amino]ethyl]amino]carbonyl]-1H-1,4-benzodiazepine-2-acetate Methyl (±)-7-carboxy-2,3,4,5-tetrahydro-3-oxo-4-phenylethyl-1H-1,4-benzodiazepine-2-acetate (2 mmol), EDC (0.38 g, 2 mmol), HOBT.$H_2O$ and the compound of Preparation V(c) (1.65 mmol) were combined and stirred at RT overnight. The mixture was concentrated, and the residue was treated with 5% $Na_2CO_3$ and extracted with $CH_2Cl_2$. The combined organic extracts were washed with $H_2O$, dried ($MgSO_4$) and concentrated. The residue was chromatographed to yield the title compound as a white foam: MS (ES) m/e 502 $[M+H]^+$.

b) (±)-2,3,4,5-Tetrahydro-3-oxo-4-(phenylethyl)-7-[[[2-[2-(pyridinyl)amino]ethyl]amino]carbonyl]-1H-1,4-benzodiazepine-2-acetic acid The compound of Example 5(a) (0.16 g, 0.4 mmol) was dissolved in $CH_3OH$ (10 mL) and THF (1 mL), and treated with 1N NaOH (0.5 mL). The mixture was stirred overnight, concentrated, and the residue was dissolved in $H_2O$ and extracted with $CH_2Cl_2$. The pH of the aqueous phase was adjusted to 5.5–6 with dilute HCl, and the solid which formed was filtered, washed with $H_2O$ and $Et_2O$, and dried to give the title compound: MS (ES) m/e 488 $[M+H]^+$. Anal. Calcd for $C_{27}H_{29}N_5O_4$. 0.625 $H_2O$: C, 65.01; H, 6.11; N, 14.04. Found C, 64.95; H, 5.92; N, 13.94.

EXAMPLE 6

Preparation of (S)-2,3,4,5-Tetrahydro-4-methyl-7-[[[2-[2-(6-methyl-pyridinyl)amino]ethyl]amino]carbonyl]-3-oxo-1H-1,4-benzodiazepine-2-acetic Acid a) Methyl (S)-2,3,4,5-Tetrahydro-4-methyl-7-[[[2-[2-(6-methyl-pyridinyl)amino]ethyl]amino]carbonyl]-3-oxo-1H-1,4-benzodiazepine-2-acetate Following the procedure of Example 5(a), except substituting the compound of Preparation Y for the compound of Preparation V(c), gave the title compound: MS (ES) m/e 426 $[M+H]^+$.

b) (S)-2,3,4,5-Tetrahydro-4-methyl-7-[[[2-[2-(6-methyl-pyridinyl)amino]ethyl]amino]carbonyl]-3-oxo-1H-1,4-benzodiazepine-2-acetic acid Following the procedure of Example 5(b), except substituting the compound of Example 6(a) for the compound of Example 5(a), gave the title compound: MS (ES) m/e 412 $[M+H]^+$. Anal. Calcd for $C_{21}H_{25}N_5O_4$. 0.5 $H_2O$: C, 59.99; H, 6.23; N, 16.66. Found C, 59.69; H, 6.15; N, 16.37.

EXAMPLE 7

Preparation of (S)-2,3,4,5-Tetrahydro-4-methyl-3-oxo-7-[[[2-[2-(pyridinyl) amino]ethyl]methylamino]carbonyl]-1H-1,4-benzodiazepine-2-acetic acid a) Methyl (S)-2,3,4,5-tetrahydro-4-methyl-3-oxo-7-[[[2-[2-(pyridinyl)amino]ethyl]methylamino]carbonyl]-1H-1,4-benzodiazepine-2-acetate EDC (195.5 mg, 1.02 mmol) was added to a solution of methyl (S)-7-carboxy-2,3,4,5-tetrahydro-4-methyl-3-oxo-1H-1,4-benzodiazepine-2-acetate (248.4 mg, 0.85 mmol), the compound of Preparation Z(c) (229.4 mg, 1.02 mmol), HOBt.$H_2O$ (137.8 mg, 1.02 mmol), and DIEA (0.74 mL, 4.25 mmol) in anhydrous $CH_3CN$ (4.3 mL) at RT. After 21 h, the reaction was concentrated and the residue was chromatographed (silica gel, 10% $CH_3OH/CHCl_3$) to give the title compound as a light yellow foam (353.8 mg, 98%): MS (ES) 426 $[M+H]^+$.

b) (S)-2,3,4,5-Tetrahydro-4-methyl-3-oxo-7-[[2-[2-(pyridinyl)amino]ethyl]methylamino]carbonyl]-1H-1,4-benzodiazepine-2-acetic acid 1N LiOH (1.0 mL, 1.0 mmol) was added all at once to a solution of the compound of Example 7(a) (353.8 mg, 0.83 mmol) in THF (4.2 mL) and $H_2O$ (3.2 mL) at RT. After 0.5 h, the reaction was concentrated to dryness and the residue was dissolved in $H_2O$ (4 mL). The solution was extracted with EtOAc (2×4 mL) and the EtOAc layers were discarded. The aqueous solution was acidified to pH 6 with 1.0N HCl and allowed to stand at 5° C. overnight. The solution was chromatographed (ODS, 12% $CH_3CN/H_2O$-0.1% TFA) and the fractions containing the desired product were pooled, concentrated and lyophilized to give the title compound as a colorless powder (399.7 mg, 81%): MS (ES) m/e 412 $[M+H]^+$. Anal. Calcd for $C_{21}H_{25}N_5O_4$. 1.5 TFA . 0.75 $H_2O$: C, 48.37; H, 4.74; N, 11.75. Found: C, 48.25; H, 4.89; N, 11.86.

EXAMPLE 8

Preparation of (±)-2,3,4,5-Tetrahydro-4-methyl-3-oxo-7-[[[2-[2-(pyrimidinyl)amino]ethyl]amino]crbonyl]-1H-1,4-benzodiazepine-2-acetic acid a) Methyl (±)-2,3,4,5-tetrahydro-4-methyl-3-oxo-7-[[[2-[(2-pyrimidinyl)amino]ethyl]amino]carbonyl]-1H-1,4-benzodiazepine-2-acetate The compound of Preparation AA(b) (1.2 g, 6.7 mmol), methyl (±)-7-carboxy-2,3,4,5-tetrahydro-4-methyl-3-oxo-1H-1,4-benzodiazepine-2-acetate (1.8 g, 6.1 mmol), EDC (1.7 g, 9.2 mmol), and DIEA (3.7 mL, 21.4 mmol) were dissolved in DMF (35 mL) and the mixture was stirred at RT for 24 h. The mixture was poured into 5% $NaHCO_3$ (50 mL) and extracted with EtOAc (3×30 mL). The combined organic extract was washed with $H_2O$ (4×50 mL), dried ($MgSO_4$), and concentrated. The residue was chromatographed (silica gel, 3% $CH_3OH/CH_2Cl_2$) to yield the title compound (300 mg, 12%). Additional purification was obtained by preparative HPLC (ODS-AQ, 50×250 mm, 80 mL/min, 14% $CH_3CN/H_2O$-0.1% TFA, UV detection at 220 nm): MS (ES) m/e 412.9 $[M+H]^+$; $^1H$ NMR (400 MHz, DMSO-$d_6$) δ 8.28 (d, J=2 Hz, 2H), 8.18 (bt, 1H), 7.51 (m, 2H), 7.19 (bt, 1H), 6.57 (t, J=9.3 Hz, 1H), 6.53 (d, J=8 Hz, 1H), 6.32 (d, J=2 Hz, 1H), 5.50 (d, J=16 Hz, 1H), 5.14 (m, 1H), 3.84 (d, J=16 Hz, 1H), 3.38 (s, 4H), 2.81 (dd, J=16.9 Hz, 1H), 2.67 (dd, J=17.4 Hz, 1H), Anal. Calcd for $C_{20}H_{24}N_6O_4$. 1.5 TFA: C, 47.34; H, 4.40; N, 14.40 Found: C, 47.21; H, 4.49; N, 14.13.

b) (±)-2,3,4,5-Tetrahydro-4-methyl-3-oxo-7-[[[2-[(2-pyrimidinyl)amino]ethyl]amino]carbonyl]-1H-1,4-benzodiazepine-2-acetic acid The compound of Example 8(a) was dissolved in $CH_3OH$ (5 mL) containing 1N NaOH (3.4 mL) and $H_2O$ (2 mL) and the mixture was stirred, concentrated, and purified by preparative HPLC (ODS-AQ, 50×250 mm, 80 mL/min, 14% $CH_3CN/H_2O$-0.1% TFA, UV detection at 220 nm) to yield the title compound as a white solid (80 mg, 35%): MS (ES) m/e 399.1 $[M+H]^+$; $^1H$ NMR (400 MHz, DMSO-$d_6$) δ 8.30 (d, J=3 Hz, 2H), 8.15 (bt, 1H), 7.50 (m, 2H), 7.23 (bt, 1H), 6.57 (t, J=7.3 Hz, 1H), 6.52 (d, J=8 Hz, 1H), 6.30 (d, J=3 Hz, 1H), 5.49 (d, J=18 Hz, 1h), 5.08 (m, 1H), 3.84 (d, J=19 Hz, 1H), 3.43 (s, 4H), 2.81 (d, J=19.9 Hz, 1H), 2.55 (d, 1H), Anal. Calcd for $C_{19}H_{22}N_6O_4$: C, 57.28; H, 5.57: N, 21.09. Found: C, 57.59; H, 5.43; N, 20.97.

EXAMPLE 9

Preparation of (±)-2,3,4,5-Tetrahydro-4-methyl-7-[[2-[(6-methyl-3-pyridazinyl)amino]ethyl]amino]carbonyl]-3-oxo-1H-1,4-benzodiazepine-2-acetic acid (SB 240375)

a) Methyl (±)-7-[[[2-[(6-Methyl-3-pyridazinyl)amino]ethyl]amino]carbonyl]-3-oxo-1H-1,4-benzodiazepine-2-acetate EDC (759 mg, 3.96 mmol) was added to a solution of the compound of Preparation BB(b) (3.6 mmol), methyl (±)-7-carboxy-2,3,4,5-tetrahydro-4-methyl-3-oxo-1H-1,4-benzodiazepine-2-acetate (1.05 g, 3.6 mmol), HOBT.$H_2O$ (535 mg, 3.96 mmol), and DIEA (2.07 mL, 11.88 mmol) ion anhydrous DMF at RT. After 20 h, the reaction was concentrated, and the residue was dissolved in $CH_2Cl_2$ and chromatographed (silica gel, step gradient 0–10%, $CH_3OH$/$CH_2Cl_2$) to give the title compound as a pale yellow solid (960 mg, 63%): MS(ES) m/e 427 $[M+H]^+$.

B) (±)-2,3,4,5-Tetrahydro-4-methyl-7-[[[2-[(6-methyl-3-pyridazinyl)amino]ethyl]amino]carbonyl]-3-oxo-1H-1,4-benzodiazepine-2-acetic acid 1M NaOH (4.0 mL, 4.0 mmol) was added dropwise to a solution of the compound of Example 9(a) (800 mg, 1.94 mmol) in 1:1 $CH_3OH$:THF (20 mL) at RT. The resulting mixture was stirred for 20 h, concentrated, and the residue was dissolved in $H_2O$, acidified with 20% TFA, and chromatographed (ODS, step gradient, 5–7% $CH_3CN/H_2O$-0.1% TFA) to give the title compound as a white powder: MS(ES) m/e 413.2 $[M+H]^+$. Anal. Calcd for $C_{20}H_{24}N_6O_4$. 1.5 TFA . 0.75 $H_2O$: C, 46.27; H, 4.56; N, 14.08. Found: C, 46.04; H, 4.27; N, 13.78.

EXAMPLE 10

Preparation of (±)-2,3,4,5-Tetrahydro-4-methyl-3-oxo-7-[[2-[3-(pyridazinyl)amino]ethyl]amino]carbonyl]-1H-1,4-benzodiazepine-2-acetic acid a) Methyl (±)-2,3,4,5-tetrahydro-4-methyl-3-oxo-7-[[[2-[3-(pyridazinyl)amino]ethyl]amino]carbonyl]-1H-1,4-benzodiazepine-2-acetic acid Following the procedure of Example 9(a), except substituting the compound of Preparation CC(c) for the compound of Preparation BB(b), gave the title compound as a pale yellow solid (1.12 g, 76%). A 200 mg sample was purified further by chromatography (ODS, 10% $CH_3CN/H_2O$-0.1% TFA): MS(ES) m/e 413.2 $[M+H]^+$. Anal. Calcd for $C_{20}H_{24}N_6O_4$. 1.5 TFA . 0.5 $H_2O$: C, 46.63; H, 4.51; N, 14.18. Found: C, 46.54; H, 4.65; N, 14.46.

b) (±)-2,3,4,5-Tetrahydro-4-methyl-3-oxo-7-[[[2-[3-(pyridazinyl)amino]ethyl]amino]carbonyl]-1H-1,4-benzodiazepine-2-acetic acid Following the procedure of Example 9(b), except substituting the compound of Example 10(a) for the compound of Example 9(a), gave the title compound as a white powder: MS(ES) m/e 399.2 $[M+H]^+$. Anal. Calcd for $C_{19}H_{22}N_6O_4$. 1.5 TFA. $H_2O$: C, 44.98; H, 4.37; N, 14.31. Found: C, 44.82; H, 4.3; N, 14.31.

EXAMPLE 11

Preparation of 3-[3,4-Dihydro-8-[[[(2-pyridinyl)-2-aminoethyl]amino]carbonyl]-1-methyl-2,5-dioxo-1H-1,4-benzodiazepine]-4-propanoic acid A) Benzyl 3-[3,4-dihydro-8-[[[(2-pyridinyl)-2-aminoethyl]amino]carbonyl]-1-methyl-2,5-dioxo-1H-1,4-benzodiazepine]-4-propanoate EDC (0.25 g, 1.3 mmol) is added to a solution of the compound of Preparation A(f) (1.1 mmol), the compound of Preparation V(c) (1.1 mmol), HOBT.$H_2O$ (170 mg, 1.3 mmol), and DIEA (0.9 mL, 4.4 mmol) ion anhydrous $CH_3CN$ (5 mL) at RT. After 21 h, the reaction is concentrated and the residue is purified by chromatography (silica gel) to afford the title compound.

b) 3-[3,4-dihydro-8-[[[(2-pyridinyl)-2-aminoethyl]amino]carbonyl]-1-methyl-2,5-dioxo-1H-1,4-benzodiazepine]-4-propanoic acid A mixture of the compound of Example 11(a) (2 mmol) and 10% Pd/C (0.02 g) in EtOH (100 mL) is hydrogenated in an atmosphere of $H_2$ (50 psi) for 6 h. The catalyst is removed by filtration, and the filtrate is concentrated to afford the title compound.

EXAMPLE 12

Preparation of 3-[4H-Imidazo[1,2-a][1,4]benzodiazepine-5(6H)-1-methyl-6-oxo-9-[[[(2-pyridinyl)-2-aminoethyl]amino]carbonyl]-5-propanoic acid A) Ethyl 3-[4H-imidazo[1,2-a][1,4]benzodiazepine-5(6H)-1-methyl-6-oxo-9-[[[(2-pyridyl)-2-aminoethyl]amino]carbonyl]-5-propanoate EDC (0.25 g, 1.3 mmol) is added to a solution of the compound of Preparation B(e) (1.1 mmol), the compound of Preparation V(c) (1.1 mmol), HOBT.$H_2O$ (170 mg, 1.3 mmol), and DIEA (0.9 mL, 4.4 mmol) in anhydrous $CH_3CN$ (5 mL) at RT. After 21 h, the reaction is concentrated and the residue is purified by chromatography (silica gel) to afford the title compound.

b) 3-[4H-Imidazo[1,2-a[1,4]benzodiazepine-5(6H)-1-methyl-6-oxo-9-[[[(2-pyridinyl)-2-aminoethyl]amino]carbonyl]-5-propanoic acid A solution of the compound of Example 12(a) (54 mmol), LiOH.$H_2O$ (0.79 mmol), THF (5 mL), and $H_2O$ (2 mL) is stirred at RT overnight. The mixture is concentrated and the residue is dissolved in water. The resulting solution is brought to pH 5 with 3N HCl to afford the title compound.

EXAMPLE 13

Preparation of 4-[4-[3-(2-Pyridinyl)amino]propyl]-1-piperazinyl]-1-piperidineacetic acid a) Ethyl 4-[4-[3-(2-pyridinyl)amino]propyl]-1-piperazinyl]-1-piperidineacetate A mixture of the compound of Preparation C(b), the compound of Preparation D(c), and DIEA in THF is stirred at RT for 4 h. The mixture is diluted with aqueous $NaHCO_3$ and extracted with EtOAc. The organic phase is dried ($Na_2SO_4$) and concentrated to give the title compound.

b) 4-[4-[3-(2-Pyridinyl)amino]propyl]-1-piperazinyl]-1-piperidineacetic acid

A solution of the compound of Example 13(a) and aqueous NaOH in $CH_3OH$ is stirred at RT. After 18 h, the mixture is neutralized with HOAc, desalted through an XAD-2 column, and lyophilized to give the title compound.

EXAMPLE 14

Preparation of 1-Hydroxyl 4-[4-[3-(2-pyridinyl)amino]propyl]-1-piperazinyl]cyclohexaneacetic acid Following the general procedure of Example 13, except substituting 1,1-dimethylethyl 1-hydroxyl-4-(1-piperazinyl)cyclohexaneacetate for the compound of Preparation C(b) gives the title compound.

EXAMPLE 15

Preparation of 4-[4-[2-(2-Pyridinyl)amino]ethyl]-1-piperazinyl]-1-piperidineacetic acid a) Ethyl 4-[4-[2-(1-oxo-2-pyridinyl)amino]ethyl]-1-piperazinyl]-1-piperidineacetate The compound of Preparation E(b), 2-chloropyridine-N-oxide, and $NaHCO_3$ in butanol is heated. The mixture is cooled, filtered, and the filtrate is concentrated. The residue is partitioned between $H_2O$ and EtOAc and the organic phase is dried ($Na_2SO_4$) and concentrated. The residue is purified by chromatography (silica gel) to give the title compound.

b) Ethyl 4-[4-[2-(2-pyridinyl)amino]ethyl]-1-piperazinyl]-1-piperidineacetate

The compound of Example 15(a), potassium formate, 10% Pd/C and $CH_3OH$ was heated, cooled, filtered and concentrated. The residue was chromatographed (silica gel) to give the title compound.

c) 4-[4-[2-(2-Pyridinyl)amino]ethyl]-1-piperazinyl]-1-piperidineactic acid

The compound of Example 15(b) and 1N NaOH in $CH_3OH$ is stirred. The mixture is adjusted to pH 5 with dilute HCl and concentrated to give the title compound.

EXAMPLE 16

Preparation of 1-Hydroxyl 4-[4-[2-(2-pyridinyl)amino]ethyl]-1-piperazinyl]cyclohexaneacetic acid Following the procedure of Example 15, except substituting the compound of Preparation F for the compound of Preparation E(b), gives the title compound.

EXAMPLE 17

Preparation of N-[3-[1-[[[(2-Pyridinyl)amino]propyl]carbonyl]-3-piperidinyl]carbonyl]-β-alanine Following the procedures of Beavers, et al., WO 95/25091, Example 1, except substituting the compound of Preparation G, for $N^{\alpha}$-Boc-D-lys(Cbz)-OH, gives the title compound.

EXAMPLE 18

Preparation of 5-[2-(Carboxy-ethyl)amino]carbonyl]-2-[2[(2-pyridinyl)amino]ethyl]-2,3-dihydro-3-oxo-1H-isoindole Following the procedures of Preparation 1–12 in Hartman, et al., EP 0 540 334 A1, for the preparation of 2,3-dihydro-N-(2-carboxy-ethyl)-2-[2-(piperidinyl)ethyl]-3-oxo-1H-isoindole-5-carboxamide, except substituting the compound of Preparation V(c) for N-Boc-4-piperidine-2-ethylamine, the title compound is prepared.

EXAMPLE 19

Preparation of (S)-2-(Butylsulfonylamino)-3-[4-[4-(N-pyrid-2-ylamino)]]butyloxy phenylpropionic acid Following the procedures of Egbertson, et al., EP 0478363 A2, for the preparation of (S)-2-(butylsulfonylamino)-3-[4-(N-benzyloxycarbonylpiperidin-4-yl)-2,2-dimethyl]butyloxyphenylpropionic acid, except substituting the compound of Preparation H(b) for 4-[4-(N-benzyloxycarbonylpiperidin-4-yl)-2-methyl]pentan-2-ol, the title compound is prepared.

EXAMPLE 20

Preparation of N-[3(R)-[3-[(2-Pyridinyl)amino]propyl]-2-oxo-1-piperidinyl]acetyl]-3(R)-methyl-β-alanine Following the procedure of Duggan, et al., J. Med. Chem., 1995, 38, 3332, except substituting the compound of Preparation I(c) instead of (N-Boc-piperidin-4-yl)butanoic acid, the title compound is prepared.

EXAMPLE 21

Preparation of 3-[[3-[3-[(2-Pyridinyl)amino]propyl]isoxazolin-5(R,S)-yl]acetyl]amino-3(R,S)-methylpropanoic acid a) 4-[N-Pyrid-2-yl-N-(toluenesulfonyl)amino]butanoximinoyl chloride Following the procedure of WO 95/14682, Example 1(b), except substituting the compound of Preparation J(e) for 4-cyanobenzoxime, the title compound is prepared.

b) tert-Butyl [3-[3-[N-pyrid-2-yl-N-(toluenesulfonyl)amino]propyl]isoxazolin-5(R,S)-yl]acetate Following the procedure of WO 95/14682, Example 1(d), except substituting the compound of Example 21(a) for 4-cyanobenzoximinoyl chloride, and substituting tert-butyl 3-butenoate for the methyl 3-butenoate, the title compound is prepared.

c) [3-[3-[N-Pyrid-2-yl-N-(toluenesulfonyl)amio]propyl]isoxazolin-5(R,S)-yl]acetic acid 4M HCl in dioxane (10 mL) is added to a solution of the compound of Example 21(b) (5 mmol) in $CH_2Cl_2$ (40 mL) at 0° C. The reaction is stirred at RT until complete and is concentrated to afford the title compound.

d) Ethyl 3-[[3-[3-[N-pyrid-2-yl-N-(toluenesulfonyl)amino]propyl]isoxazolin-5(R,S)-yl]acetyl]amino-3(R,S)-methylpropanoate EDC (1.2 mmol) is added to a solution of the compound of Example 21(c) (1 mmol), ethyl 3-(R,S)-aminobutyrate (1.2 mmol), HOBt . $H_2O$ (1.2 mmol), and DIEA (4 mmol) in anhydrous $CH_3CN$ (5 mL) at RT. The reaction is stirred at RT until complete, and is concentrated. The residue is purified by chromatography (silica gel) to afford the title compound.

e) 3-[[3-[3-[(2-Pyridinyl)amino]propyl]isoxazolin-5(R,S)-yl]acetyl]amino-3-(R,S)-methylpropanoic acid 1.0N LiOH (2.5 mmol) is added to a solution of the compound of Example 21(d) (0.5 mmol) in THF (2.5 mL). The reaction is stirred at RT until complete, then is neutralized with 1.0N HCl. The solution is concentrated and the residue is purified by reverse-phase chromatography to afford the title compound.

EXAMPLE 22

Preparation of N-[3-[[[2-[2-(Pyridinyl)amino]ethyl]carbonyl]amino]benzoyl]-β-alanine a) Benzyl N-[3-[[[2-[2-(pyridinyl)amino]ethyl]carbonyl]amino]benzoyl]-β-alaninate A mixture of benzyl N-(3-aminobenzoyl)-β-alaninate, Alig, et. al., EP 0372486, (1 mmol), N-(2-pyridinyl)-β-alanine, Chowdhary, et al., Indian J. Chem., 1990, 29A, 280–284, (1 mmol), EDC (1.5 mmol) and DIEA (3 mmol) in DMF (25 mL) is stirred at RT. The mixture is poured into 5% $NaHCO_3$ and extracted with EtOAc. The combined organic phase is washed with $H_2O$, dried ($MgSO_4$) and concentrated. The residue is chromatographed (silica gel) to give the title compound.

b) N-[3-[[[2-[2-(Pyridinyl)amino]ethyl]carbonyl]amino]benzoyl]-β-alanine

A mixture of the compound of Example 22(a) (1 mmol) and 1N NaOH (1.5 mL) in $CH_3OH$ (20 mL) is stirred and concentrated. The residue is dissolved in $H_2O$, extracted with $CH_2Cl_2$, and the aqueous phase is adjusted to pH 5 with dilute HCl to give the title compound.

EXAMPLE 23

Preparation of [[1-[N-[[2-[(2-Pyridinyl)amino]ethyl]carbonyl]tyrosyl]-4-piperidinyl]oxy]acetic acid a) tert-Butyl [[1-[N-[[2-[(2-pyridinyl)amino]ethyl]carbonyl]tyrosyl]-4-piperidinyl]oxy]acetate A mixture of tert-butyl [(1-tyrosyl-4-piperidinyl)oxy]acetate, Alig, et. al., EP 372486, (1 mmol), N-(2-pyridinyl)-β-alanine, Chowdhary, et. al., Indian J. Chem., 1990, 29A, 280–284, (1 mmol), EDC (1.5 mmol), and DIEA (3 mmol) in DMF (25 mL) is stirred at RT. The mixture is poured into 5% $NaHCO_3$ and extracted with EtOAc. The combined orgainic phase is washed with $H_2O$, dried ($MgSO_4$) and concentrated. The residue is chromatographed (silica gel) to give the title compound.

b) [[1-[N-[[2-[(2-Pyridinyl)amino]ethyl]carbonyl]tyrosyl]-4-piperidinyl]oxy]acetate A mixture of the compound of Example 23(a) (1 mmol and $CF_3CO_2H$ in $CH_2Cl_2$ is stirred and concentrated to give the title compound.

EXAMPLE 24

Preparation of (±)-3-[[[[3-[(2-Pyridinyl)amino]propyl]amino]succinoyl]amino]-4-pentynoic acid a) Methyl 4-[[3-[(2-pyridyl)amino]propyl]amino]-4-oxobutyrate 3-Carbomethoxypropionyl chloride (0.74 mL, 6.0 mmol) is added at 0° C. to a stirred solution of the compound of Preparation K(c) (5.0 mmol) and DIEA (4.4 mL, 25 mmol) in dry $CH_2Cl_2$ (50 mL). After stirring for 1.5 h at RT, the reaction mixture is diluted with $CH_2Cl_2$ (50 mL) and washed sequentially with $H_2O$ (25 mL) and 5% $NaHCO_3$ (25 mL). The organic layer is dried ($MgSO_4$), concentrated, and reconcentrated from toluene. Chromatography (silica gel) gives the title compound.

b) 4-[[3-[(2-Pyridyl)amino]propyl]amino]-4-oxobutyric acid

A mixture of the compound of Example 24(a) (530.6 mg, 2.0 mmol), 1.0N LiOH (3.0 mL, 3.0 mmol), THF (10 mL), and $H_2O$ (7 mL) is stirred at RT overnight, then is concentrated. The residue is taken up in $H_2O$ (5 mL) and neutralized with 1.0N HCl. The precipitate is collected and dried in vacuum to give the title compound.

c) Ethyl (±)-[[[[3-[(2-Pyridinyl)amino]propyl]amino]succinoyl]amino]-4-pentynoate EDC (230 mg, 1.2 mmol) is added to a solution of the compound of Example 24(b) (203.3 mg, 1.0 mmol), ethyl (±)-3-amino-4-pentynoate, WO 93/07867, (169.4 mg, 1.2 mmol), HOBt . $H_2O$ (162.2 mg, 1.2 mmol), and DIEA (0.70 mL, 4 mmol) in anhydrous $CH_3CN$ (5 mL) at RT. The reaction is stirred at RT overnight and is concentrated. The residue is chromatographed (silica gel) to give the title compound.

d) (±)-3-[[[[3-[(2-Pyridinyl)amino]propyl]amino]succinoyl]amino]-4-pentynoic acid A mixture of the compound of Example 24(c) (187.2 mg, 0.5 mmol), 1.0N LiOH (0.75 mL, 0.75 mmol), THF (2.5 mL), and $H_2O$ (1.7 mL) is stirred at RT overnight, then is concentrated. The residue is taken up in $H_2O$ (2 mL) and acidified with TFA. ODS chromatography followed by lyophilization of the purified material gives the title compound.

EXAMPLE 25

Preparation of (S)-4-[[[2-[2-(Pyridinyl)amino]ethyl]carbonyl]glycyl]-3-methoxycarbonylmethyl-2-oxopiperazine-1-acetic acid Following the procedure of Sugihara, et. al., EP 0529858, Example 59, except substituting N-(2-pyridinyl)-β-alanine, Chowdhary, et. al., Indian J. Chem., 1990, 29A, 280–284, for 4-amidinobenzoic acid hydrochloride, gives the title compound.

EXAMPLE 26

Preparation of (3S,5S)-3-Carboxymethyl-5-[[4-[2-[2-(pyridinyl)amino]ethyl]phenyl]oxymethyl]-2-pyrrolidinone a) (3S,5S)-3-[(tert-Butoxycarbonyl)methyl]-5-[[4-[2-[2-(pyridinyl)amino]ethyl]phenyl]oxymethyl]-2-pyrrolidinone Following the procedure of Himmelsbach, et.al., AU-A-86926/91, Example 3(51), except substituting the compound of Preparation L for 4'-cyano-3'-fluoro-4-(hydroxy)biphenyl, gives the title compound.

b) (3S,5S)-3-Carboxymethyl-5-[[4-[2-[2-(pyridinyl)amino]ethyl]phenyl]oxymethyl]-2-pyrrolidinone Following the procedure of Himmelsbach, et. al., AI-A-86926/91, Example 7(93), except substituting the compound of Example 26(a) for (3S,5S)-3-[(tert-butyloxycarbonyl)methyl]-5-[(4'-amidino-3'-fluoro-4-biphenylyl)oxymethyl]-2-pyrrolidinone, gives the title compound.

EXAMPLE 27

Preparation of 1-[2-[2-(Pyridinyl)amino]ethyl]-3-[4-(2-carboxyethyl)phenyl]-4-methoxy-3-pyrrolin-2-one Following the procedures of Linz, et. al., EP 0567968, except substituting the compound of Preparation V(c) for 4-cyanoaniline, gives the title compound.

EXAMPLE 28

Preparation of 4-[[[2-[(2-Pyridinyl)amino]ethyl]methylamino]acetyl]phenoxyacetic acid a) Methyl 4-[[[2-[(2-pyridinyl)amino]ethyl]methylamino]acetyl]phenoxyacetate Following the procedure of Wayne et. al., WO 94/22834, Example 1, except substituting the compound of Preparation Z(c) (1 mmol) for 1-(4-pyridyl)piperazine, gives the title compound.

b) 4-[[[2-[(2-Pyridinyl)amino]ethyl]methylamino]acetyl]phenoxyacetic acid

Following the procedure of Wayne et. al., WO 94/22834, Example 2, except substituting the compound of Example 28(a) for methyl 4-[2-[4-(4-pyridinyl)piperazin-1-yl]acetyl]phenoxyacetate, gives the title compound.

EXAMPLE S

Preparation 2,2'-[[4-[[[2-[(2-Pyridinyl)amino]ethyl]methylamino]acetyl]-1,2-phenylene]bis(oxy)]bis-acetic acid a) Dimethyl 2,2'-[[4-[[[2-[(2-pyridinyl)amino]ethyl]methylamino]acetyl]-1,2-phenylene]bis(oxy)]bis-acetate Following the procedure of Wayne et. al., WO 94/22834, Example 3, except substituting the compound of Preparation Z(c) for 1-(4-pyridyl)piperazine, gives the title compound.

b) 2,2'-[[4-[[[2-[(2-Pyridinyl)amino]ethyl]methylamino]acetyl]-1,2-phenylene]bis(oxy)]bis-acetic acid Following the procedure of Wayne et. al., WO 94/22834, Example 4, except substituting the compound of Example S(a) for dimethyl 2,2'-[4-[2-[4-(4-pyridinyl)piperazin-1-yl)acetyl]phenylene-1,2-dioxy]diacetate, gives the title compound.

EXAMPLE 29

Preparation of 4-[[[[2-[(2-Pyridinyl)amino]ethyl]carbonyl]methylamino]acetyl]phenoxyacetic acid a) Methyl 4-[[[[2-[(2-pyridinyl)amino]ethyl]carbonyl]methylamino]acetyl]phenoxyacetate A mixture of the compound of Preparation M(c) (1 mmol), N-(2-pyridinyl)-β-alanine, Chowdhary et. al., Indian J. Chem., 1990, 29A, 280–284, (1 mmol), EDC (1.5 mmol), and DIEA (3 mmol) in DMF (25 mL) is stirred at RT. The mixture is poured in to 5% $NaHCO_3$ and extracted with EtOAc. The organic phase is washed with $H_2O$, dried ($MgSO_4$), and concentrated. The residue is chromatographed (silica gel) to give the title compound.

b) 4-[[[2-[(2-Pyridinyl)amino]ethyl]carbonyl]methylamino]acetyl]phenoxyacetic acid The compound of Example 29(a) (1 mmol) and 1N NaOH (1.5 mL) in $CH_3OH$ (20 mL) is stirred and concentrated. The residue is dissolved in $H_2O$, extracted with $CH_2Cl_2$, and the aqueous phase is adjusted to pH 5 with dilute HCl to give the title compound.

EXAMPLE 30

Preparation 4-[[[[2-[2-(Pyridinyl)amino]ethyl]carbonyl] methylamino]acetyl]-1,2-phenylenedioxydiacetic acid a) Dimethyl 4-[[[[2-[2-(pyridinyl)amino]ethyl]carbonyl] methylamino]acetyl]-1,2-phenylenedioxydiacetate Following the procedure of Example 29(a), except substituting the compound of Preparation N(c) for the compound of Preparation M(c), gives the title compound.

b) 4-[[[[2-[(2-Pyridinyl)amino]ethyl]carbonyl] methylamino]acetyl]-1,2-phenylenedioxydiacetic acid Following the procedure of procedure of Example 29(b), except substituting the compound of Example 30(a) for the compound of Example 29(a), gives the title compound.

EXAMPLE 31

Preparation of 1-[2-[(2-(Pyridinyl)amino]ethyl]3-[4-[2-(carboxy)ethyl)]phenyl]-3-oxo-imidazolidine a) Ethyl 2-[4-(2-hydroxyethylamino)phenyl]propionate Following the procedure of Himmelsbach, et. al., EP 0587134, Example V, glycolaldehyde dimer (Aldrich) (1 mmol) is added to a solution of methyl 2-(4-aminophenyl) propionate (1 mmol) in aqueous $CH_3CN$ (pH 6–7) (10 mL), followed by $NaBH_3CN$ (1.2 mmol), and the mixture is allowed to stir for 1 h. The mixture concentrated to an oil, and the residue is dissolved in a mixture of ice water and EtOAc. The aqueous layer is neutralized with 4N NaOH and washed with EtOAc. The organic phase is concentrated to an oil. A solution of the oil in EtOAc is chromatographed (silica gel, gradient, 5–30% $CH_3OH/CH_2Cl_2$-0.1% HOAc). The fractions containing the product are combined and concentrated to give the title compound.

b) N-[2-[(2-Pyridinyl)amino]ethyl]-N'-hydroxyethyl-N'-[4-[2-(ethoxycarbonyl)ethyl)]phenyl]-urea Following the procedures of Himmelsbach, et. al., EP 0587134 and EP 0612741, a solution of the compound of Preparation V(c) (1 mmol) and $COCl_2$ in THF (10 mL) is allowed to stir at −20° C. for 20 min. After 20 min, the compound of Example 31(a) (1 mmol) is added to the solution and the resulting mixture is allowed to stir for 18 h. The resulting solution is concentrated and a solution of the residue in EtOAc is washed with 5% citric acid followed by $H_2O$. The organic phase is concentrated and a solution of the resulting oil in EtOAc is chromatographed (silica gel, gradient, 5–30% $CH_3OH/CH_2Cl_2$-0.1% HOAc). The fractions containing the product are combined and concentrated to give the title compound.

c) N'-[2-[(2-Pyridinyl)amino]ethyl]-$N^3$-[4-[2-(ethoxycarbonyl)ethyl)]phenyl]-2-oxo-imidazolidine Following the procedures of Himmelsbach, et. al., EP 0587134, Example III, and EP 0612741, a solution of the compound of Example 31(b) (1 mmol), methanesulfonyl chloride (1.1 mmol) and $Et_3N$ (1.1 mmol) in $CH_2Cl_2$ (10 mL) is allowed to stir at 0° for 1 h. The mixture is partitioned between $H_2O$ and $CH_2Cl_2$. The organic phases are combined, dried ($Na_2SO_4$), and concentrated. A solution of the residue and NaI (1.1 mmol) in acetone (10 mL) is heated to reflux for 3 h and then concentrated to an oil. Potassium bis(trimethylsilyl)azide (1.1 mmol) is added to a solution of the residue in DMF (5 mL), cooled to 0°. The solution is allowed to warm to RT over 30 min and then concentrated to an oil. The residue is partioned between $H_2O$ and $CH_2Cl_2$. The organic phases are combined, dried ($Na_2SO_4$), and concentrated. A solution of the oil in EtOAc is chromatographed (silica gel, gradient, 5–30% $CH_3OH/CH_2Cl_2$-0.1% HOAc). The fractions containing the product are combined and concentrated to give the title compound.

d) N'-[2-[(2-Pyridinyl)amino]ethyl]-$N^3$-[4-[2-(carboxyl) ethyl)]phenyl]-2-oxo-imidazolidine Following the procedures of Himmelsbach, et. al., EP 0587134, Example III and EO 061741, in which a solution of the compound of Example 31(c) (1 mmol) and 1N NaOH (1.2 mL, 1.2 mmol) is allowed to stir for 18 h. The mixture is neutralized with conc HCl and chromatographed (silica gel, gradient, 5–30% $CH_3OH/CH_2Cl_2$-0.1% HOAc. The fractions containing the product are combined and concentrated to give the title compound.

EXAMPLE 32

Preparation of [6-[[[2-[(Pyridin-2-yl)amino]ethyl]amino] carbonyl]-1,2,3,4-tetrahydroisoquinolin-2-yl]acetic acid a) Ethyl [6-[[[2-[(pyridin-2-yl)amino]ethyl]amino] carbonyl]-1,2,3,4-tetrahydroisoquinolin-2-yl]acetate A solution of the compound of Preparation O(d) (0.263 g, 1.0 mmol), the compound of Preparation V (0.32 g, 1.0 mmol), EDC (0.191 g, 1.0 mmol), HOBt (0.151 g, 1.0 mmol), and $Et_3N$ (0.235 mL, 2.0 mmol) in DMF (7 mL) is stirred for 8 h. The solution is concentrated and the residue is purified by chromatography (silica gel, gradient, 10–50% $CH_3OH/CH_2Cl_2$) to afford the title compound (0.32 g, 68%)

b) [6-[[[2-[(Pyridin-2-yl)amino]ethyl]amino]carbonyl]-1,2,3,4-tetrahydroisoquinolin-2-yl]acetic acid A solution of the compound of Example 32(a) (0.40 g, 1.0 mmol) in aqueous 1 NaOH (1.5 mL, 1.5 mmol) and EtOH (8 mL) is stirred for 8 h. The solution is concentrated and the residue is purified by chromatography (silica gel, gradient, 25–73% $CH_3OH/CH_2Cl_2$) to afford the title compound (0.32 g, 69%).

EXAMPLE 33

Preparation of [6-[[[2-[(Pyridin-2-yl)amino]ethyl]amino] carbonyl]-1,2,3,4-tetrahydro-1-oxo-isoquinolin-2-yl]acetic acid Following the procedure of Example 32(a), except substituting the compound of Preparation P(d) for the compound of Preparation O(d), gives the title compound.

EXAMPLE 34

Preparation of [6-[[[2-[(Pyridin-2-yl)amino]ethyl]carbonyl] amino]tetralin-2-yl]acetic acid a) tert-Butyl [6-[[[2-[(Pyridin-2-yl)amino]ethyl]carbonyl] amino]tetralin-2-yl]acetate Following the procedure of Example 32(a), except substituting tert-butyl (6-amino-tetralin-2-yl)acetate, Fisher, et. al., EO 0635492, Scheme 12 and Example 28, parts A–D, for the compound of Preparation O(d) and substituting N-(2-pyridinyl)-β-alanine, Chowdhary, et. al., Indian J. Chem., 1990, 29A, 280–284, for the compound of Preparation V, gives the title compound.

g) [6-[[[2-[(Pyridin-2-yl)amino]ethyl]carbonyl]amino] tetralin-2-yl]acetic acid

A solution of the compound of Example 34(a) (0.20 g, 0.85 mmol) and TFA (3 mL) in $CH_2Cl_2$ (3 mL) is allowed to stir for 1 h. The solution is concentrated to an oil which is treated with $Et_2O$. Filtration and drying in vacuo afforded the title compound (0.173 g, 74%).

EXAMPLE 35

Preparation of [6-[[[2-[(Pyridin-2-yl)amino]ethyl]amino] carbonyl]tetralin-2-yl]acetic acid a) Ethyl [6-[[[2-[(Pyridin-2-yl)amino]ethyl]amino] carbonyl]tetralin-2-yl]acetic acid Following the procedure of Example 32(a), except substituting the compound of Example 27(b) for the compound of Example 25(d), gives the title compound.

Alternatively, a solution of the compound of Preparation Q(a) (0.31 g, 1.0 mmol), the compound of Preparation V (0.32 g, 1.0 mmol), $Pd(OAc)_2$ (0.023 g, 0.1 mmol), $Ph_3P$ (0.262 g, 1.0 mmol), diisopropylamine (0.23 mL, 2.1 mmol), and NMP (8 mL) in 10% $NH_4CO_3$ is stirred for 8 h under an atmosphere of CO. The solution is concentrated and the residue is purified by chromatography (silica gel, gradient, 10–66% $CH_3OH/CH_2Cl_2$) 8:1 to 1:2) to afford the title compound (0.28 g, 50%)

b) [6-[[[2-[(Pyridin-2-yl)amino]ethyl]amino]carbonyl]tetralin-2-yl]acetic acid

Following the procedure of Example 32(b), except substituting the compound of Example 35(a) for the compound of Example 32(a), gives the title compound.

EXAMPLE 36

Preparation of [5-[[[[(6-Amino-2-pyridinyl)methyl]carbonyl]amino]benzofuran-2-yl]propionic acid Following the procedure of Example 32, except substituting ethyl (5-aminobenzofuran-2-yl)propionate from Preparation R(e) for the compound of Preparation O(d), gives the title compound.

EXAMPLE 37

Preparation of [5-[[[[2-[(Pyridin-2-yl)amino]ethyl]carbonyl]amino]-2,3-dihydro-benzofuran-2-yl]propionic acid Following the procedure of Example 32, except substituting ethyl (5-amino-2,3-dihydro-benzofuran-2-yl) propionate from Preparation R(e) for the compound of Preparation O(d), gives the title compound.

EXAMPLE 38

Preparation of [5-[[[[2-[(Pyridin-2-yl)amino]ethyl]methylamino]carbonyl]benzofuran-2-yl]propionic acid Following the procedure of Example 35, except substituting the compounds of Preparation S(d) or (e) for the compounds of Preparation Q(a) or (b), gives the title compound.

EXAMPLE 39

Preparation of [5-[[[[2-[(Pyridin-2-yl)amino]ethyl]methylamino]carbonyl]-2,3-dihydro-benzofuran-2-yl]-propionic acid Following the procedure of Example 35, except substituting the compounds of Preparation T(a) or (b) for the compounds of Preparation Q(a) or (b), gives the title compound.

EXAMPLE 40

Preparation of (±)-3-[[[5-[(Pyridin-2-yl)amino]pentanoyl]glycyl]amino]-4-pentynoic acid a) Ethyl (±)-3-[[[5-[(pyridin-2-yl)amino]pentanoyl]glycyl]amino]-4-pentynoate DIEA (5.43 mmol) is added to a stirred solution of the compound of Preparation U(b) (1.76 mmol), the compound of Preparation I(c) (1.55 mmol), HOBt . $H_2O$ (2.33 mmol), and EDC (2.33 mmol) in anhydrous $CH_3CN$ (15 mL) at Rt. The reaction mixture is stirred, concentrated, diluted with $CH_2Cl_2$ (100 mL), and washed sequentially with 5% $NaHCO_3$ and brine. Drying ($MgSO_4$), concentration, and chromatography (silica gel, $CH_3OH/CH_2Cl_2$) gives the title compound.

b) (±)-3-[[[5-[(Pyridin-2-yl)amino]pentanoyl]glycyl]amino]-4-pentynoic acid 1.0N LiOH (0.71 mmol) is added dropwise at RT to a mixture of the compound of Preparation EE(a) (0.285 mmol) in THF (5 mL), $H_2O$ (5 mL) and $CH_3CN$ (1 mL). The mixture is stirred, concentrated to a small volume, and cooled in an ice bath before netutralizing with 1.0N AcOH (0.70 mL). The solution is lyophilized and the residue is purified by chromatography (ODS, $CH_3CN/H_2O$-0.1% TFA) to give the title compound.

The above description fully discloses how to make and use the present invention. However, the present invention is not limited to the particular embodiments described hereinabove, but includes all modifications thereof within the scope of the following claims. The various references to journals, patents and other publications which are cited herein comprises the state of the art and are incorporated herein by reference as though fully set forth.

What is claimed is:

1. A compound which is:

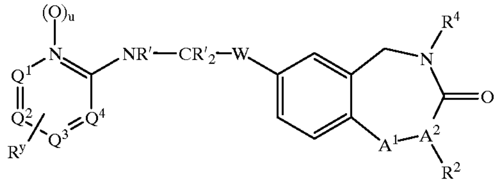

wherein $A^1$-$A^2$ is NH—CH;

$R^2$ is $CH_2CO_2H$;

$R^4$ is H, $C_{1-6}$alkyl, Ar-$C_{0-6}$alkyl, Het-$C_{0-6}$alkyl, or $C_{3-6}$cycloalkyl-$C_{0-6}$alkyl;

W is —$(CHR^g)_a$—$CONR^i$— or —$(CHR^g)_a$—$NR^iCO$—;

$Q^1$, $Q^2$, $Q^3$ and $Q^4$ are each C—$R^y$;

R' is is H or $C_{1-6}$alkyl, $C_{3-7}$cycloalkyl-$C_{0-6}$alkyl or Ar-$C_{0-6}$alkyl;

$R^g$ is H or $C_{1-6}$alkyl, Het-$C_{0-6}$alkyl, $C_{3-7}$cycloalkyl-$C_{0-6}$alkyl or Ar-$C_{0-6}$alkyl;

$R^1$ is H;

$R^y$ is H;

a is 0, 1, 2 or 3; and u is 0.

2. A compound according to claim 1 which is:

(S)-2,3,4,5-Tetrahydro-4-methyl-3-oxo-7-[[[2-[2-pyridinyl)amino]ethyl]amino]carbonyl]-1H-1,4-benzodiazepine-2-acetic acid;

(S)-2,3,4,5-Tetrahydro-3-oxo-7-[[[2-[2-(pyridinyl)amino]ethyl]amino]carbonyl]-1H-1,4-benzodiazepine-2-acetic acid;

(S)-2,3,4,5-Tetrahydro-3-oxo-7-[[2-[2-(pyridinyl)amino]ethyl]amino]carbonyl]-4-(2,2,2-trifluoroethyl)-1H-1,4-benzodiazepine-2-acetic acid;

(±)-2,3,4,5-Tetrahydro-3-oxo-4-(phenylethyl)-7-[[[2-[2-(pyridinyl)amino]ethyl]amino]carbonyl]-1H-1,4-benzodiazepine-2-acetic acid; or (S)-2,3,4,5-Tetrahydro-4-methyl-3-oxo-[[[2-[2-(pyridinyl)amino]ethyl]methylamino]carbonyl]-1H-1,4-benzodiazepine-2-acetic acid.

3. A pharmaceutical composition which comprises a compound according to claim 1 and a pharmaceutically acceptable carrier.

4. A method of treating a disease state in which antagonism of the vitronectin receptor is indicated which comprises administering a compound according to claim 1.

5. A method according to claim 4 for inhibiting angiogenesis or treating atherosclerosis, restenosis, inflammation, or osteoporosis.

* * * * *